United States Patent
Chen et al.

(10) Patent No.: US 11,261,214 B2
(45) Date of Patent: *Mar. 1, 2022

(54) BICYCLIC PEPTIDE LIGAND SPECIFIC FOR CD137

(71) Applicant: BicycleTx Limited, Cambridge (GB)

(72) Inventors: Liuhong Chen, Cambridge (GB); Rachid Lani, Cambridge (GB); Kevin McDonnell, Lexington, MA (US); Gemma Mudd, Cambridge (GB); Peter Park, Lincoln, MA (US)

(73) Assignee: BicycleTx Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/636,105

(22) PCT Filed: Aug. 3, 2018

(86) PCT No.: PCT/GB2018/052222
§ 371 (c)(1),
(2) Date: Feb. 3, 2020

(87) PCT Pub. No.: WO2019/025811
PCT Pub. Date: Feb. 7, 2019

(65) Prior Publication Data
US 2020/0255477 A1    Aug. 13, 2020

(30) Foreign Application Priority Data

Aug. 4, 2017 (GB) .................................. 1712589
Feb. 23, 2018 (GB) .................................. 1802934
Apr. 9, 2018 (GB) .................................. 1805850

(51) Int. Cl.
*C07K 7/64* (2006.01)
*A61K 47/64* (2017.01)
*A61K 38/00* (2006.01)

(52) U.S. Cl.
CPC ................ *C07K 7/64* (2013.01); *A61K 47/64* (2017.08); *A61K 38/00* (2013.01)

(58) Field of Classification Search
None
See application file for complete search history.

(56) References Cited

U.S. PATENT DOCUMENTS

| 10,875,894 | B2 | 12/2020 | Chen et al. |
| 2019/0307836 | A1 | 10/2019 | Keen et al. |
| 2021/0040154 | A1 | 2/2021 | Mudd et al. |
| 2021/0069287 | A1 | 3/2021 | Mudd et al. |
| 2021/0101933 | A1 | 4/2021 | Chen et al. |
| 2021/0101937 | A1 | 4/2021 | Mudd et al. |

FOREIGN PATENT DOCUMENTS

| WO | WO-2004077062 A2 | 9/2004 |
| WO | WO-2012057624 A1 | 5/2012 |
| WO | WO-2017191460 A1 | 11/2017 |
| WO | WO-2019025811 A1 | 2/2019 |
| WO | WO-2019162682 A1 | 8/2019 |
| WO | WO-2019193328 A1 | 10/2019 |
| WO | WO-2021019243 A1 | 2/2021 |
| WO | WO-2021064428 A1 | 4/2021 |

OTHER PUBLICATIONS

Chen et al., "Peptide Ligands Stabilized by Small Molecules," Angew. Chem. Int. Ed., vol. 53, No. 6, Feb. 2014 (pp. 1602-1606).
Heinis et al., "Phage-encoded combinatorial chemical libraries based on bicyclic peptides," Nature Chemical Biology, vol. 5, No. 7, Jul. 2009 (pp. 502-507).
International Search Report and Written Opinion issued by the European Patent Office as International Searching Authority for International Application No. PCT/GB2018/052222, dated Oct. 11, 2018 (9 pages).
Loktev et al., "Multicyclic Peptides as Scaffold for the Development of Tumor Targeting Agents," Current Medicinal Chemistry, 2017, vol. 24, pp. 2141-2155.
Morrison, "Chemical Strategies for Bicyclic Peptide Formation," Univ. of Leeds, Sep. 2015, 160 Pages.
Mulder et al., "Scaffold Optimization in Discontinuous Epitope Containing Protein Mimics of gp120 Using Smart Libraries," Org. Biomol. Chem. 2013, vol. 11, pp. 2676-2684.
Pickens et al., "Practical Considerations, Challenges and Limitations of Bioconjugation via Azide-Alkyne Cycloaddition," Bioconjugate Chem., 2018, vol. 29, pp. 686-701.
Smeenk et al., "Reconstructing the Discontinuous and Confirmational β1/β3-Loop Binding Site on hFSH/hCG by Using Highly Constrained Multicyclic Peptides," ChemBioChem 2015, vol. 16, pp. 91-99.

*Primary Examiner* — Thomas S Heard
(74) *Attorney, Agent, or Firm* — Dechert LLP; Andrea L. C. Reid; Gang Wang

(57) ABSTRACT

The present invention relates to polypeptides which are covalently bound to molecular scaffolds such that two or more peptide loops are subtended between attachment points to the scaffold. In particular, the invention describes peptides which are high affinity binders of CD137. The invention also includes drug conjugates comprising said peptides, conjugated to one or more effector and/or functional groups, to pharmaceutical compositions comprising said peptide ligands and drug conjugates and to the use of said peptide ligands and drug conjugates in preventing, suppressing or treating a disease or disorder mediated by CD137.

25 Claims, 2 Drawing Sheets

Specification includes a Sequence Listing.

SEQUENCE LISTING

```
<160> NUMBER OF SEQ ID NOS: 267

<210> SEQ ID NO 1
<211> LENGTH: 15
<212> TYPE: PRT
<213> ORGANISM: Artificial
<220> FEATURE:
<223> OTHER INFORMATION: Synthetic Peptide

<400> SEQUENCE: 1

Cys Ile Glu Glu Gly Gln Tyr Cys Tyr Arg Asp Met Tyr Met Cys
1               5                   10                  15

<210> SEQ ID NO 2
<211> LENGTH: 15
<212> TYPE: PRT
<213> ORGANISM: Artificial
<220> FEATURE:
<223> OTHER INFORMATION: Synthetic Peptide

<400> SEQUENCE: 2

Cys Ile Glu Glu Gly Gln Tyr Cys Tyr Ala Asp Pro Tyr Met Cys
1               5                   10                  15

<210> SEQ ID NO 3
<211> LENGTH: 15
<212> TYPE: PRT
<213> ORGANISM: Artificial
<220> FEATURE:
<223> OTHER INFORMATION: Synthetic Peptide

<400> SEQUENCE: 3

Cys Ile Glu Glu Gly Gln Tyr Cys Tyr Ala Asp Pro Tyr Tyr Cys
1               5                   10                  15

<210> SEQ ID NO 4
<211> LENGTH: 15
<212> TYPE: PRT
<213> ORGANISM: Artificial
<220> FEATURE:
<223> OTHER INFORMATION: Synthetic Peptide

<400> SEQUENCE: 4

Cys Ile Glu Glu Gly Gln Tyr Cys Tyr Ser Asp Pro Tyr Tyr Cys
1               5                   10                  15

<210> SEQ ID NO 5
<211> LENGTH: 15
<212> TYPE: PRT
<213> ORGANISM: Artificial
<220> FEATURE:
<223> OTHER INFORMATION: Synthetic Peptide

<400> SEQUENCE: 5

Cys Ile Glu Glu Gly Gln Tyr Cys Phe Ala Asp Pro Tyr Met Cys
```

```
<210> SEQ ID NO 6
<211> LENGTH: 15
<212> TYPE: PRT
<213> ORGANISM: Artificial
<220> FEATURE:
<223> OTHER INFORMATION: Synthetic Peptide

<400> SEQUENCE: 6

Cys Ile Glu Glu Gly Gln Tyr Cys Tyr Ala Asp His Gln Leu Cys
1               5                   10                  15

<210> SEQ ID NO 7
<211> LENGTH: 15
<212> TYPE: PRT
<213> ORGANISM: Artificial
<220> FEATURE:
<223> OTHER INFORMATION: Synthetic Peptide

<400> SEQUENCE: 7

Cys Ile Glu Glu Gly Gln Tyr Cys His Ala Asp Pro Tyr Tyr Cys
1               5                   10                  15

<210> SEQ ID NO 8
<211> LENGTH: 15
<212> TYPE: PRT
<213> ORGANISM: Artificial
<220> FEATURE:
<223> OTHER INFORMATION: Synthetic Peptide

<400> SEQUENCE: 8

Cys Ile Glu Glu Gly Gln Tyr Cys His Ala Asp Pro Tyr Phe Cys
1               5                   10                  15

<210> SEQ ID NO 9
<211> LENGTH: 15
<212> TYPE: PRT
<213> ORGANISM: Artificial
<220> FEATURE:
<223> OTHER INFORMATION: Synthetic Peptide

<400> SEQUENCE: 9

Cys Ile Glu Glu Gly Gln Tyr Cys Tyr Ala Asp His Tyr Met Cys
1               5                   10                  15

<210> SEQ ID NO 10
<211> LENGTH: 15
<212> TYPE: PRT
<213> ORGANISM: Artificial
<220> FEATURE:
<223> OTHER INFORMATION: Synthetic Peptide

<400> SEQUENCE: 10

Cys Ile Glu Glu Gly Gln Tyr Cys Tyr Ala Asp Pro Tyr Leu Cys
1               5                   10                  15

<210> SEQ ID NO 11
<211> LENGTH: 15
<212> TYPE: PRT
<213> ORGANISM: Artificial
<220> FEATURE:
<223> OTHER INFORMATION: Synthetic Peptide

<400> SEQUENCE: 11

Cys Ile Glu Glu Gly Gln Tyr Cys Tyr Ser Asp Pro Tyr Leu Cys
1               5                   10                  15
```

```
<210> SEQ ID NO 12
<211> LENGTH: 15
<212> TYPE: PRT
<213> ORGANISM: Artificial
<220> FEATURE:
<223> OTHER INFORMATION: Synthetic Peptide

<400> SEQUENCE: 12

Cys Ile Glu Glu Gly Gln Tyr Cys Phe Ala Asp Pro Tyr Leu Cys
1               5                   10                  15

<210> SEQ ID NO 13
<211> LENGTH: 15
<212> TYPE: PRT
<213> ORGANISM: Artificial
<220> FEATURE:
<223> OTHER INFORMATION: Synthetic Peptide

<400> SEQUENCE: 13

Cys Ile Glu Glu Gly Gln Tyr Cys His Ala Asp Pro Tyr Met Cys
1               5                   10                  15

<210> SEQ ID NO 14
<211> LENGTH: 15
<212> TYPE: PRT
<213> ORGANISM: Artificial
<220> FEATURE:
<223> OTHER INFORMATION: Synthetic Peptide

<400> SEQUENCE: 14

Cys Ile Glu Glu Gly Gln Tyr Cys His Ala Asp Pro Gln Met Cys
1               5                   10                  15

<210> SEQ ID NO 15
<211> LENGTH: 15
<212> TYPE: PRT
<213> ORGANISM: Artificial
<220> FEATURE:
<223> OTHER INFORMATION: Synthetic Peptide

<400> SEQUENCE: 15

Cys Asp Ile Gly Pro Pro Tyr Cys Tyr Arg Asp Met Tyr Met Cys
1               5                   10                  15

<210> SEQ ID NO 16
<211> LENGTH: 15
<212> TYPE: PRT
<213> ORGANISM: Artificial
<220> FEATURE:
<223> OTHER INFORMATION: Synthetic Peptide

<400> SEQUENCE: 16

Cys Asp Ile Gly Pro Pro Tyr Cys Tyr Ala Asp Pro Tyr Met Cys
1               5                   10                  15

<210> SEQ ID NO 17
<211> LENGTH: 14
<212> TYPE: PRT
<213> ORGANISM: Artificial
<220> FEATURE:
<223> OTHER INFORMATION: Synthetic Peptide

<400> SEQUENCE: 17

Cys Asp Glu Trp Gly Leu Phe Cys Ile Pro His Ser Asp Cys
1               5                   10
```

```
<210> SEQ ID NO 18
<211> LENGTH: 14
<212> TYPE: PRT
<213> ORGANISM: Artificial
<220> FEATURE:
<223> OTHER INFORMATION: Synthetic Peptide

<400> SEQUENCE: 18

Cys Asp Glu Trp Gly Leu Tyr Cys Phe Ala His Pro Asp Cys
1               5                   10

<210> SEQ ID NO 19
<211> LENGTH: 15
<212> TYPE: PRT
<213> ORGANISM: Artificial
<220> FEATURE:
<223> OTHER INFORMATION: Synthetic Peptide

<400> SEQUENCE: 19

Cys Ile Glu Pro Gly Pro Phe Cys Tyr Ala Asp Pro Tyr Met Cys
1               5                   10                  15

<210> SEQ ID NO 20
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: X
<222> LOCATION: (13)..(13)
<223> OTHER INFORMATION: X represents Y, Q or M
<220> FEATURE:
<221> NAME/KEY: misc_feature
<222> LOCATION: (14)..(14)
<223> OTHER INFORMATION: Xaa can be any naturally occurring amino acid

<400> SEQUENCE: 20

Cys Ile Glu Glu Gly Gln Tyr Cys Xaa Xaa Asp Xaa Xaa Xaa Cys
1               5                   10                  15

<210> SEQ ID NO 21
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents R or A
<220> FEATURE:
<221> NAME/KEY: X
<222> LOCATION: (12)..(12)
<223> OTHER INFORMATION: X represents M or P

<400> SEQUENCE: 21

Cys Asp Ile Gly Pro Pro Tyr Cys Tyr Xaa Asp Xaa Tyr Met Cys
1               5                   10                  15

<210> SEQ ID NO 22
<211> LENGTH: 14
```

```
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (7)..(7)
<223> OTHER INFORMATION: X represents F or Y
<220> FEATURE:
<221> NAME/KEY: X
<222> LOCATION: (9)..(9)
<223> OTHER INFORMATION: X represents I or F
<220> FEATURE:
<221> NAME/KEY: X
<222> LOCATION: (10)..(10)
<223> OTHER INFORMATION: X represents P or A
<220> FEATURE:
<221> NAME/KEY: X
<222> LOCATION: (12)..(12)
<223> OTHER INFORMATION: X represents S or P

<400> SEQUENCE: 22

Cys Asp Glu Trp Gly Leu Xaa Cys Xaa Xaa His Xaa Asp Cys
1               5                   10

<210> SEQ ID NO 23
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represent Nle

<400> SEQUENCE: 23

Cys Ile Glu Glu Gly Gln Tyr Cys Phe Ala Asp Pro Tyr Xaa Cys
1               5                   10                  15

<210> SEQ ID NO 24
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents Nle

<400> SEQUENCE: 24

Cys Ile Lys Glu Gly Gln Tyr Cys Phe Ala Asp Pro Tyr Xaa Cys
1               5                   10                  15

<210> SEQ ID NO 25
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents Nle

<400> SEQUENCE: 25

Cys Ile Glu Lys Gly Gln Tyr Cys Phe Ala Asp Pro Tyr Xaa Cys
1               5                   10                  15

<210> SEQ ID NO 26
```

```
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents Nle

<400> SEQUENCE: 26

Cys Ile Glu Glu Lys Gln Tyr Cys Phe Ala Asp Pro Tyr Xaa Cys
1               5                   10                  15

<210> SEQ ID NO 27
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents Nle

<400> SEQUENCE: 27

Cys Ile Glu Glu Gly Lys Tyr Cys Phe Ala Asp Pro Tyr Xaa Cys
1               5                   10                  15

<210> SEQ ID NO 28
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents Nle

<400> SEQUENCE: 28

Cys Ile Glu Glu Gly Gln Tyr Cys Lys Ala Asp Pro Tyr Xaa Cys
1               5                   10                  15

<210> SEQ ID NO 29
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents Nle

<400> SEQUENCE: 29

Cys Ile Glu Glu Gly Gln Tyr Cys Phe Ala Asp Lys Tyr Xaa Cys
1               5                   10                  15

<210> SEQ ID NO 30
<211> LENGTH: 15
<212> TYPE: PRT
<213> ORGANISM: Artificial
<220> FEATURE:
<223> OTHER INFORMATION: Synthetic Peptide

<400> SEQUENCE: 30

Cys Ile Glu Glu Gly Gln Tyr Cys Phe Ala Asp Pro Tyr Lys Cys
1               5                   10                  15
```

<210> SEQ ID NO 31
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 31

Ala Cys Ile Glu Glu Gly Gln Tyr Cys Phe Ala Asp Pro Tyr Xaa Cys
1               5                   10                  15
Ala

<210> SEQ ID NO 32
<211> LENGTH: 16
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 32

Ala Cys Ile Glu Glu Gly Gln Tyr Cys Phe Ala Asp Pro Tyr Xaa Cys
1               5                   10                  15

<210> SEQ ID NO 33
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 33

Ala Cys Ile Lys Glu Gly Gln Tyr Cys Phe Ala Asp Pro Tyr Xaa Cys
1               5                   10                  15
Ala

<210> SEQ ID NO 34
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 34

Ala Cys Ile Glu Lys Gly Gln Tyr Cys Phe Ala Asp Pro Tyr Xaa Cys
1               5                   10                  15
Ala

<210> SEQ ID NO 35
<211> LENGTH: 17
<212> TYPE: PRT
<213> ORGANISM: Artificial

```
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 35

Ala Cys Ile Glu Glu Lys Gln Tyr Cys Phe Ala Asp Pro Tyr Xaa Cys
1               5                   10                  15

Ala

<210> SEQ ID NO 36
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 36

Ala Cys Ile Glu Glu Gly Lys Tyr Cys Phe Ala Asp Pro Tyr Xaa Cys
1               5                   10                  15

Ala

<210> SEQ ID NO 37
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 37

Ala Cys Ile Glu Glu Gly Gln Tyr Cys Lys Ala Asp Pro Tyr Xaa Cys
1               5                   10                  15

Ala

<210> SEQ ID NO 38
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 38

Ala Cys Ile Glu Glu Gly Gln Tyr Cys Phe Ala Asp Lys Tyr Xaa Cys
1               5                   10                  15

Ala

<210> SEQ ID NO 39
<211> LENGTH: 17
<212> TYPE: PRT
<213> ORGANISM: Artificial
<220> FEATURE:
<223> OTHER INFORMATION: Synthetic Peptide
```

```
<400> SEQUENCE: 39

Ala Cys Ile Glu Glu Gly Gln Tyr Cys Phe Ala Asp Pro Tyr Lys Cys
1               5                   10                  15

Ala

<210> SEQ ID NO 40
<211> LENGTH: 15
<212> TYPE: PRT
<213> ORGANISM: Artificial
<220> FEATURE:
<223> OTHER INFORMATION: Synthetic Peptide

<400> SEQUENCE: 40

Cys Leu Pro Pro Gly Gln Tyr Cys Phe Pro Asp Leu Leu Leu Cys
1               5                   10                  15

<210> SEQ ID NO 41
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (2)..(2)
<223> OTHER INFORMATION: X represents I, L, M or V
<220> FEATURE:
<221> NAME/KEY: X
<222> LOCATION: (3)..(3)
<223> OTHER INFORMATION: X represents E, D, P or S
<220> FEATURE:
<221> NAME/KEY: X
<222> LOCATION: (4)..(4)
<223> OTHER INFORMATION: X represents P, E or A
<220> FEATURE:
<221> NAME/KEY: X
<222> LOCATION: (6)..(6)
<223> OTHER INFORMATION: X represents P or Q
<220> FEATURE:
<221> NAME/KEY: X
<222> LOCATION: (7)..(7)
<223> OTHER INFORMATION: X represents Y or F
<220> FEATURE:
<221> NAME/KEY: X
<222> LOCATION: (13)..(13)
<223> OTHER INFORMATION: X represents Y or M
<220> FEATURE:
<221> NAME/KEY: X
<222> LOCATION: (14)..(14)
<223> OTHER INFORMATION: X represents M, L or Y

<400> SEQUENCE: 41

Cys Xaa Xaa Xaa Gly Xaa Xaa Cys Tyr Ala Asp Pro Xaa Xaa Cys
1               5                   10                  15

<210> SEQ ID NO 42
<211> LENGTH: 17
<212> TYPE: PRT
<213> ORGANISM: Artificial
<220> FEATURE:
<223> OTHER INFORMATION: Synthetic Peptide

<400> SEQUENCE: 42

Ala Cys Ile Glu Glu Gly Gln Tyr Cys Tyr Arg Asp Met Tyr Met Cys
1               5                   10                  15

Ala

<210> SEQ ID NO 43
<211> LENGTH: 17
```

```
<210> SEQ ID NO 43
<211> LENGTH: 17
<212> TYPE: PRT
<213> ORGANISM: Artificial
<220> FEATURE:
<223> OTHER INFORMATION: Synthetic Peptide

<400> SEQUENCE: 43

Ala Cys Ile Glu Glu Gly Gln Tyr Cys Tyr Arg Asp Met Tyr Met Cys
1               5                   10                  15

Ala

<210> SEQ ID NO 44
<211> LENGTH: 17
<212> TYPE: PRT
<213> ORGANISM: Artificial
<220> FEATURE:
<223> OTHER INFORMATION: Synthetic Peptide

<400> SEQUENCE: 44

Ala Cys Ile Glu Glu Gly Gln Tyr Cys Tyr Ala Asp Pro Tyr Met Cys
1               5                   10                  15

Ala

<210> SEQ ID NO 45
<211> LENGTH: 17
<212> TYPE: PRT
<213> ORGANISM: Artificial
<220> FEATURE:
<223> OTHER INFORMATION: Synthetic Peptide

<400> SEQUENCE: 45

Ala Cys Ile Glu Glu Gly Gln Tyr Cys Tyr Ala Asp Pro Tyr Met Cys
1               5                   10                  15

Ala

<210> SEQ ID NO 46
<211> LENGTH: 17
<212> TYPE: PRT
<213> ORGANISM: Artificial
<220> FEATURE:
<223> OTHER INFORMATION: Synthetic Peptide

<400> SEQUENCE: 46

Ala Cys Ile Glu Glu Gly Gln Tyr Cys Tyr Ala Asp Pro Tyr Tyr Cys
1               5                   10                  15

Ala

<210> SEQ ID NO 47
<211> LENGTH: 17
<212> TYPE: PRT
<213> ORGANISM: Artificial
<220> FEATURE:
<223> OTHER INFORMATION: Synthetic Peptide

<400> SEQUENCE: 47

Ala Cys Ile Glu Glu Gly Gln Tyr Cys Tyr Ala Asp Pro Tyr Tyr Cys
1               5                   10                  15

Ala

<210> SEQ ID NO 48
<211> LENGTH: 17
<212> TYPE: PRT
<213> ORGANISM: Artificial
<220> FEATURE:
<223> OTHER INFORMATION: Synthetic Peptide
```

<400> SEQUENCE: 48

Ala Cys Ile Glu Glu Gly Gln Tyr Cys Tyr Ser Asp Pro Tyr Tyr Cys
1               5                   10                  15
Ala

<210> SEQ ID NO 49
<211> LENGTH: 17
<212> TYPE: PRT
<213> ORGANISM: Artificial
<220> FEATURE:
<223> OTHER INFORMATION: Synthetic Peptide

<400> SEQUENCE: 49

Ala Cys Ile Glu Glu Gly Gln Tyr Cys Phe Ala Asp Pro Tyr Met Cys
1               5                   10                  15
Ala

<210> SEQ ID NO 50
<211> LENGTH: 17
<212> TYPE: PRT
<213> ORGANISM: Artificial
<220> FEATURE:
<223> OTHER INFORMATION: Synthetic Peptide

<400> SEQUENCE: 50

Ala Cys Ile Glu Glu Gly Gln Tyr Cys Phe Ala Asp Pro Tyr Met Cys
1               5                   10                  15
Ala

<210> SEQ ID NO 51
<211> LENGTH: 15
<212> TYPE: PRT
<213> ORGANISM: Artificial
<220> FEATURE:
<223> OTHER INFORMATION: Synthetic Peptide

<400> SEQUENCE: 51

Cys Lys Glu Glu Gly Gln Tyr Cys Phe Ala Asp Pro Tyr Met Cys
1               5                   10                  15

<210> SEQ ID NO 52
<211> LENGTH: 15
<212> TYPE: PRT
<213> ORGANISM: Artificial
<220> FEATURE:
<223> OTHER INFORMATION: Synthetic Peptide

<400> SEQUENCE: 52

Cys Ile Lys Glu Gly Gln Tyr Cys Phe Ala Asp Pro Tyr Met Cys
1               5                   10                  15

<210> SEQ ID NO 53
<211> LENGTH: 15
<212> TYPE: PRT
<213> ORGANISM: Artificial
<220> FEATURE:
<223> OTHER INFORMATION: Synthetic Peptide

<400> SEQUENCE: 53

Cys Ile Glu Lys Gly Gln Tyr Cys Phe Ala Asp Pro Tyr Met Cys
1               5                   10                  15

<210> SEQ ID NO 54

```
<211> LENGTH: 15
<212> TYPE: PRT
<213> ORGANISM: Artificial
<220> FEATURE:
<223> OTHER INFORMATION: Synthetic Peptide

<400> SEQUENCE: 54

Cys Ile Glu Glu Lys Gln Tyr Cys Phe Ala Asp Pro Tyr Met Cys
1               5                   10                  15

<210> SEQ ID NO 55
<211> LENGTH: 15
<212> TYPE: PRT
<213> ORGANISM: Artificial
<220> FEATURE:
<223> OTHER INFORMATION: Synthetic Peptide

<400> SEQUENCE: 55

Cys Ile Glu Glu Gly Lys Tyr Cys Phe Ala Asp Pro Tyr Met Cys
1               5                   10                  15

<210> SEQ ID NO 56
<211> LENGTH: 15
<212> TYPE: PRT
<213> ORGANISM: Artificial
<220> FEATURE:
<223> OTHER INFORMATION: Synthetic Peptide

<400> SEQUENCE: 56

Cys Ile Glu Glu Gly Gln Lys Cys Phe Ala Asp Pro Tyr Met Cys
1               5                   10                  15

<210> SEQ ID NO 57
<211> LENGTH: 15
<212> TYPE: PRT
<213> ORGANISM: Artificial
<220> FEATURE:
<223> OTHER INFORMATION: Synthetic Peptide

<400> SEQUENCE: 57

Cys Ile Glu Glu Gly Gln Tyr Cys Lys Ala Asp Pro Tyr Met Cys
1               5                   10                  15

<210> SEQ ID NO 58
<211> LENGTH: 15
<212> TYPE: PRT
<213> ORGANISM: Artificial
<220> FEATURE:
<223> OTHER INFORMATION: Synthetic Peptide

<400> SEQUENCE: 58

Cys Ile Glu Glu Gly Gln Tyr Cys Phe Lys Asp Pro Tyr Met Cys
1               5                   10                  15

<210> SEQ ID NO 59
<211> LENGTH: 15
<212> TYPE: PRT
<213> ORGANISM: Artificial
<220> FEATURE:
<223> OTHER INFORMATION: Synthetic Peptide

<400> SEQUENCE: 59

Cys Ile Glu Glu Gly Gln Tyr Cys Phe Ala Lys Pro Tyr Met Cys
1               5                   10                  15

<210> SEQ ID NO 60
<211> LENGTH: 15
```

```
<212> TYPE: PRT
<213> ORGANISM: Artificial
<220> FEATURE:
<223> OTHER INFORMATION: Synthetic Peptide

<400> SEQUENCE: 60

Cys Ile Glu Glu Gly Gln Tyr Cys Phe Ala Asp Lys Tyr Met Cys
1               5                   10                  15

<210> SEQ ID NO 61
<211> LENGTH: 15
<212> TYPE: PRT
<213> ORGANISM: Artificial
<220> FEATURE:
<223> OTHER INFORMATION: Synthetic Peptide

<400> SEQUENCE: 61

Cys Ile Glu Glu Gly Gln Tyr Cys Phe Ala Asp Pro Lys Met Cys
1               5                   10                  15

<210> SEQ ID NO 62
<211> LENGTH: 15
<212> TYPE: PRT
<213> ORGANISM: Artificial
<220> FEATURE:
<223> OTHER INFORMATION: Synthetic Peptide

<400> SEQUENCE: 62

Cys Ile Glu Glu Gly Gln Tyr Cys Phe Ala Asp Pro Tyr Lys Cys
1               5                   10                  15

<210> SEQ ID NO 63
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents Nle

<400> SEQUENCE: 63

Cys Ile Glu Glu Lys Gln Tyr Cys Phe Ala Asp Pro Tyr Xaa Cys
1               5                   10                  15

<210> SEQ ID NO 64
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 64

Ala Cys Ile Glu Glu Gly Gln Tyr Cys Phe Ala Asp Pro Tyr Xaa Cys
1               5                   10                  15
Ala

<210> SEQ ID NO 65
<211> LENGTH: 17
<212> TYPE: PRT
<213> ORGANISM: Artificial
<220> FEATURE:
<223> OTHER INFORMATION: Synthetic Peptide
```

```
<220> FEATURE:
<221> NAME/KEY: X
<222> LOCATION: (15)..(15)
<223> OTHER INFORMATION: X represents Nle

<400> SEQUENCE: 65

Ala Cys Ile Glu Glu Gly Gln Tyr Cys Phe Ala Asp Pro Tyr Xaa Cys
1               5                   10                  15

Ala

<210> SEQ ID NO 66
<211> LENGTH: 17
<212> TYPE: PRT
<213> ORGANISM: Artificial
<220> FEATURE:
<223> OTHER INFORMATION: Synthetic Peptide

<400> SEQUENCE: 66

Ala Cys Ile Glu Glu Gly Gln Tyr Cys Tyr Ala Asp His Gln Leu Cys
1               5                   10                  15

Ala

<210> SEQ ID NO 67
<211> LENGTH: 17
<212> TYPE: PRT
<213> ORGANISM: Artificial
<220> FEATURE:
<223> OTHER INFORMATION: Synthetic Peptide

<400> SEQUENCE: 67

Ala Cys Ile Glu Glu Gly Gln Tyr Cys His Ala Asp Pro Tyr Tyr Cys
1               5                   10                  15

Ala

<210> SEQ ID NO 68
<211> LENGTH: 17
<212> TYPE: PRT
<213> ORGANISM: Artificial
<220> FEATURE:
<223> OTHER INFORMATION: Synthetic Peptide

<400> SEQUENCE: 68

Ala Cys Ile Glu Glu Gly Gln Tyr Cys His Ala Asp Pro Tyr Phe Cys
1               5                   10                  15

Ala

<210> SEQ ID NO 69
<211> LENGTH: 17
<212> TYPE: PRT
<213> ORGANISM: Artificial
<220> FEATURE:
<223> OTHER INFORMATION: Synthetic Peptide

<400> SEQUENCE: 69

Ala Cys Ile Glu Glu Gly Gln Tyr Cys Tyr Ala Asp His Tyr Met Cys
1               5                   10                  15

Ala

<210> SEQ ID NO 70
<211> LENGTH: 17
<212> TYPE: PRT
<213> ORGANISM: Artificial
<220> FEATURE:
<223> OTHER INFORMATION: Synthetic Peptide
```

<400> SEQUENCE: 70

Ala Cys Ile Glu Glu Gly Gln Tyr Cys Tyr Ala Asp Pro Tyr Leu Cys
1               5                   10                  15

Ala

<210> SEQ ID NO 71
<211> LENGTH: 19
<212> TYPE: PRT
<213> ORGANISM: Artificial
<220> FEATURE:
<223> OTHER INFORMATION: Synthetic Peptide

<400> SEQUENCE: 71

Ala Cys Ile Glu Glu Gly Gln Tyr Cys Tyr Ala Asp Pro Tyr Leu Cys
1               5                   10                  15

Ser Val Gly

<210> SEQ ID NO 72
<211> LENGTH: 19
<212> TYPE: PRT
<213> ORGANISM: Artificial
<220> FEATURE:
<223> OTHER INFORMATION: Synthetic Peptide

<400> SEQUENCE: 72

Ala Cys Ile Glu Glu Gly Gln Tyr Cys Tyr Ala Asp Pro Tyr Leu Cys
1               5                   10                  15

Ser Val Gly

<210> SEQ ID NO 73
<211> LENGTH: 17
<212> TYPE: PRT
<213> ORGANISM: Artificial
<220> FEATURE:
<223> OTHER INFORMATION: Synthetic Peptide

<400> SEQUENCE: 73

Ala Cys Ile Glu Glu Gly Gln Tyr Cys Tyr Ser Asp Pro Tyr Leu Cys
1               5                   10                  15

Ala

<210> SEQ ID NO 74
<211> LENGTH: 17
<212> TYPE: PRT
<213> ORGANISM: Artificial
<220> FEATURE:
<223> OTHER INFORMATION: Synthetic Peptide

<400> SEQUENCE: 74

Ala Cys Ile Glu Glu Gly Gln Tyr Cys Phe Ala Asp Pro Tyr Leu Cys
1               5                   10                  15

Ala

<210> SEQ ID NO 75
<211> LENGTH: 17
<212> TYPE: PRT
<213> ORGANISM: Artificial
<220> FEATURE:
<223> OTHER INFORMATION: Synthetic Peptide

<400> SEQUENCE: 75

Ala Cys Ile Glu Glu Gly Gln Tyr Cys His Ala Asp Pro Tyr Met Cys

<210> SEQ ID NO 76
<211> LENGTH: 17
<212> TYPE: PRT
<213> ORGANISM: Artificial
<220> FEATURE:
<223> OTHER INFORMATION: Synthetic Peptide

<400> SEQUENCE: 76

Ala Cys Ile Glu Glu Gly Gln Tyr Cys His Ala Asp Pro Gln Met Cys
1               5                   10                  15
Ala

<210> SEQ ID NO 77
<211> LENGTH: 17
<212> TYPE: PRT
<213> ORGANISM: Artificial
<220> FEATURE:
<223> OTHER INFORMATION: Synthetic Peptide

<400> SEQUENCE: 77

Ala Cys Asp Ile Gly Pro Pro Tyr Cys Tyr Arg Asp Met Tyr Met Cys
1               5                   10                  15
Ala

<210> SEQ ID NO 78
<211> LENGTH: 16
<212> TYPE: PRT
<213> ORGANISM: Artificial
<220> FEATURE:
<223> OTHER INFORMATION: Synthetic Peptide

<400> SEQUENCE: 78

Ala Asp Ile Gly Pro Pro Tyr Cys Tyr Ala Asp Pro Tyr Met Cys Ala
1               5                   10                  15

<210> SEQ ID NO 79
<211> LENGTH: 17
<212> TYPE: PRT
<213> ORGANISM: Artificial
<220> FEATURE:
<223> OTHER INFORMATION: Synthetic Peptide

<400> SEQUENCE: 79

Ala Cys Leu Asp Pro Gly Pro Phe Cys Phe Ala Asp Pro Tyr Met Cys
1               5                   10                  15
Ala

<210> SEQ ID NO 80
<211> LENGTH: 17
<212> TYPE: PRT
<213> ORGANISM: Artificial
<220> FEATURE:
<223> OTHER INFORMATION: Synthetic Peptide

<400> SEQUENCE: 80

Ala Cys Leu Asp Glu Gly Pro Tyr Cys Phe Ala Asp Pro Tyr Phe Cys
1               5                   10                  15
Ala

<210> SEQ ID NO 81

```
<211> LENGTH: 17
<212> TYPE: PRT
<213> ORGANISM: Artificial
<220> FEATURE:
<223> OTHER INFORMATION: Synthetic Peptide

<400> SEQUENCE: 81

Ala Cys Ile Asn Glu Gly Pro Tyr Cys Phe Ala Asp Pro Tyr Met Cys
1               5                   10                  15
Ala

<210> SEQ ID NO 82
<211> LENGTH: 17
<212> TYPE: PRT
<213> ORGANISM: Artificial
<220> FEATURE:
<223> OTHER INFORMATION: Synthetic Peptide

<400> SEQUENCE: 82

Ala Cys Ile Glu Gln Gly Pro Phe Cys Phe Ala Asp Pro Tyr Met Cys
1               5                   10                  15
Ala

<210> SEQ ID NO 83
<211> LENGTH: 17
<212> TYPE: PRT
<213> ORGANISM: Artificial
<220> FEATURE:
<223> OTHER INFORMATION: Synthetic Peptide

<400> SEQUENCE: 83

Ala Cys Val Glu Glu Gly Pro Phe Cys Phe Ala Asp Pro Tyr Tyr Cys
1               5                   10                  15
Ala

<210> SEQ ID NO 84
<211> LENGTH: 17
<212> TYPE: PRT
<213> ORGANISM: Artificial
<220> FEATURE:
<223> OTHER INFORMATION: Synthetic Peptide

<400> SEQUENCE: 84

Ala Cys Leu Asp Glu Gly Pro Phe Cys Phe Ser Asp Pro Tyr Met Cys
1               5                   10                  15
Ala

<210> SEQ ID NO 85
<211> LENGTH: 16
<212> TYPE: PRT
<213> ORGANISM: Artificial
<220> FEATURE:
<223> OTHER INFORMATION: Synthetic Peptide

<400> SEQUENCE: 85

Ala Cys Asp Glu Trp Gly Leu Phe Cys Ile Pro His Ser Asp Cys Ala
1               5                   10                  15

<210> SEQ ID NO 86
<211> LENGTH: 16
<212> TYPE: PRT
<213> ORGANISM: Artificial
<220> FEATURE:
<223> OTHER INFORMATION: Synthetic Peptide
```

```
<400> SEQUENCE: 86

Ala Cys Asp Glu Trp Gly Leu Tyr Cys Phe Ala His Pro Asp Cys Ala
1               5                   10                  15

<210> SEQ ID NO 87
<211> LENGTH: 19
<212> TYPE: PRT
<213> ORGANISM: Artificial
<220> FEATURE:
<223> OTHER INFORMATION: Synthetic Peptide

<400> SEQUENCE: 87

Ala Cys Leu Asp Pro Gly Pro Tyr Cys Tyr Ala Asp Pro Tyr Met Cys
1               5                   10                  15

Thr Phe His

<210> SEQ ID NO 88
<211> LENGTH: 19
<212> TYPE: PRT
<213> ORGANISM: Artificial
<220> FEATURE:
<223> OTHER INFORMATION: Synthetic Peptide

<400> SEQUENCE: 88

Ala Cys Ile Glu Pro Gly Pro Phe Cys Tyr Ala Asp Pro Tyr Met Cys
1               5                   10                  15

Asn Arg Val

<210> SEQ ID NO 89
<211> LENGTH: 19
<212> TYPE: PRT
<213> ORGANISM: Artificial
<220> FEATURE:
<223> OTHER INFORMATION: Synthetic Peptide

<400> SEQUENCE: 89

Ala Cys Ile Glu Pro Gly Pro Phe Cys Tyr Ala Asp Pro Tyr Met Cys
1               5                   10                  15

Asn Arg Val

<210> SEQ ID NO 90
<211> LENGTH: 19
<212> TYPE: PRT
<213> ORGANISM: Artificial
<220> FEATURE:
<223> OTHER INFORMATION: Synthetic Peptide

<400> SEQUENCE: 90

Ala Cys Leu Glu Pro Gly Pro Tyr Cys Tyr Ala Asp Pro Tyr Met Cys
1               5                   10                  15

Thr His Leu

<210> SEQ ID NO 91
<211> LENGTH: 17
<212> TYPE: PRT
<213> ORGANISM: Artificial
<220> FEATURE:
<223> OTHER INFORMATION: Synthetic Peptide

<400> SEQUENCE: 91

Ala Cys Leu Pro Pro Gly Pro Tyr Cys Phe Pro Asp Pro Tyr Phe Cys
1               5                   10                  15

Ala
```

```
<210> SEQ ID NO 92
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 92

Ala Cys Ile Glu Glu Gly Gln Tyr Cys Phe Ala Asp Pro Tyr Xaa Cys
1               5                   10                  15
Ala

<210> SEQ ID NO 93
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 93

Ala Cys Ala Glu Glu Gly Gln Tyr Cys Phe Ala Asp Pro Tyr Xaa Cys
1               5                   10                  15
Ala

<210> SEQ ID NO 94
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 94

Ala Cys Ile Ala Glu Gly Gln Tyr Cys Phe Ala Asp Pro Tyr Xaa Cys
1               5                   10                  15
Ala

<210> SEQ ID NO 95
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 95

Ala Cys Ile Glu Ala Gly Gln Tyr Cys Phe Ala Asp Pro Tyr Xaa Cys
1               5                   10                  15
Ala

<210> SEQ ID NO 96
```

```
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 96

Ala Cys Ile Glu Glu Ala Gln Tyr Cys Phe Ala Asp Pro Tyr Xaa Cys
1               5                   10                  15

Ala

<210> SEQ ID NO 97
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 97

Ala Cys Ile Glu Glu Gly Ala Tyr Cys Phe Ala Asp Pro Tyr Xaa Cys
1               5                   10                  15

Ala

<210> SEQ ID NO 98
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 98

Ala Cys Ile Glu Glu Gly Gln Ala Cys Phe Ala Asp Pro Tyr Xaa Cys
1               5                   10                  15

Ala

<210> SEQ ID NO 99
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 99

Ala Cys Ile Glu Glu Gly Gln Tyr Cys Ala Ala Asp Pro Tyr Xaa Cys
1               5                   10                  15

Ala

<210> SEQ ID NO 100
<211> LENGTH: 17
<212> TYPE: PRT
<213> ORGANISM: Artificial
```

```
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 100

Ala Cys Ile Glu Glu Gly Gln Tyr Cys Phe Ala Ala Pro Tyr Xaa Cys
1               5                   10                  15

Ala

<210> SEQ ID NO 101
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 101

Ala Cys Ile Glu Glu Gly Gln Tyr Cys Phe Ala Asp Pro Ala Xaa Cys
1               5                   10                  15

Ala

<210> SEQ ID NO 102
<211> LENGTH: 17
<212> TYPE: PRT
<213> ORGANISM: Artificial
<220> FEATURE:
<223> OTHER INFORMATION: Synthetic Peptide

<400> SEQUENCE: 102

Ala Cys Ile Glu Glu Gly Gln Tyr Cys Phe Ala Asp Pro Tyr Ala Cys
1               5                   10                  15

Ala

<210> SEQ ID NO 103
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 103

Ala Cys Ala Glu Glu Gly Gln Tyr Cys Phe Ala Asp Pro Tyr Xaa Cys
1               5                   10                  15

Ala

<210> SEQ ID NO 104
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle
```

```
<400> SEQUENCE: 104

Ala Cys Ile Ala Glu Gly Gln Tyr Cys Phe Ala Asp Pro Tyr Xaa Cys
1               5                   10                  15

Ala

<210> SEQ ID NO 105
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 105

Ala Cys Ile Glu Ala Gly Gln Tyr Cys Phe Ala Asp Pro Tyr Xaa Cys
1               5                   10                  15

Ala

<210> SEQ ID NO 106
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 106

Ala Cys Ile Glu Glu Ala Gln Tyr Cys Phe Ala Asp Pro Tyr Xaa Cys
1               5                   10                  15

Ala

<210> SEQ ID NO 107
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 107

Ala Cys Ile Glu Glu Gly Ala Tyr Cys Phe Ala Asp Pro Tyr Xaa Cys
1               5                   10                  15

Ala

<210> SEQ ID NO 108
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 108

Ala Cys Ile Glu Glu Gly Gln Ala Cys Phe Ala Asp Pro Tyr Xaa Cys
```

```
1               5                   10                  15

Ala

<210> SEQ ID NO 109
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 109

Ala Cys Ile Glu Glu Gly Gln Tyr Cys Ala Ala Asp Pro Tyr Xaa Cys
1               5                   10                  15

Ala

<210> SEQ ID NO 110
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 110

Ala Cys Ile Glu Glu Gly Gln Tyr Cys Phe Ala Asp Pro Tyr Xaa Cys
1               5                   10                  15

Ala

<210> SEQ ID NO 111
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 111

Ala Cys Ile Glu Glu Gly Gln Tyr Cys Phe Ala Ala Pro Tyr Xaa Cys
1               5                   10                  15

Ala

<210> SEQ ID NO 112
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 112

Ala Cys Ile Glu Glu Gly Gln Tyr Cys Phe Ala Asp Ala Tyr Xaa Cys
1               5                   10                  15

Ala
```

```
<210> SEQ ID NO 113
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 113

Ala Cys Ile Glu Glu Gly Gln Tyr Cys Phe Ala Asp Pro Ala Xaa Cys
1               5                   10                  15
Ala

<210> SEQ ID NO 114
<211> LENGTH: 17
<212> TYPE: PRT
<213> ORGANISM: Artificial
<220> FEATURE:
<223> OTHER INFORMATION: Synthetic Peptide

<400> SEQUENCE: 114

Ala Cys Ile Glu Glu Gly Gln Tyr Cys Phe Ala Asp Pro Tyr Ala Cys
1               5                   10                  15
Ala

<210> SEQ ID NO 115
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 115

Ala Cys Leu Glu Glu Gly Gln Tyr Cys Phe Ala Asp Pro Tyr Xaa Cys
1               5                   10                  15
Ala

<210> SEQ ID NO 116
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents Nle
<220> FEATURE:
<221> NAME/KEY: X
<222> LOCATION: (15)..(15)
<223> OTHER INFORMATION: X represents Nle

<400> SEQUENCE: 116

Ala Cys Xaa Glu Glu Gly Gln Tyr Cys Phe Ala Asp Pro Tyr Xaa Cys
1               5                   10                  15
Ala

<210> SEQ ID NO 117
```

```
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents Chg
<220> FEATURE:
<221> NAME/KEY: X
<222> LOCATION: (15)..(15)
<223> OTHER INFORMATION: X represents Nle

<400> SEQUENCE: 117

Ala Cys Xaa Glu Glu Gly Gln Tyr Cys Phe Ala Asp Pro Tyr Xaa Cys
1               5                   10                  15
Ala

<210> SEQ ID NO 118
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents Cha
<220> FEATURE:
<221> NAME/KEY: X
<222> LOCATION: (15)..(15)
<223> OTHER INFORMATION: X represents Nle

<400> SEQUENCE: 118

Ala Cys Xaa Glu Glu Gly Gln Tyr Cys Phe Ala Asp Pro Tyr Xaa Cys
1               5                   10                  15
Ala

<210> SEQ ID NO 119
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 119

Ala Cys Ile Pro Glu Gly Gln Tyr Cys Phe Ala Asp Pro Tyr Xaa Cys
1               5                   10                  15
Ala

<210> SEQ ID NO 120
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 120

Ala Cys Ile Asp Glu Gly Gln Tyr Cys Phe Ala Asp Pro Tyr Xaa Cys
1               5                   10                  15
```

Ala

<210> SEQ ID NO 121
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (4)..(4)
<223> OTHER INFORMATION: X represents Aad
<220> FEATURE:
<221> NAME/KEY: X
<222> LOCATION: (15)..(15)
<223> OTHER INFORMATION: X represents Nle

<400> SEQUENCE: 121

Ala Cys Ile Xaa Glu Gly Gln Tyr Cys Phe Ala Asp Pro Tyr Xaa Cys
1               5                   10                  15

Ala

<210> SEQ ID NO 122
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (4)..(4)
<223> OTHER INFORMATION: X represents Api
<220> FEATURE:
<221> NAME/KEY: X
<222> LOCATION: (15)..(15)
<223> OTHER INFORMATION: X represents Nle

<400> SEQUENCE: 122

Ala Cys Ile Xaa Glu Gly Gln Tyr Cys Phe Ala Asp Pro Tyr Xaa Cys
1               5                   10                  15

Ala

<210> SEQ ID NO 123
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 123

Ala Cys Ile Glu Pro Gly Gln Tyr Cys Phe Ala Asp Pro Tyr Xaa Cys
1               5                   10                  15

Ala

<210> SEQ ID NO 124
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 124

Ala Cys Ile Glu Asp Gly Gln Tyr Cys Phe Ala Asp Pro Tyr Xaa Cys
1               5                   10                  15

Ala

<210> SEQ ID NO 125
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (5)..(5)
<223> OTHER INFORMATION: X represents Aad
<220> FEATURE:
<221> NAME/KEY: X
<222> LOCATION: (15)..(15)
<223> OTHER INFORMATION: X represents Nle

<400> SEQUENCE: 125

Ala Cys Ile Glu Xaa Gly Gln Tyr Cys Phe Ala Asp Pro Tyr Xaa Cys
1               5                   10                  15

Ala

<210> SEQ ID NO 126
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (5)..(5)
<223> OTHER INFORMATION: X represents Api
<220> FEATURE:
<221> NAME/KEY: X
<222> LOCATION: (15)..(15)
<223> OTHER INFORMATION: X represents Nle

<400> SEQUENCE: 126

Ala Cys Ile Glu Xaa Gly Gln Tyr Cys Phe Ala Asp Pro Tyr Xaa Cys
1               5                   10                  15

Ala

<210> SEQ ID NO 127
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (6)..(6)
<223> OTHER INFORMATION: X represents Sar
<220> FEATURE:
<221> NAME/KEY: X
<222> LOCATION: (15)..(15)
<223> OTHER INFORMATION: X represents Nle

<400> SEQUENCE: 127

Ala Cys Ile Glu Glu Xaa Gln Tyr Cys Phe Ala Asp Pro Tyr Xaa Cys
1               5                   10                  15

Ala

<210> SEQ ID NO 128

```
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 128

Ala Cys Ile Glu Glu Lys Gln Tyr Cys Phe Ala Asp Pro Tyr Xaa Cys
1               5                   10                  15
Ala

<210> SEQ ID NO 129
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 129

Ala Cys Ile Glu Glu Phe Gln Tyr Cys Phe Ala Asp Pro Tyr Xaa Cys
1               5                   10                  15
Ala

<210> SEQ ID NO 130
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 130

Ala Cys Ile Glu Glu Glu Gln Tyr Cys Phe Ala Asp Pro Tyr Xaa Cys
1               5                   10                  15
Ala

<210> SEQ ID NO 131
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 131

Ala Cys Ile Glu Glu Gln Gln Tyr Cys Phe Ala Asp Pro Tyr Xaa Cys
1               5                   10                  15
Ala

<210> SEQ ID NO 132
<211> LENGTH: 17
<212> TYPE: PRT
<213> ORGANISM: Artificial
```

```
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 132

Ala Cys Ile Glu Glu Leu Gln Tyr Cys Phe Ala Asp Pro Tyr Xaa Cys
1               5                   10                  15
Ala

<210> SEQ ID NO 133
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 133

Ala Cys Ile Glu Glu Ser Gln Tyr Cys Phe Ala Asp Pro Tyr Xaa Cys
1               5                   10                  15
Ala

<210> SEQ ID NO 134
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (6)..(6)
<223> OTHER INFORMATION: X represents MeD-Ala
<220> FEATURE:
<221> NAME/KEY: X
<222> LOCATION: (15)..(15)
<223> OTHER INFORMATION: X represents Nle

<400> SEQUENCE: 134

Ala Cys Ile Glu Glu Xaa Gln Tyr Cys Phe Ala Asp Pro Tyr Xaa Cys
1               5                   10                  15
Ala

<210> SEQ ID NO 135
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (6)..(6)
<223> OTHER INFORMATION: X represents Aib
<220> FEATURE:
<221> NAME/KEY: X
<222> LOCATION: (15)..(15)
<223> OTHER INFORMATION: X represents Nle

<400> SEQUENCE: 135

Ala Cys Ile Glu Glu Xaa Gln Tyr Cys Phe Ala Asp Pro Tyr Xaa Cys
1               5                   10                  15
Ala
```

<210> SEQ ID NO 136
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 136

Ala Cys Ile Glu Glu Gly Pro Tyr Cys Phe Ala Asp Pro Tyr Xaa Cys
1               5                   10                  15
Ala

<210> SEQ ID NO 137
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 137

Ala Cys Ile Glu Glu Gly Gln Phe Cys Phe Ala Asp Pro Tyr Xaa Cys
1               5                   10                  15
Ala

<210> SEQ ID NO 138
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represents 2MePhe
<220> FEATURE:
<221> NAME/KEY: X
<222> LOCATION: (15)..(15)
<223> OTHER INFORMATION: X represents Nle

<400> SEQUENCE: 138

Ala Cys Ile Glu Glu Gly Gln Xaa Cys Phe Ala Asp Pro Tyr Xaa Cys
1               5                   10                  15
Ala

<210> SEQ ID NO 139
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represents 3MePhe
<220> FEATURE:
<221> NAME/KEY: X
<222> LOCATION: (15)..(15)
<223> OTHER INFORMATION: X represents Nle

<400> SEQUENCE: 139

Ala Cys Ile Glu Glu Gly Gln Xaa Cys Phe Ala Asp Pro Tyr Xaa Cys
1               5                   10                  15

Ala

<210> SEQ ID NO 140
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represents 4MePhe
<220> FEATURE:
<221> NAME/KEY: X
<222> LOCATION: (15)..(15)
<223> OTHER INFORMATION: X represents Nle

<400> SEQUENCE: 140

Ala Cys Ile Glu Glu Gly Gln Xaa Cys Phe Ala Asp Pro Tyr Xaa Cys
1               5                   10                  15

Ala

<210> SEQ ID NO 141
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represents FPhe
<220> FEATURE:
<221> NAME/KEY: X
<222> LOCATION: (15)..(15)
<223> OTHER INFORMATION: X represents Nle

<400> SEQUENCE: 141

Ala Cys Ile Glu Glu Gly Gln Xaa Cys Phe Ala Asp Pro Tyr Xaa Cys
1               5                   10                  15

Ala

<210> SEQ ID NO 142
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represents FPhe
<220> FEATURE:
<221> NAME/KEY: X
<222> LOCATION: (15)..(15)
<223> OTHER INFORMATION: X represents Nle

<400> SEQUENCE: 142

Ala Cys Ile Glu Glu Gly Gln Xaa Cys Phe Ala Asp Pro Tyr Xaa Cys
1               5                   10                  15

Ala

<210> SEQ ID NO 143
<211> LENGTH: 17
<212> TYPE: PRT
<213> ORGANISM: Artificial

```
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represnets MePhe
<220> FEATURE:
<221> NAME/KEY: X
<222> LOCATION: (15)..(15)
<223> OTHER INFORMATION: X represnets Nle

<400> SEQUENCE: 143

Ala Cys Ile Glu Glu Gly Gln Tyr Cys Xaa Ala Asp Pro Tyr Xaa Cys
1               5                   10                  15

Ala

<210> SEQ ID NO 144
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents MePhe
<220> FEATURE:
<221> NAME/KEY: X
<222> LOCATION: (15)..(15)
<223> OTHER INFORMATION: X represents Nle

<400> SEQUENCE: 144

Ala Cys Ile Glu Glu Gly Gln Tyr Cys Xaa Ala Asp Pro Tyr Xaa Cys
1               5                   10                  15

Ala

<210> SEQ ID NO 145
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents MePhe
<220> FEATURE:
<221> NAME/KEY: X
<222> LOCATION: (15)..(15)
<223> OTHER INFORMATION: X represents Nle

<400> SEQUENCE: 145

Ala Cys Ile Glu Glu Gly Gln Tyr Cys Xaa Ala Asp Pro Tyr Xaa Cys
1               5                   10                  15

Ala

<210> SEQ ID NO 146
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents PheG
<220> FEATURE:
<221> NAME/KEY: X
<222> LOCATION: (15)..(15)
<223> OTHER INFORMATION: X represents Nle
```

<400> SEQUENCE: 146

Ala Cys Ile Glu Glu Gly Gln Tyr Cys Xaa Ala Asp Pro Tyr Xaa Cys
1               5                   10                  15

Ala

<210> SEQ ID NO 147
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents FPhe
<220> FEATURE:
<221> NAME/KEY: X
<222> LOCATION: (15)..(15)
<223> OTHER INFORMATION: X represents Nle

<400> SEQUENCE: 147

Ala Cys Ile Glu Glu Gly Gln Tyr Cys Xaa Ala Asp Pro Tyr Xaa Cys
1               5                   10                  15

Ala

<210> SEQ ID NO 148
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 148

Ala Cys Ile Glu Glu Gly Gln Tyr Cys Phe Gly Asp Pro Tyr Xaa Cys
1               5                   10                  15

Ala

<210> SEQ ID NO 149
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 149

Ala Cys Ile Glu Glu Gly Gln Tyr Cys Phe Ser Asp Pro Tyr Xaa Cys
1               5                   10                  15

Ala

<210> SEQ ID NO 150
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)

<223> OTHER INFORMATION: X represents Nle

<400> SEQUENCE: 150

Ala Cys Ile Glu Glu Gly Gln Tyr Cys Phe Pro Asp Pro Tyr Xaa Cys
1               5                   10                  15
Ala

<210> SEQ ID NO 151
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 151

Ala Cys Ile Glu Glu Gly Gln Tyr Cys Phe Ala Asn Pro Tyr Xaa Cys
1               5                   10                  15
Ala

<210> SEQ ID NO 152
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (13)..(13)
<223> OTHER INFORMATION: X represents Pip
<220> FEATURE:
<221> NAME/KEY: X
<222> LOCATION: (15)..(15)
<223> OTHER INFORMATION: X represents Nle

<400> SEQUENCE: 152

Ala Cys Ile Glu Glu Gly Gln Tyr Cys Phe Ala Asp Xaa Tyr Xaa Cys
1               5                   10                  15
Ala

<210> SEQ ID NO 153
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (13)..(13)
<223> OTHER INFORMATION: X represents MeAla
<220> FEATURE:
<221> NAME/KEY: X
<222> LOCATION: (15)..(15)
<223> OTHER INFORMATION: X represents Nle

<400> SEQUENCE: 153

Ala Cys Ile Glu Glu Gly Gln Tyr Cys Phe Ala Asp Xaa Tyr Xaa Cys
1               5                   10                  15
Ala

<210> SEQ ID NO 154
<211> LENGTH: 17
<212> TYPE: PRT
<213> ORGANISM: Artificial

```
<220> FEATURE:
<223> OTHER INFORMATION: Synthetic Peptide
<220> FEATURE:
<221> NAME/KEY: X
<222> LOCATION: (13)..(13)
<223> OTHER INFORMATION: X represents Sar
<220> FEATURE:
<221> NAME/KEY: X
<222> LOCATION: (15)..(15)
<223> OTHER INFORMATION: X represents Nle

<400> SEQUENCE: 154

Ala Cys Ile Glu Glu Gly Gln Tyr Cys Phe Ala Asp Xaa Tyr Xaa Cys
1               5                   10                  15
Ala

<210> SEQ ID NO 155
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (13)..(13)
<223> OTHER INFORMATION: X represents Aib
<220> FEATURE:
<221> NAME/KEY: X
<222> LOCATION: (15)..(15)
<223> OTHER INFORMATION: X represents Nle

<400> SEQUENCE: 155

Ala Cys Ile Glu Glu Gly Gln Tyr Cys Phe Ala Asp Xaa Tyr Xaa Cys
1               5                   10                  15
Ala

<210> SEQ ID NO 156
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents tBuAla
<220> FEATURE:
<221> NAME/KEY: X
<222> LOCATION: (15)..(15)
<223> OTHER INFORMATION: X represents Nle

<400> SEQUENCE: 156

Ala Cys Xaa Glu Glu Gly Gln Tyr Cys Phe Ala Asp Pro Tyr Xaa Cys
1               5                   10                  15
Ala

<210> SEQ ID NO 157
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents HLeu
<220> FEATURE:
<221> NAME/KEY: X
<222> LOCATION: (15)..(15)
<223> OTHER INFORMATION: X represents Nle
```

<400> SEQUENCE: 157

Ala Cys Xaa Glu Glu Gly Gln Tyr Cys Phe Ala Asp Pro Tyr Xaa Cys
1               5                   10                  15
Ala

<210> SEQ ID NO 158
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represents FPhe
<220> FEATURE:
<221> NAME/KEY: X
<222> LOCATION: (15)..(15)
<223> OTHER INFORMATION: X represents Nle

<400> SEQUENCE: 158

Ala Cys Ile Glu Glu Gly Gln Xaa Cys Phe Ala Asp Pro Tyr Xaa Cys
1               5                   10                  15
Ala

<210> SEQ ID NO 159
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents FPhe
<220> FEATURE:
<221> NAME/KEY: X
<222> LOCATION: (15)..(15)
<223> OTHER INFORMATION: X represents Nle

<400> SEQUENCE: 159

Ala Cys Ile Glu Glu Gly Gln Tyr Cys Xaa Ala Asp Pro Tyr Xaa Cys
1               5                   10                  15
Ala

<210> SEQ ID NO 160
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (11)..(11)
<223> OTHER INFORMATION: X represents CF3G
<220> FEATURE:
<221> NAME/KEY: X
<222> LOCATION: (15)..(15)
<223> OTHER INFORMATION: X represents Nle

<400> SEQUENCE: 160

Ala Cys Ile Glu Glu Gly Gln Tyr Cys Phe Xaa Asp Pro Tyr Xaa Cys
1               5                   10                  15
Ala

<210> SEQ ID NO 161

```
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents pCoPhe
<220> FEATURE:
<221> NAME/KEY: X
<222> LOCATION: (15)..(15)
<223> OTHER INFORMATION: X represents Nle

<400> SEQUENCE: 161

Ala Cys Ile Glu Glu Gly Gln Tyr Cys Phe Ala Asp Pro Xaa Xaa Cys
1               5                   10                  15

Ala

<210> SEQ ID NO 162
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents pCaPhe
<220> FEATURE:
<221> NAME/KEY: X
<222> LOCATION: (15)..(15)
<223> OTHER INFORMATION: X represents Nle

<400> SEQUENCE: 162

Ala Cys Ile Glu Glu Gly Gln Tyr Cys Phe Ala Asp Pro Xaa Xaa Cys
1               5                   10                  15

Ala

<210> SEQ ID NO 163
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 163

Ala Cys Ile Glu Glu Gly Gln Tyr Cys Phe Ala Asp Pro Gln Xaa Cys
1               5                   10                  15

Ala

<210> SEQ ID NO 164
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents 2MePhe
<220> FEATURE:
<221> NAME/KEY: X
<222> LOCATION: (15)..(15)
<223> OTHER INFORMATION: X represents Nle
```

<400> SEQUENCE: 164

Ala Cys Ile Glu Glu Gly Gln Tyr Cys Phe Ala Asp Pro Xaa Xaa Cys
1               5                   10                  15
Ala

<210> SEQ ID NO 165
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents 3MePhe
<220> FEATURE:
<221> NAME/KEY: X
<222> LOCATION: (15)..(15)
<223> OTHER INFORMATION: X represents Nle

<400> SEQUENCE: 165

Ala Cys Ile Glu Glu Gly Gln Tyr Cys Phe Ala Asp Pro Xaa Xaa Cys
1               5                   10                  15
Ala

<210> SEQ ID NO 166
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents 4MePhe
<220> FEATURE:
<221> NAME/KEY: X
<222> LOCATION: (15)..(15)
<223> OTHER INFORMATION: X represents Nle

<400> SEQUENCE: 166

Ala Cys Ile Glu Glu Gly Gln Tyr Cys Phe Ala Asp Pro Xaa Xaa Cys
1               5                   10                  15
Ala

<210> SEQ ID NO 167
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents Cit
<220> FEATURE:
<221> NAME/KEY: X
<222> LOCATION: (15)..(15)
<223> OTHER INFORMATION: X represents Nle

<400> SEQUENCE: 167

Ala Cys Ile Glu Glu Gly Gln Tyr Cys Phe Ala Asp Pro Xaa Xaa Cys
1               5                   10                  15
Ala

<210> SEQ ID NO 168
<211> LENGTH: 17

```
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents 4FPhe
<220> FEATURE:
<221> NAME/KEY: X
<222> LOCATION: (15)..(15)
<223> OTHER INFORMATION: X represents Nle

<400> SEQUENCE: 168

Ala Cys Ile Glu Glu Gly Gln Tyr Cys Phe Ala Asp Pro Xaa Xaa Cys
1               5                   10                  15

Ala

<210> SEQ ID NO 169
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents tBuAla

<400> SEQUENCE: 169

Ala Cys Ile Glu Glu Gly Gln Tyr Cys Phe Ala Asp Pro Tyr Xaa Cys
1               5                   10                  15

Ala

<210> SEQ ID NO 170
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents HLeu

<400> SEQUENCE: 170

Ala Cys Ile Glu Glu Gly Gln Tyr Cys Phe Ala Asp Pro Tyr Xaa Cys
1               5                   10                  15

Ala

<210> SEQ ID NO 171
<211> LENGTH: 17
<212> TYPE: PRT
<213> ORGANISM: Artificial
<220> FEATURE:
<223> OTHER INFORMATION: Synthetic Peptide

<400> SEQUENCE: 171

Ala Cys Ile Glu Glu Gly Gln Tyr Cys Phe Ala Asp Pro Tyr Ile Cys
1               5                   10                  15

Ala

<210> SEQ ID NO 172
<211> LENGTH: 17
<212> TYPE: PRT
<213> ORGANISM: Artificial
<220> FEATURE:
```

```
<223> OTHER INFORMATION: Synthetic Peptide
<220> FEATURE:
<221> NAME/KEY: X
<222> LOCATION: (15)..(15)
<223> OTHER INFORMATION: X represents Cha

<400> SEQUENCE: 172

Ala Cys Ile Glu Glu Gly Gln Tyr Cys Phe Ala Asp Pro Tyr Xaa Cys
1               5                   10                  15

Ala

<210> SEQ ID NO 173
<211> LENGTH: 17
<212> TYPE: PRT
<213> ORGANISM: Artificial
<220> FEATURE:
<223> OTHER INFORMATION: Synthetic Peptide

<400> SEQUENCE: 173

Ala Cys Ile Glu Glu Gly Gln Tyr Cys Phe Ala Asp Pro Tyr Phe Cys
1               5                   10                  15

Ala

<210> SEQ ID NO 174
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents 2MePhe

<400> SEQUENCE: 174

Ala Cys Ile Glu Glu Gly Gln Tyr Cys Phe Ala Asp Pro Tyr Xaa Cys
1               5                   10                  15

Ala

<210> SEQ ID NO 175
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents 3MePhe

<400> SEQUENCE: 175

Ala Cys Ile Glu Glu Gly Gln Tyr Cys Phe Ala Asp Pro Tyr Xaa Cys
1               5                   10                  15

Ala

<210> SEQ ID NO 176
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents 4MePhe

<400> SEQUENCE: 176
```

```
Ala Cys Ile Glu Glu Gly Gln Tyr Cys Phe Ala Asp Pro Tyr Xaa Cys
1               5                   10                  15

Ala

<210> SEQ ID NO 177
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (2)..(2)
<223> OTHER INFORMATION: X represents Pen
<220> FEATURE:
<221> NAME/KEY: X
<222> LOCATION: (15)..(15)
<223> OTHER INFORMATION: X represents Nle

<400> SEQUENCE: 177

Ala Xaa Ile Glu Glu Gly Gln Tyr Cys Phe Ala Asp Pro Tyr Xaa Cys
1               5                   10                  15

Ala

<210> SEQ ID NO 178
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (9)..(9)
<223> OTHER INFORMATION: X represents Pen
<220> FEATURE:
<221> NAME/KEY: X
<222> LOCATION: (15)..(15)
<223> OTHER INFORMATION: X represents Nle

<400> SEQUENCE: 178

Ala Cys Ile Glu Glu Gly Gln Tyr Xaa Phe Ala Asp Pro Tyr Xaa Cys
1               5                   10                  15

Ala

<210> SEQ ID NO 179
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle
<220> FEATURE:
<221> NAME/KEY: X
<222> LOCATION: (16)..(16)
<223> OTHER INFORMATION: X represents Pen

<400> SEQUENCE: 179

Ala Cys Ile Glu Glu Gly Gln Tyr Cys Phe Ala Asp Pro Tyr Xaa Xaa
1               5                   10                  15

Ala

<210> SEQ ID NO 180
<211> LENGTH: 17
<212> TYPE: PRT
```

<213> ORGANISM: Artificial
<220> FEATURE:
<223> OTHER INFORMATION: Synthetic Peptide
<220> FEATURE:
<221> NAME/KEY: X
<222> LOCATION: (2)..(2)
<223> OTHER INFORMATION: X represents HCys
<220> FEATURE:
<221> NAME/KEY: X
<222> LOCATION: (15)..(15)
<223> OTHER INFORMATION: X represents Nle

<400> SEQUENCE: 180

Ala Xaa Ile Glu Glu Gly Gln Tyr Cys Phe Ala Asp Pro Tyr Xaa Cys
1               5                   10                  15
Ala

<210> SEQ ID NO 181
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (9)..(9)
<223> OTHER INFORMATION: X represents HCys
<220> FEATURE:
<221> NAME/KEY: X
<222> LOCATION: (15)..(15)
<223> OTHER INFORMATION: X represents Nle

<400> SEQUENCE: 181

Ala Cys Ile Glu Glu Gly Gln Tyr Xaa Phe Ala Asp Pro Tyr Xaa Cys
1               5                   10                  15
Ala

<210> SEQ ID NO 182
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle
<220> FEATURE:
<221> NAME/KEY: X
<222> LOCATION: (16)..(16)
<223> OTHER INFORMATION: X represents HCys

<400> SEQUENCE: 182

Ala Cys Ile Glu Glu Gly Gln Tyr Cys Phe Ala Asp Pro Tyr Xaa Xaa
1               5                   10                  15
Ala

<210> SEQ ID NO 183
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents 3FPhe
<220> FEATURE:
<221> NAME/KEY: X
<222> LOCATION: (15)..(15)

```
<223> OTHER INFORMATION: X represents Nle

<400> SEQUENCE: 183

Ala Cys Ile Glu Glu Gly Gln Tyr Cys Xaa Ala Asp Pro Tyr Xaa Cys
1               5                   10                  15
Ala

<210> SEQ ID NO 184
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (4)..(4)
<223> OTHER INFORMATION: X represents TetraZ
<220> FEATURE:
<221> NAME/KEY: X
<222> LOCATION: (15)..(15)
<223> OTHER INFORMATION: X represents Nle

<400> SEQUENCE: 184

Ala Cys Ile Xaa Glu Gly Gln Tyr Cys Phe Ala Asp Pro Tyr Xaa Cys
1               5                   10                  15
Ala

<210> SEQ ID NO 185
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (12)..(12)
<223> OTHER INFORMATION: X represents TetraZ
<220> FEATURE:
<221> NAME/KEY: X
<222> LOCATION: (15)..(15)
<223> OTHER INFORMATION: X represents Nle

<400> SEQUENCE: 185

Ala Cys Ile Glu Glu Gly Gln Tyr Cys Phe Ala Xaa Pro Tyr Xaa Cys
1               5                   10                  15
Ala

<210> SEQ ID NO 186
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents HGln
<220> FEATURE:
<221> NAME/KEY: X
<222> LOCATION: (15)..(15)
<223> OTHER INFORMATION: X represents Nle

<400> SEQUENCE: 186

Ala Cys Ile Glu Glu Gly Gln Tyr Cys Phe Ala Asp Pro Xaa Xaa Cys
1               5                   10                  15
Ala
```

```
<210> SEQ ID NO 187
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents Ahp
<220> FEATURE:
<221> NAME/KEY: X
<222> LOCATION: (15)..(15)
<223> OTHER INFORMATION: X represents Nle

<400> SEQUENCE: 187

Ala Cys Xaa Glu Glu Gly Gln Tyr Cys Phe Ala Asp Pro Tyr Xaa Cys
1               5                   10                  15

Ala

<210> SEQ ID NO 188
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Ahp

<400> SEQUENCE: 188

Ala Cys Ile Glu Glu Gly Gln Tyr Cys Phe Ala Asp Pro Tyr Xaa Cys
1               5                   10                  15

Ala

<210> SEQ ID NO 189
<211> LENGTH: 17
<212> TYPE: PRT
<213> ORGANISM: Artificial
<220> FEATURE:
<223> OTHER INFORMATION: Synthetic Peptide

<400> SEQUENCE: 189

Ala Cys Ile Glu Glu Gly Gln Tyr Cys Phe Ala Asp Pro Tyr Met Cys
1               5                   10                  15

Ala

<210> SEQ ID NO 190
<211> LENGTH: 19
<212> TYPE: PRT
<213> ORGANISM: Artificial
<220> FEATURE:
<223> OTHER INFORMATION: Synthetic Peptide

<400> SEQUENCE: 190

His Glu His Cys Ile Glu Glu Gly Gln Tyr Cys Tyr Ala Asp Pro Tyr
1               5                   10                  15

Met Cys Ala

<210> SEQ ID NO 191
<211> LENGTH: 17
<212> TYPE: PRT
<213> ORGANISM: Artificial
<220> FEATURE:
<223> OTHER INFORMATION: Synthetic Peptide
```

```
<400> SEQUENCE: 191

Ala Cys Ile Glu Glu Gly Gln Tyr Cys Phe Ala Asp Pro Tyr Leu Cys
1               5                   10                  15

Ala

<210> SEQ ID NO 192
<211> LENGTH: 17
<212> TYPE: PRT
<213> ORGANISM: Artificial
<220> FEATURE:
<223> OTHER INFORMATION: Synthetic Peptide

<400> SEQUENCE: 192

Ala Cys Leu Pro Pro Gly Pro Tyr Cys Phe Pro Asp Pro Tyr Phe Cys
1               5                   10                  15

Ala

<210> SEQ ID NO 193
<211> LENGTH: 15
<212> TYPE: PRT
<213> ORGANISM: Artificial
<220> FEATURE:
<223> OTHER INFORMATION: Synthetic Peptide

<400> SEQUENCE: 193

Cys Ile Glu Glu Gly Gln Tyr Cys Phe Ala Asp Pro Tyr Met Cys
1               5                   10                  15

<210> SEQ ID NO 194
<211> LENGTH: 16
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents Nle
<220> FEATURE:
<221> NAME/KEY: X
<222> LOCATION: (16)..(16)
<223> OTHER INFORMATION: X represents Dap

<400> SEQUENCE: 194

Cys Ile Glu Glu Gly Gln Tyr Cys Phe Ala Asp Pro Tyr Xaa Cys Xaa
1               5                   10                  15

<210> SEQ ID NO 195
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 195

Ala Cys Ile Pro Glu Phe Gln Tyr Cys Phe Ala Asp Pro Tyr Xaa Cys
1               5                   10                  15

Ala

<210> SEQ ID NO 196
<211> LENGTH: 17
<212> TYPE: PRT
```

```
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 196

Ala Cys Ile Pro Glu Phe Pro Tyr Cys Phe Ala Asp Pro Tyr Xaa Cys
1               5                   10                  15

Ala

<210> SEQ ID NO 197
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 197

Ala Cys Ile Glu Glu Phe Pro Tyr Cys Phe Ala Asp Pro Tyr Xaa Cys
1               5                   10                  15

Ala

<210> SEQ ID NO 198
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 198

Ala Cys Ile Pro Glu Gly Pro Tyr Cys Phe Ala Asp Pro Tyr Xaa Cys
1               5                   10                  15

Ala

<210> SEQ ID NO 199
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents tBuAla
<220> FEATURE:
<221> NAME/KEY: X
<222> LOCATION: (8)..(8)
<223> OTHER INFORMATION: X represents 4MePhe
<220> FEATURE:
<221> NAME/KEY: X
<222> LOCATION: (10)..(10)
<223> OTHER INFORMATION: X represents 4FPhe
<220> FEATURE:
<221> NAME/KEY: X
<222> LOCATION: (15)..(15)
<223> OTHER INFORMATION: X represents Nle

<400> SEQUENCE: 199
```

```
Ala Cys Xaa Pro Glu Phe Pro Xaa Cys Xaa Ala Asp Pro Tyr Xaa Cys
1               5                   10                  15

Ala

<210> SEQ ID NO 200
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents tBuAla
<220> FEATURE:
<221> NAME/KEY: X
<222> LOCATION: (8)..(8)
<223> OTHER INFORMATION: X represents 4MePhe
<220> FEATURE:
<221> NAME/KEY: X
<222> LOCATION: (10)..(10)
<223> OTHER INFORMATION: X represents 4FPhe
<220> FEATURE:
<221> NAME/KEY: X
<222> LOCATION: (15)..(15)
<223> OTHER INFORMATION: X represents Nle

<400> SEQUENCE: 200

Ala Cys Xaa Pro Glu Phe Gln Xaa Cys Xaa Ala Asp Pro Tyr Xaa Cys
1               5                   10                  15

Ala

<210> SEQ ID NO 201
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents tBuAla
<220> FEATURE:
<221> NAME/KEY: X
<222> LOCATION: (8)..(8)
<223> OTHER INFORMATION: X represents 4MePhe
<220> FEATURE:
<221> NAME/KEY: X
<222> LOCATION: (10)..(10)
<223> OTHER INFORMATION: X represents 4FPhe
<220> FEATURE:
<221> NAME/KEY: X
<222> LOCATION: (15)..(15)
<223> OTHER INFORMATION: X represents Nle

<400> SEQUENCE: 201

Ala Cys Xaa Glu Glu Phe Pro Xaa Cys Xaa Ala Asp Pro Tyr Xaa Cys
1               5                   10                  15

Ala

<210> SEQ ID NO 202
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents tBuAla
<220> FEATURE:
```

```
<221> NAME/KEY: X
<222> LOCATION: (8)..(8)
<223> OTHER INFORMATION: X represents 4MePhe
<220> FEATURE:
<221> NAME/KEY: X
<222> LOCATION: (10)..(10)
<223> OTHER INFORMATION: X represents 4FPhe
<220> FEATURE:
<221> NAME/KEY: X
<222> LOCATION: (15)..(15)
<223> OTHER INFORMATION: X represents Nle

<400> SEQUENCE: 202

Ala Cys Xaa Glu Glu Phe Gln Xaa Cys Xaa Ala Asp Pro Tyr Xaa Cys
1               5                   10                  15

Ala

<210> SEQ ID NO 203
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (4)..(4)
<223> OTHER INFORMATION: X represents HyP
<220> FEATURE:
<221> NAME/KEY: X
<222> LOCATION: (15)..(15)
<223> OTHER INFORMATION: X represents Nle

<400> SEQUENCE: 203

Ala Cys Ile Xaa Glu Gly Gln Tyr Cys Phe Ala Asp Pro Tyr Xaa Cys
1               5                   10                  15

Ala

<210> SEQ ID NO 204
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 204

Ala Cys Ile Glu Glu Trp Gln Tyr Cys Phe Ala Asp Pro Tyr Xaa Cys
1               5                   10                  15

Ala

<210> SEQ ID NO 205
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (7)..(7)
<223> OTHER INFORMATION: X represents Aze
<220> FEATURE:
<221> NAME/KEY: X
<222> LOCATION: (15)..(15)
<223> OTHER INFORMATION: X represents Nle

<400> SEQUENCE: 205
```

Ala Cys Ile Glu Glu Gly Xaa Tyr Cys Phe Ala Asp Pro Tyr Xaa Cys
1               5                   10                  15

Ala

<210> SEQ ID NO 206
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (7)..(7)
<223> OTHER INFORMATION: X represents Pip
<220> FEATURE:
<221> NAME/KEY: X
<222> LOCATION: (15)..(15)
<223> OTHER INFORMATION: X represents Nle

<400> SEQUENCE: 206

Ala Cys Ile Glu Glu Gly Xaa Tyr Cys Phe Ala Asp Pro Tyr Xaa Cys
1               5                   10                  15

Ala

<210> SEQ ID NO 207
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represents 2Nal
<220> FEATURE:
<221> NAME/KEY: X
<222> LOCATION: (15)..(15)
<223> OTHER INFORMATION: X represents Nle

<400> SEQUENCE: 207

Ala Cys Ile Glu Glu Gly Gln Xaa Cys Phe Ala Asp Pro Tyr Xaa Cys
1               5                   10                  15

Ala

<210> SEQ ID NO 208
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represents 4MeOPhe
<220> FEATURE:
<221> NAME/KEY: X
<222> LOCATION: (15)..(15)
<223> OTHER INFORMATION: X represents Nle

<400> SEQUENCE: 208

Ala Cys Ile Glu Glu Gly Gln Xaa Cys Phe Ala Asp Pro Tyr Xaa Cys
1               5                   10                  15

Ala

<210> SEQ ID NO 209
<211> LENGTH: 17
<212> TYPE: PRT
<213> ORGANISM: Artificial

```
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 209

Ala Cys Ile Glu Glu Gly Gln Tyr Cys Tyr Ala Asp Pro Tyr Xaa Cys
1               5                   10                  15

Ala

<210> SEQ ID NO 210
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (13)..(13)
<223> OTHER INFORMATION: X represents Aze
<220> FEATURE:
<221> NAME/KEY: X
<222> LOCATION: (15)..(15)
<223> OTHER INFORMATION: X represents Nle

<400> SEQUENCE: 210

Ala Cys Ile Glu Glu Gly Gln Tyr Cys Phe Ala Asp Xaa Tyr Xaa Cys
1               5                   10                  15

Ala

<210> SEQ ID NO 211
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Hse(Me)

<400> SEQUENCE: 211

Ala Cys Ile Glu Glu Gly Gln Tyr Cys Phe Ala Asp Pro Tyr Xaa Cys
1               5                   10                  15

Ala

<210> SEQ ID NO 212
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents NMeIle
<220> FEATURE:
<221> NAME/KEY: X
<222> LOCATION: (15)..(15)
<223> OTHER INFORMATION: X represents Nle

<400> SEQUENCE: 212

Ala Cys Xaa Glu Glu Gly Gln Tyr Cys Phe Ala Asp Pro Tyr Xaa Cys
1               5                   10                  15

Ala
```

```
<210> SEQ ID NO 213
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (4)..(4)
<223> OTHER INFORMATION: X represents Aze
<220> FEATURE:
<221> NAME/KEY: X
<222> LOCATION: (15)..(15)
<223> OTHER INFORMATION: X represents Nle

<400> SEQUENCE: 213

Ala Cys Ile Xaa Glu Gly Gln Tyr Cys Phe Ala Asp Pro Tyr Xaa Cys
1               5                   10                  15
Ala

<210> SEQ ID NO 214
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (4)..(4)
<223> OTHER INFORMATION: X represents Pip
<220> FEATURE:
<221> NAME/KEY: X
<222> LOCATION: (15)..(15)
<223> OTHER INFORMATION: X represents Nle

<400> SEQUENCE: 214

Ala Cys Ile Xaa Glu Gly Gln Tyr Cys Phe Ala Asp Pro Tyr Xaa Cys
1               5                   10                  15
Ala

<210> SEQ ID NO 215
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (4)..(4)
<223> OTHER INFORMATION: X represents NMeGlu
<220> FEATURE:
<221> NAME/KEY: X
<222> LOCATION: (15)..(15)
<223> OTHER INFORMATION: X represents Nle

<400> SEQUENCE: 215

Ala Cys Ile Xaa Glu Gly Gln Tyr Cys Phe Ala Asp Pro Tyr Xaa Cys
1               5                   10                  15
Ala

<210> SEQ ID NO 216
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (5)..(5)
```

```
<223> OTHER INFORMATION: X represents NMeGlu
<220> FEATURE:
<221> NAME/KEY: X
<222> LOCATION: (15)..(15)
<223> OTHER INFORMATION: X represents Nle

<400> SEQUENCE: 216

Ala Cys Ile Glu Xaa Gly Gln Tyr Cys Phe Ala Asp Pro Tyr Xaa Cys
1               5                   10                  15

Ala

<210> SEQ ID NO 217
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 217

Ala Cys Ile Glu Glu Asp Gln Tyr Cys Phe Ala Asp Pro Tyr Xaa Cys
1               5                   10                  15

Ala

<210> SEQ ID NO 218
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (7)..(7)
<223> OTHER INFORMATION: X represents NMeAla
<220> FEATURE:
<221> NAME/KEY: X
<222> LOCATION: (15)..(15)
<223> OTHER INFORMATION: X represents Nle

<400> SEQUENCE: 218

Ala Cys Ile Glu Glu Gly Xaa Tyr Cys Phe Ala Asp Pro Tyr Xaa Cys
1               5                   10                  15

Ala

<210> SEQ ID NO 219
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represents NMeTyr
<220> FEATURE:
<221> NAME/KEY: X
<222> LOCATION: (15)..(15)
<223> OTHER INFORMATION: X represents Nle

<400> SEQUENCE: 219

Ala Cys Ile Glu Glu Gly Gln Xaa Cys Phe Ala Asp Pro Tyr Xaa Cys
1               5                   10                  15

Ala
```

```
<210> SEQ ID NO 220
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represents HPhe
<220> FEATURE:
<221> NAME/KEY: X
<222> LOCATION: (15)..(15)
<223> OTHER INFORMATION: X represents Nle

<400> SEQUENCE: 220

Ala Cys Ile Glu Glu Gly Gln Xaa Cys Phe Ala Asp Pro Tyr Xaa Cys
1               5                   10                  15
Ala

<210> SEQ ID NO 221
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represents 2Pal
<220> FEATURE:
<221> NAME/KEY: X
<222> LOCATION: (15)..(15)
<223> OTHER INFORMATION: X represents Nle

<400> SEQUENCE: 221

Ala Cys Ile Glu Glu Gly Gln Xaa Cys Phe Ala Asp Pro Tyr Xaa Cys
1               5                   10                  15
Ala

<210> SEQ ID NO 222
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represents 3Pal
<220> FEATURE:
<221> NAME/KEY: X
<222> LOCATION: (15)..(15)
<223> OTHER INFORMATION: X represents Nle

<400> SEQUENCE: 222

Ala Cys Ile Glu Glu Gly Gln Xaa Cys Phe Ala Asp Pro Tyr Xaa Cys
1               5                   10                  15
Ala

<210> SEQ ID NO 223
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represents 4,4-BPA
```

```
<220> FEATURE:
<221> NAME/KEY: X
<222> LOCATION: (15)..(15)
<223> OTHER INFORMATION: X represents Nle

<400> SEQUENCE: 223

Ala Cys Ile Glu Glu Gly Gln Xaa Cys Phe Ala Asp Pro Tyr Xaa Cys
1               5                   10                  15
Ala

<210> SEQ ID NO 224
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents HPhe
<220> FEATURE:
<221> NAME/KEY: X
<222> LOCATION: (15)..(15)
<223> OTHER INFORMATION: X represents Nle

<400> SEQUENCE: 224

Ala Cys Ile Glu Glu Gly Gln Tyr Cys Xaa Ala Asp Pro Tyr Xaa Cys
1               5                   10                  15
Ala

<210> SEQ ID NO 225
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents 2Pal
<220> FEATURE:
<221> NAME/KEY: X
<222> LOCATION: (15)..(15)
<223> OTHER INFORMATION: X represents Nle

<400> SEQUENCE: 225

Ala Cys Ile Glu Glu Gly Gln Tyr Cys Xaa Ala Asp Pro Tyr Xaa Cys
1               5                   10                  15
Ala

<210> SEQ ID NO 226
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents 3Pal
<220> FEATURE:
<221> NAME/KEY: X
<222> LOCATION: (15)..(15)
<223> OTHER INFORMATION: X represents Nle

<400> SEQUENCE: 226

Ala Cys Ile Glu Glu Gly Gln Tyr Cys Xaa Ala Asp Pro Tyr Xaa Cys
1               5                   10                  15
```

Ala

<210> SEQ ID NO 227
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents 4Pal
<220> FEATURE:
<221> NAME/KEY: X
<222> LOCATION: (15)..(15)
<223> OTHER INFORMATION: X represents Nle

<400> SEQUENCE: 227

Ala Cys Ile Glu Glu Gly Gln Tyr Cys Xaa Ala Asp Pro Tyr Xaa Cys
1               5                   10                  15

Ala

<210> SEQ ID NO 228
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents 4,4-BPA
<220> FEATURE:
<221> NAME/KEY: X
<222> LOCATION: (15)..(15)
<223> OTHER INFORMATION: X represents Nle

<400> SEQUENCE: 228

Ala Cys Ile Glu Glu Gly Gln Tyr Cys Xaa Ala Asp Pro Tyr Xaa Cys
1               5                   10                  15

Ala

<210> SEQ ID NO 229
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents 1Nal
<220> FEATURE:
<221> NAME/KEY: X
<222> LOCATION: (15)..(15)
<223> OTHER INFORMATION: X represents Nle

<400> SEQUENCE: 229

Ala Cys Ile Glu Glu Gly Gln Tyr Cys Xaa Ala Asp Pro Tyr Xaa Cys
1               5                   10                  15

Ala

<210> SEQ ID NO 230
<211> LENGTH: 17
<212> TYPE: PRT
<213> ORGANISM: Artificial
<220> FEATURE:
<223> OTHER INFORMATION: Synthetic Peptide
<220> FEATURE:

```
<221> NAME/KEY: X
<222> LOCATION: (10)..(10)
<223> OTHER INFORMATION: X represents 4tBuPhe
<220> FEATURE:
<221> NAME/KEY: X
<222> LOCATION: (15)..(15)
<223> OTHER INFORMATION: X represents Nle

<400> SEQUENCE: 230

Ala Cys Ile Glu Glu Gly Gln Tyr Cys Xaa Ala Asp Pro Tyr Xaa Cys
1               5                   10                  15
Ala

<210> SEQ ID NO 231
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (11)..(11)
<223> OTHER INFORMATION: X represents NMeAla
<220> FEATURE:
<221> NAME/KEY: X
<222> LOCATION: (15)..(15)
<223> OTHER INFORMATION: X represents Nle

<400> SEQUENCE: 231

Ala Cys Ile Glu Glu Gly Gln Tyr Cys Phe Xaa Asp Pro Tyr Xaa Cys
1               5                   10                  15
Ala

<210> SEQ ID NO 232
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (7)..(7)
<223> OTHER INFORMATION: X represents 5,5-dmP
<220> FEATURE:
<221> NAME/KEY: X
<222> LOCATION: (15)..(15)
<223> OTHER INFORMATION: X represents Nle

<400> SEQUENCE: 232

Ala Cys Ile Glu Glu Gly Xaa Tyr Cys Phe Ala Asp Pro Tyr Xaa Cys
1               5                   10                  15
Ala

<210> SEQ ID NO 233
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (13)..(13)
<223> OTHER INFORMATION: X represents HyP
<220> FEATURE:
<221> NAME/KEY: X
<222> LOCATION: (15)..(15)
<223> OTHER INFORMATION: X represents Nle

<400> SEQUENCE: 233
```

```
Ala Cys Ile Glu Glu Gly Gln Tyr Cys Phe Ala Asp Xaa Tyr Xaa Cys
1               5                   10                  15
Ala
```

<210> SEQ ID NO 234
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (7)..(7)
<223> OTHER INFORMATION: X represents Oic
<220> FEATURE:
<221> NAME/KEY: X
<222> LOCATION: (15)..(15)
<223> OTHER INFORMATION: X represents Nle

<400> SEQUENCE: 234

```
Ala Cys Ile Glu Glu Gly Xaa Tyr Cys Phe Ala Asp Pro Tyr Xaa Cys
1               5                   10                  15
Ala
```

<210> SEQ ID NO 235
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (13)..(13)
<223> OTHER INFORMATION: X represents Oic
<220> FEATURE:
<221> NAME/KEY: X
<222> LOCATION: (15)..(15)
<223> OTHER INFORMATION: X represents Nle

<400> SEQUENCE: 235

```
Ala Cys Ile Glu Glu Gly Gln Tyr Cys Phe Ala Asp Xaa Tyr Xaa Cys
1               5                   10                  15
Ala
```

<210> SEQ ID NO 236
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (4)..(4)
<223> OTHER INFORMATION: X represents Oic
<220> FEATURE:
<221> NAME/KEY: X
<222> LOCATION: (15)..(15)
<223> OTHER INFORMATION: X represents Nle

<400> SEQUENCE: 236

```
Ala Cys Ile Xaa Glu Gly Gln Tyr Cys Phe Ala Asp Pro Tyr Xaa Cys
1               5                   10                  15
Ala
```

<210> SEQ ID NO 237
<211> LENGTH: 17
<212> TYPE: PRT
<213> ORGANISM: Artificial

```
<220> FEATURE:
<223> OTHER INFORMATION: Synthetic Peptide
<220> FEATURE:
<221> NAME/KEY: X
<222> LOCATION: (13)..(13)
<223> OTHER INFORMATION: X represents Oxa
<220> FEATURE:
<221> NAME/KEY: X
<222> LOCATION: (15)..(15)
<223> OTHER INFORMATION: X represents Nle

<400> SEQUENCE: 237

Ala Cys Ile Glu Glu Gly Gln Tyr Cys Phe Ala Asp Xaa Tyr Xaa Cys
1               5                   10                  15
Ala

<210> SEQ ID NO 238
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (4)..(4)
<223> OTHER INFORMATION: X represents Oxa
<220> FEATURE:
<221> NAME/KEY: X
<222> LOCATION: (15)..(15)
<223> OTHER INFORMATION: X represents Nle

<400> SEQUENCE: 238

Ala Cys Ile Xaa Glu Gly Gln Tyr Cys Phe Ala Asp Pro Tyr Xaa Cys
1               5                   10                  15
Ala

<210> SEQ ID NO 239
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (7)..(7)
<223> OTHER INFORMATION: X represents Oxa
<220> FEATURE:
<221> NAME/KEY: X
<222> LOCATION: (15)..(15)
<223> OTHER INFORMATION: X represents Nle

<400> SEQUENCE: 239

Ala Cys Ile Glu Glu Gly Xaa Tyr Cys Phe Ala Asp Pro Tyr Xaa Cys
1               5                   10                  15
Ala

<210> SEQ ID NO 240
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 240

Ala Cys Ile Pro Glu Gly Pro Tyr Cys Phe Ala Asp Pro Tyr Xaa Cys
```

```
1               5                  10                 15

Ala

<210> SEQ ID NO 241
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (7)..(7)
<223> OTHER INFORMATION: X represents HyP
<220> FEATURE:
<221> NAME/KEY: X
<222> LOCATION: (15)..(15)
<223> OTHER INFORMATION: X represents Nle

<400> SEQUENCE: 241

Ala Cys Ile Glu Glu Gly Xaa Tyr Cys Phe Ala Asp Pro Tyr Xaa Cys
1               5                  10                 15

Ala

<210> SEQ ID NO 242
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 242

Ala Cys Ile Pro Glu Ala Pro Tyr Cys Phe Ala Asp Pro Tyr Xaa Cys
1               5                  10                 15

Ala

<210> SEQ ID NO 243
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents tBuAla
<220> FEATURE:
<221> NAME/KEY: X
<222> LOCATION: (15)..(15)
<223> OTHER INFORMATION: X represents Nle

<400> SEQUENCE: 243

Ala Cys Xaa Pro Glu Ala Pro Tyr Cys Phe Ala Asp Pro Tyr Xaa Cys
1               5                  10                 15

Ala

<210> SEQ ID NO 244
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
```

<223> OTHER INFORMATION: X represents Nle

<400> SEQUENCE: 244

Ala Cys Ile Glu Glu Gly Gln Tyr Cys Phe Ala Asp Pro Tyr Xaa Cys
1               5                   10                  15
Ala

<210> SEQ ID NO 245
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents tBuAla
<220> FEATURE:
<221> NAME/KEY: X
<222> LOCATION: (15)..(15)
<223> OTHER INFORMATION: X represents Nle

<400> SEQUENCE: 245

Ala Cys Xaa Glu Glu Gly Gln Tyr Cys Phe Ala Asp Pro Tyr Xaa Cys
1               5                   10                  15
Ala

<210> SEQ ID NO 246
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents Chg
<220> FEATURE:
<221> NAME/KEY: X
<222> LOCATION: (15)..(15)
<223> OTHER INFORMATION: X represents Nle

<400> SEQUENCE: 246

Ala Cys Xaa Glu Glu Gly Gln Tyr Cys Phe Ala Asp Pro Tyr Xaa Cys
1               5                   10                  15
Ala

<210> SEQ ID NO 247
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents Ac5c
<220> FEATURE:
<221> NAME/KEY: X
<222> LOCATION: (15)..(15)
<223> OTHER INFORMATION: X represents Nle

<400> SEQUENCE: 247

Ala Cys Xaa Glu Glu Gly Gln Tyr Cys Phe Ala Asp Pro Tyr Xaa Cys
1               5                   10                  15
Ala

```
<210> SEQ ID NO 248
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 248

Ala Cys Ile Pro Glu Gly Gln Tyr Cys Phe Ala Asp Pro Tyr Xaa Cys
1               5                   10                  15

Ala

<210> SEQ ID NO 249
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 249

Ala Cys Ile Gln Glu Gly Gln Tyr Cys Phe Ala Asp Pro Tyr Xaa Cys
1               5                   10                  15

Ala

<210> SEQ ID NO 250
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 250

Ala Cys Ile Glu Pro Gly Gln Tyr Cys Phe Ala Asp Pro Tyr Xaa Cys
1               5                   10                  15

Ala

<210> SEQ ID NO 251
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 251

Ala Cys Ile Glu Gln Gly Gln Tyr Cys Phe Ala Asp Pro Tyr Xaa Cys
1               5                   10                  15

Ala

<210> SEQ ID NO 252
<211> LENGTH: 17
<212> TYPE: PRT
```

```
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 252

Ala Cys Ile Glu Glu Phe Gln Tyr Cys Phe Ala Asp Pro Tyr Xaa Cys
1               5                   10                  15

Ala

<210> SEQ ID NO 253
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 253

Ala Cys Ile Glu Glu Ala Gln Tyr Cys Phe Ala Asp Pro Tyr Xaa Cys
1               5                   10                  15

Ala

<210> SEQ ID NO 254
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (6)..(6)
<223> OTHER INFORMATION: X represents Ac5c
<220> FEATURE:
<221> NAME/KEY: X
<222> LOCATION: (15)..(15)
<223> OTHER INFORMATION: X represents Nle

<400> SEQUENCE: 254

Ala Cys Ile Glu Glu Xaa Gln Tyr Cys Phe Ala Asp Pro Tyr Xaa Cys
1               5                   10                  15

Ala

<210> SEQ ID NO 255
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 255

Ala Cys Ile Glu Glu Gly Ala Tyr Cys Phe Ala Asp Pro Tyr Xaa Cys
1               5                   10                  15

Ala

<210> SEQ ID NO 256
<211> LENGTH: 17
```

```
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (7)..(7)
<223> OTHER INFORMATION: X represents Aib
<220> FEATURE:
<221> NAME/KEY: X
<222> LOCATION: (15)..(15)
<223> OTHER INFORMATION: X represents Nle

<400> SEQUENCE: 256

Ala Cys Ile Glu Glu Gly Xaa Tyr Cys Phe Ala Asp Pro Tyr Xaa Cys
1               5                   10                  15

Ala

<210> SEQ ID NO 257
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (7)..(7)
<223> OTHER INFORMATION: X represents Ac5c
<220> FEATURE:
<221> NAME/KEY: X
<222> LOCATION: (15)..(15)
<223> OTHER INFORMATION: X represents Nle

<400> SEQUENCE: 257

Ala Cys Ile Glu Glu Gly Xaa Tyr Cys Phe Ala Asp Pro Tyr Xaa Cys
1               5                   10                  15

Ala

<210> SEQ ID NO 258
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represents 4MePhe
<220> FEATURE:
<221> NAME/KEY: X
<222> LOCATION: (15)..(15)
<223> OTHER INFORMATION: X represents Nle

<400> SEQUENCE: 258

Ala Cys Ile Glu Glu Gly Gln Xaa Cys Phe Ala Asp Pro Tyr Xaa Cys
1               5                   10                  15

Ala

<210> SEQ ID NO 259
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represnets 1Nal
<220> FEATURE:
<221> NAME/KEY: X
```

```
<222> LOCATION: (15)..(15)
<223> OTHER INFORMATION: X represnets Nle

<400> SEQUENCE: 259

Ala Cys Ile Glu Glu Gly Gln Xaa Cys Phe Ala Asp Pro Tyr Xaa Cys
1               5                   10                  15
Ala

<210> SEQ ID NO 260
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents 2Nal
<220> FEATURE:
<221> NAME/KEY: X
<222> LOCATION: (15)..(15)
<223> OTHER INFORMATION: X represents Nle

<400> SEQUENCE: 260

Ala Cys Ile Glu Glu Gly Gln Tyr Cys Xaa Ala Asp Pro Tyr Xaa Cys
1               5                   10                  15
Ala

<210> SEQ ID NO 261
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents NO2Phe
<220> FEATURE:
<221> NAME/KEY: X
<222> LOCATION: (15)..(15)
<223> OTHER INFORMATION: X represents Nle

<400> SEQUENCE: 261

Ala Cys Ile Glu Glu Gly Gln Tyr Cys Xaa Ala Asp Pro Tyr Xaa Cys
1               5                   10                  15
Ala

<210> SEQ ID NO 262
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents 4BrPhe
<220> FEATURE:
<221> NAME/KEY: X
<222> LOCATION: (15)..(15)
<223> OTHER INFORMATION: X represents Nle

<400> SEQUENCE: 262

Ala Cys Ile Glu Glu Gly Gln Tyr Cys Xaa Ala Asp Pro Tyr Xaa Cys
1               5                   10                  15
Ala
```

```
<210> SEQ ID NO 263
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (11)..(11)
<223> OTHER INFORMATION: X represents Abu
<220> FEATURE:
<221> NAME/KEY: X
<222> LOCATION: (15)..(15)
<223> OTHER INFORMATION: X represents Nle

<400> SEQUENCE: 263

Ala Cys Ile Glu Glu Gly Gln Tyr Cys Phe Xaa Asp Pro Tyr Xaa Cys
1               5                   10                  15
Ala

<210> SEQ ID NO 264
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Ahp

<400> SEQUENCE: 264

Ala Cys Ile Glu Glu Gly Gln Tyr Cys Phe Ala Asp Pro Tyr Xaa Cys
1               5                   10                  15
Ala

<210> SEQ ID NO 265
<211> LENGTH: 17
<212> TYPE: PRT
<213> ORGANISM: Artificial
<220> FEATURE:
<223> OTHER INFORMATION: Synthetic Peptide

<400> SEQUENCE: 265

Ala Cys Ile Glu Glu Gly Gln Tyr Cys Phe Ala Asp Pro Tyr Met Cys
1               5                   10                  15
Ala

<210> SEQ ID NO 266
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (2)..(2)
<223> OTHER INFORMATION: X represents Ile, tBuAla or Chg
<220> FEATURE:
<221> NAME/KEY: X
<222> LOCATION: (3)..(3)
<223> OTHER INFORMATION: X represents Glu, Pro, Asp, Lys, Aad, HyP or
      Oxa
<220> FEATURE:
<221> NAME/KEY: X
<222> LOCATION: (4)..(4)
<223> OTHER INFORMATION: X represents Glu, Lys or Aad
<220> FEATURE:
<221> NAME/KEY: X
```

```
<222> LOCATION: (5)..(5)
<223> OTHER INFORMATION: X represents Gly, D-Lys, D-Ala, L-Ala, D-Phe,
      D-Glu, D-Gln, D-Leu, D-Ser or D-Trp
<220> FEATURE:
<221> NAME/KEY: X
<222> LOCATION: (6)..(6)
<223> OTHER INFORMATION: X represents Gln, Lys, Ala, Pro, 5,5-dmP, Oic,
      Oxa, HyP, Aib or Ac5c
<220> FEATURE:
<221> NAME/KEY: X
<222> LOCATION: (7)..(7)
<223> OTHER INFORMATION: X represents Tyr, Phe, 3MeF, 4MeF, 4FF, 2Nal,
      4MeOPhe or 4,4BPA
<220> FEATURE:
<221> NAME/KEY: X
<222> LOCATION: (9)..(9)
<223> OTHER INFORMATION: X represents Phe, Lys, 4MeF, 4FF, 2FPhe, 4FPhe,
      4Pal, 4,4BPA, 4tBuPhe, NO2Phe or 4BrPhe
<220> FEATURE:
<221> NAME/KEY: X
<222> LOCATION: (10)..(10)
<223> OTHER INFORMATION: X represents Ala or Lys
<220> FEATURE:
<221> NAME/KEY: X
<222> LOCATION: (12)..(12)
<223> OTHER INFORMATION: X represents Pro or Lys
<220> FEATURE:
<221> NAME/KEY: X
<222> LOCATION: (13)..(13)
<223> OTHER INFORMATION: X represents Tyr or Lys
<220> FEATURE:
<221> NAME/KEY: X
<222> LOCATION: (14)..(14)
<223> OTHER INFORMATION: X represents Met, Lys, Nle, HLeu or Ahp

<400> SEQUENCE: 266

Cys Xaa Xaa Xaa Xaa Xaa Xaa Cys Xaa Xaa Asp Xaa Xaa Xaa Cys
1               5                   10                  15

<210> SEQ ID NO 267
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (2)..(2)
<223> OTHER INFORMATION: X represents Ile or tBuAla
<220> FEATURE:
<221> NAME/KEY: X
<222> LOCATION: (3)..(3)
<223> OTHER INFORMATION: X represents Lys, Glu or Pro
<220> FEATURE:
<221> NAME/KEY: X
<222> LOCATION: (4)..(4)
<223> OTHER INFORMATION: X represents Glu or D-Lys
<220> FEATURE:
<221> NAME/KEY: X
<222> LOCATION: (5)..(5)
<223> OTHER INFORMATION: X represents Gly, D-Lys, D-Phe or D-Ala
<220> FEATURE:
<221> NAME/KEY: X
<222> LOCATION: (6)..(6)
<223> OTHER INFORMATION: X represents Gln, Lys or Pro
<220> FEATURE:
<221> NAME/KEY: X
<222> LOCATION: (7)..(7)
<223> OTHER INFORMATION: X represents Tyr or 4MePhe
<220> FEATURE:
<221> NAME/KEY: X
<222> LOCATION: (9)..(9)
<223> OTHER INFORMATION: X represents Phe or 4FPhe
<220> FEATURE:
<221> NAME/KEY: X
<222> LOCATION: (14)..(14)
<223> OTHER INFORMATION: X represents Met or Nle
```

```
<400> SEQUENCE: 267

Cys Xaa Xaa Xaa Xaa Xaa Xaa Cys Xaa Ala Asp Pro Tyr Xaa Cys
1               5                   10                  15
```

BICYCLIC PEPTIDE LIGAND SPECIFIC FOR CD137

FIELD OF THE INVENTION

The present invention relates to polypeptides which are covalently bound to molecular scaffolds such that two or more peptide loops are subtended between attachment points to the scaffold. In particular, the invention describes peptides which are high affinity binders of CD137. The invention also includes drug conjugates comprising said peptides, conjugated to one or more effector and/or functional groups, to pharmaceutical compositions comprising said peptide ligands and drug conjugates and to the use of said peptide ligands and drug conjugates in preventing, suppressing or treating a disease or disorder mediated by CD137.

BACKGROUND OF THE INVENTION

Cyclic peptides are able to bind with high affinity and target specificity to protein targets and hence are an attractive molecule class for the development of therapeutics. In fact, several cyclic peptides are already successfully used in the clinic, as for example the antibacterial peptide vancomycin, the immunosuppressant drug cyclosporine or the anti-cancer drug octreotide (Driggers et al. (2008), Nat Rev Drug Discov 7 (7), 608-24). Good binding properties result from a relatively large interaction surface formed between the peptide and the target as well as the reduced conformational flexibility of the cyclic structures. Typically, macrocycles bind to surfaces of several hundred-square angstrom, as for example the cyclic peptide CXCR4 antagonist $CVX_{15}$ (400 Å$^2$; Wu et al. (2007), Science 330, 1066-71), a cyclic peptide with the Arg-Gly-Asp motif binding to integrin αVb3 (355 Å$^2$) (Xiong et al. (2002), Science 296 (5565), 151-5) or the cyclic peptide inhibitor upain-1 binding to urokinase-type plasminogen activator (603 Å$^2$; Zhao et al. (2007), J Struct Biol 160 (1), 1-10).

Due to their cyclic configuration, peptide macrocycles are less flexible than linear peptides, leading to a smaller loss of entropy upon binding to targets and resulting in a higher binding affinity. The reduced flexibility also leads to locking target-specific conformations, increasing binding specificity compared to linear peptides. This effect has been exemplified by a potent and selective inhibitor of matrix metalloproteinase 8 (MMP-8) which lost its selectivity over other MMPs when its ring was opened (Cherney et al. (1998), J Med Chem 41 (11), 1749-51). The favourable binding properties achieved through macrocyclization are even more pronounced in multicyclic peptides having more than one peptide ring as for example in vancomycin, nisin and actinomycin.

Different research teams have previously tethered polypeptides with cysteine residues to a synthetic molecular structure (Kemp and McNamara (1985), J. Org. Chem; Timmerman et al. (2005), ChemBioChem). Meloen and co-workers had used tris(bromomethyl)benzene and related molecules for rapid and quantitative cyclisation of multiple peptide loops onto synthetic scaffolds for structural mimicry of protein surfaces (Timmerman et al. (2005), ChemBioChem). Methods for the generation of candidate drug compounds wherein said compounds are generated by linking cysteine containing polypeptides to a molecular scaffold as for example tris(bromomethyl)benzene are disclosed in WO 2004/077062 and WO 2006/078161.

Phage display-based combinatorial approaches have been developed to generate and screen large libraries of bicyclic peptides to targets of interest (Heinis et al. (2009), Nat Chem Biol 5 (7), 502-7 and WO2009/098450). Briefly, combinatorial libraries of linear peptides containing three cysteine residues and two regions of six random amino acids (Cys-$(Xaa)_6$-Cys-$(Xaa)_6$-Cys) were displayed on phage and cyclised by covalently linking the cysteine side chains to a small molecule (tris-(bromomethyl)benzene).

SUMMARY OF THE INVENTION

According to a first aspect of the invention, there is provided a peptide ligand specific for CD137 comprising a polypeptide comprising at least three reactive groups, separated by at least two loop sequences, and a molecular scaffold which forms covalent bonds with the reactive groups of the polypeptide such that at least two polypeptide loops are formed on the molecular scaffold.

According to a further aspect of the invention, there is provided a drug conjugate comprising a peptide ligand as defined herein conjugated to one or more effector and/or functional groups.

According to a further aspect of the invention, there is provided a pharmaceutical composition comprising a peptide ligand or a drug conjugate as defined herein in combination with one or more pharmaceutically acceptable excipients.

According to a further aspect of the invention, there is provided a peptide ligand or drug conjugate as defined herein for use in preventing, suppressing or treating a disease or disorder mediated by CD137.

DETAILED DESCRIPTION OF THE INVENTION

Figure 1:
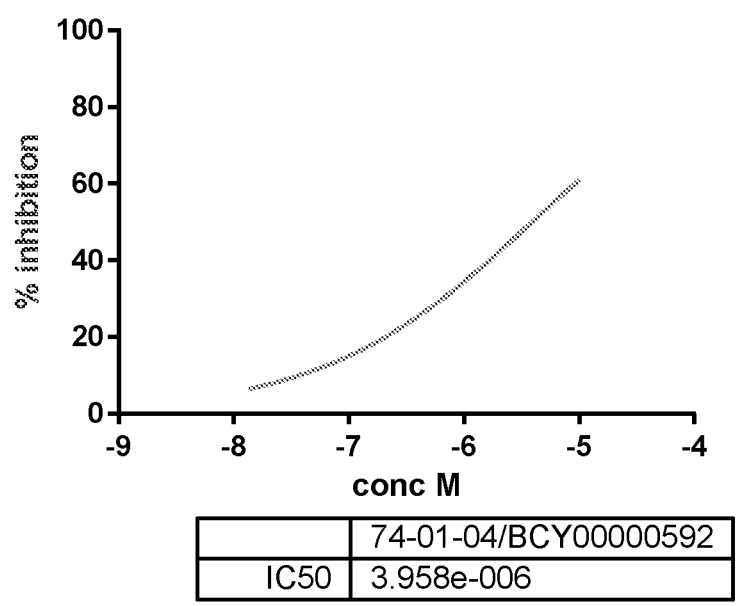
FIG. 1: Results of CD137 cell activity assay using bicyclic peptide BCY592.

According to one particular aspect of the invention which may be mentioned, there is provided a peptide ligand specific for CD137 comprising a polypeptide comprising at least three cysteine residues, separated by at least two loop sequences, and a molecular scaffold which forms covalent bonds with the cysteine residues of the polypeptide such that at least two polypeptide loops are formed on the molecular scaffold.

In one embodiment, said loop sequences comprise 5 or 6 amino acid acids.

In a further embodiment, said peptide ligand comprises three cysteine residues separated by two loop sequences both of which consist of 6 amino acids.

In a further embodiment, said peptide ligand comprises three cysteine residues separated by two loop sequences one of which consists of 5 amino acids and the other of which consists of 6 amino acids.

In one embodiment, said peptide ligand comprises an amino acid sequence selected from:

$C_i$-I-E-E-G-Q-Y-$C_{ii}$-$X_1$-$X_2$-D-$X_3$-Y/Q/M-$X_4$-$C_{iii}$; (SEQ ID NO: 20)

$C_i$-D-I-G-P-P-Y-$C_{ii}$-Y-R/A-D-M/P-Y-M-$C_{iii}$; (SEQ ID NO: 21)

$C_i$-D-E-W-G-L-F/Y-$C_{ii}$-I/F-P/A-H-S/P-D-$C_{iii}$; (SEQ ID NO: 22)
and $C_i$IEPGPFC$_{ii}$YADPYMC$_{iii}$; (SEQ ID NO: 19)

wherein $X_1$-$X_4$ represent any amino acid residue and $C_i$, $C_{ii}$ and $C_{iii}$ represent first, second and third cysteine residues, respectively or a pharmaceutically acceptable salt thereof.

An Alanine scanning experiment was conducted on selected peptides of the invention. An Alanine scan is used to predict which amino acids positions are most amenable to substitutions and further optimisation of affinity and/or other desirable properties. The Alanine scan peptides were characterized into three categories based on affinity relative to the parental peptide sequence (BCY7151; SEQ ID NO: 92): 1. no loss in affinity 2. 2-10 fold weaker affinity and 3. >10 fold weaker affinity. Peptides in category 1 and category 2 can undergo extensive SAR testing with alternative amino acid substitutions. The peptides in category 3 were kept fixed or only substituted with highly similar amino acids. The results of the Alanine scan are shown in Table 2 wherein it can be seen that the Aspartic Acid (D) amino acid residue at position 9 is most important for binding because replacement of this amino acid residue with an Alanine residue eliminated binding activity.

A D-Alanine scanning experiment was also conducted on selected peptides of the invention. The default preparation of all bicyclic peptides is in the L-configuration, therefore, the D-Alanine scan shows which amino acid positions are amenable to D-amino acid substitutions. The results of the D-Alanine scan are shown in Table 2 wherein it can be seen that replacing the position 4 Glycine (G) with D-Ala improved affinity relative to the reference peptide. This implies that the D-Ala4 peptide (BCY7297; SEQ ID NO: 106) is important, since it provides improved affinity as well as other advantages associated with non-natural D isomer amino acids.

In one embodiment, said peptide ligand comprises three cysteine residues separated by two loop sequences both of which consist of 6 amino acids, and said peptide ligand comprises an amino acid sequence selected from:

$C_i$-I-E-E-G-Q-Y-$C_{ii}$-$X_1$-$X_2$-D-$X_3$-Y/Q/M-$X_4$-$C_{iii}$; (SEQ ID NO: 20)

$C_i$-D-I-G-P-P-Y-$C_{ii}$-Y-R/A-D-M/P-Y-M-$C_{iii}$; (SEQ ID NO: 21)
and $C_i$IEPGPFC$_{ii}$YADPYMC$_{iii}$; (SEQ ID NO: 19)

wherein $X_1$-$X_4$ represent any amino acid residue and $C_i$, $C_{ii}$ and $C_{iii}$ represent first, second and third cysteine residues, respectively or a pharmaceutically acceptable salt thereof.

In one embodiment, $X_1$ is selected from Y, F and H.
In one embodiment, $X_2$ is selected from R, A and S.
In one embodiment, $X_3$ is selected from M, P and H.
In one embodiment, $X_4$ is selected from M, Y, L and F.
In one embodiment, said peptide ligand comprises three cysteine residues separated by two loop sequences the first of which consists of 6 amino acids and the second of which consists of 5 amino acids, and said peptide ligand comprises an amino acid sequence which is:

$C_i$-D-E-W-G-L-F/Y-$C_{ii}$-I/F-P/A-H-S/P-D-$C_{iii}$; (SEQ ID NO: 22)

wherein $C_i$, $C_{ii}$ and $C_{iii}$ represent first, second and third cysteine residues, respectively or a pharmaceutically acceptable salt thereof.

In a further embodiment, the peptide ligand of $C_i$-I-E-E-G-Q-Y-$C_{ii}$-$X_1$-$X_2$-D-$X_3$-Y/Q/M-$X_4$-$C_{iii}$ (SEQ ID NO: 20) comprises an amino acid sequence selected from any one of SEQ ID NOS: 1-14:

$C_i$IEEGQYC$_{ii}$YRDMYMC$_{iii}$; (SEQ ID NO: 1)

$C_i$IEEGQYC$_{ii}$YADPYMC$_{iii}$; (SEQ ID NO: 2)

$C_i$IEEGQYC$_{ii}$YADPYYC$_{iii}$; (SEQ ID NO: 3)

$C_i$IEEGQYC$_{ii}$YSDPYYC$_{iii}$; (SEQ ID NO: 4)

$C_i$IEEGQYC$_{ii}$FADPYMC$_{iii}$; (SEQ ID NO: 5)

$C_i$IEEGQYC$_{ii}$YADHQLC$_{iii}$; (SEQ ID NO: 6)

$C_i$IEEGQYC$_{ii}$HADPYYC$_{iii}$; (SEQ ID NO: 7)

$C_i$IEEGQYC$_{ii}$HADPYFC$_{iii}$; (SEQ ID NO: 8)

$C_i$IEEGQYC$_{ii}$YADHYMC$_{iii}$; (SEQ ID NO: 9)

$C_i$IEEGQYC$_{ii}$YADPYLC$_{iii}$; (SEQ ID NO: 10)

$C_i$IEEGQYC$_{ii}$YSDPYLC$_{iii}$; (SEQ ID NO: 11)

$C_i$IEEGQYC$_{ii}$FADPYLC$_{iii}$; (SEQ ID NO: 12)

$C_i$IEEGQYC$_{ii}$HADPYMC$_{iii}$; (SEQ ID NO: 13)
and $C_i$IEEGQYC$_{ii}$HADPQMC$_{iii}$; (SEQ ID NO: 14)

wherein $C_i$, $C_{ii}$ and $C_{iii}$ represent first, second and third cysteine residues, respectively, or a pharmaceutically acceptable salt thereof.

In a further embodiment, the peptide ligand of $C_i$-I-E-E-G-Q-Y-$C_{ii}$-$X_1$-$X_2$-D-$X_3$-Y/Q/M-$X_4$-$C_{iii}$ (SEQ ID NO: 20) comprises an amino acid sequence selected from:
  A-(SEQ ID NO: 1)-A (herein referred to as 74-01-00-N004);
  A-(SEQ ID NO: 2)-A (herein referred to as 74-01-01-N001);
  A-(SEQ ID NO: 3)-A (herein referred to as 74-01-02-N001);
  A-(SEQ ID NO: 4)-A (herein referred to as 74-01-03-N001);
  A-(SEQ ID NO: 5)-A (herein referred to as 74-01-04-N001);

A-(SEQ ID NO: 6)-A (herein referred to as 74-01-05-N001);

A-(SEQ ID NO: 7)-A (herein referred to as 74-01-06-N001);

A-(SEQ ID NO: 8)-A (herein referred to as 74-01-07-N001);

A-(SEQ ID NO: 9)-A (herein referred to as 74-01-08-N001);

A-(SEQ ID NO: 10)-A (herein referred to as 74-01-09-N001);

A-(SEQ ID NO: 10)-SVG (herein referred to as 74-01-09-T03-N002);

A-(SEQ ID NO: 11)-A (herein referred to as 74-01-10-N001);

A-(SEQ ID NO: 12)-A (herein referred to as 74-01-11-N001);

A-(SEQ ID NO: 13)-A (herein referred to as 74-01-13-N001); and

A-(SEQ ID NO: 14)-A (herein referred to as 74-01-14-N001).

In a further embodiment, the peptide ligand of $C_i$-D-I-G-P-P-Y-$C_{ii}$-Y-R/A-D-M/P-Y-M-$C_{iii}$ (SEQ ID NO: 21) comprises an amino acid sequence selected from:

$$C_iDIGPPYC_{ii}YRDMYMC_{iii}; \text{ (SEQ ID NO: 15)}$$
and $$C_iDIGPPYC_{ii}YADPYMC_{iii}; \text{ (SEQ ID NO: 16)}$$

wherein $C_i$, $C_{ii}$ and $C_{iii}$ represent first, second and third cysteine residues, respectively, or a pharmaceutically acceptable salt thereof.

In a further embodiment, the peptide ligand of $C_i$-D-I-G-P-P-Y-$C_{ii}$-Y-R/A-D-M/P-Y-M-$C_{iii}$ (SEQ ID NO: 21) comprises an amino acid sequence selected from:

A-(SEQ ID NO: 15)-A (herein referred to as 74-01-16-N001); and

A-(SEQ ID NO: 16)-A (herein referred to as 74-01-17-N001).

In a further embodiment, the peptide ligand of $C_i$-D-E-W-G-L-F/Y-$C_{ii}$-I/F-P/A-H-S/P-D-$C_{iii}$ (SEQ ID NO: 22) comprises an amino acid sequence selected from:

$$C_iDEWGLFC_{ii}IPHSDC_{iii}; \text{ (SEQ ID NO: 17)}$$
and $$C_iDEWGLYC_{ii}FAHPDC_{iii}; \text{ (SEQ ID NO: 18)}$$

wherein $C_i$, $C_{ii}$ and $C_{iii}$ represent first, second and third cysteine residues, respectively, or a pharmaceutically acceptable salt thereof.

In a further embodiment, the peptide ligand of $C_i$-D-E-W-G-L-F/Y-$C_{ii}$-I/F-P/A-H-S/P-D-$C_{iii}$ (SEQ ID NO: 22) comprises an amino acid sequence selected from:

Ac-A-(SEQ ID NO: 17)-A (herein referred to as 74-02-00-N004); and

A-(SEQ ID NO: 18)-A (herein referred to as 74-02-01-N001).

In one embodiment, the peptide ligand of $C_i$IEPGPFC$_{ii}$-YADPYMC$_{iii}$ (SEQ ID NO: 19) comprises an amino acid sequence of:

A-(SEQ ID NO: 19)-NRV (herein referred to as 74-19-00-T01-N002).

In one embodiment, the molecular scaffold is selected from 1,1',1"-(1,3,5-triazinane-1,3,5-triyl)triprop-2-en-1-one (TATA) and the peptide ligand comprises an amino acid sequence selected from:

A-(SEQ ID NO: 1)-A (herein referred to as 74-01-00-N004);

A-(SEQ ID NO: 2)-A (herein referred to as 74-01-01-N001);

A-(SEQ ID NO: 3)-A (herein referred to as 74-01-02-N001);

A-(SEQ ID NO: 4)-A (herein referred to as 74-01-03-N001);

A-(SEQ ID NO: 5)-A (herein referred to as 74-01-04-N001);

A-(SEQ ID NO: 6)-A (herein referred to as 74-01-05-N001);

A-(SEQ ID NO: 7)-A (herein referred to as 74-01-06-N001);

A-(SEQ ID NO: 8)-A (herein referred to as 74-01-07-N001);

A-(SEQ ID NO: 9)-A (herein referred to as 74-01-08-N001);

A-(SEQ ID NO: 10)-A (herein referred to as 74-01-09-N001);

A-(SEQ ID NO: 10)-SVG (herein referred to as 74-01-09-T03-N002);

A-(SEQ ID NO: 11)-A (herein referred to as 74-01-10-N001);

A-(SEQ ID NO: 12)-A (herein referred to as 74-01-11-N001);

A-(SEQ ID NO: 13)-A (herein referred to as 74-01-13-N001);

A-(SEQ ID NO: 14)-A (herein referred to as 74-01-14-N001);

A-(SEQ ID NO: 15)-A (herein referred to as 74-01-16-N001);

A-(SEQ ID NO: 16)-A (herein referred to as 74-01-17-N001);

Ac-A-(SEQ ID NO: 17)-A (herein referred to as 74-02-00-N004); and

A-(SEQ ID NO: 18)-A (herein referred to as 74-02-01-N001).

The scaffold/peptide ligands of this embodiment demonstrated superior CD137 competition binding as shown herein in Table 1.

In a yet further embodiment, said peptide ligand is selected from:

$$C_iIEEGQYC_{ii}FADPY(Nle)C_{iii}; \text{ (SEQ ID NO: 23)}$$

$$C_iIKEGQYC_{ii}FADPY(Nle)C_{iii}; \text{ (SEQ ID NO: 24)}$$

$$C_iIEKGQYC_{ii}FADPY(Nle)C_{iii}; \text{ (SEQ ID NO: 25)}$$

$$C_iIEE(D-K)QYC_{ii}FADPY(Nle)C_{iii}; \text{ (SEQ ID NO: 26)}$$

$$C_iIEEGKYC_{ii}FADPY(Nle)C_{iii}; \text{ (SEQ ID NO: 27)}$$

$$C_iIEEGQYC_{ii}KADPY(Nle)C_{iii}; \text{ (SEQ ID NO: 28)}$$

$$C_iIEEGQYC_{ii}FADKY(Nle)C_{iii}; \text{ (SEQ ID NO: 29)}$$
and

-continued (SEQ ID NO: 30)
$C_i$IEEGQYC$_{ii}$FADPYKC$_{iii}$;

wherein $C_i$, $C_{ii}$ and $C_{iii}$ represent first, second and third cysteine residues, respectively or a pharmaceutically acceptable salt thereof.

In a yet further embodiment, said peptide ligand comprises N and C terminal modifications and comprises an amino acid sequence selected from:

A-$C_i$IEEGQYC$_{ii}$FADPY(Nle)C$_{iii}$-A (SEQ ID NO: 31; BCY3814);
Ac-A-$C_i$IEEGQYC$_{ii}$FADPY(Nle)C$_{iii}$-Dap (SEQ ID NO: 32; BCY7732);
Ac-A-$C_i$IKEGQYC$_{ii}$FADPY(Nle)C$_{iii}$-A (SEQ ID NO: 33; BCY7733);
Ac-A-$C_i$IEKGQYC$_{ii}$FADPY(Nle)C$_{iii}$-A (SEQ ID NO: 34; BCY7734);
Ac-A-$C_i$IEE(D-K)QYC$_{ii}$FADPY(Nle)C$_{iii}$-A (SEQ ID NO: 35; BCY7735);
Ac-A-$C_i$IEEGKYC$_{ii}$FADPY(Nle)C$_{iii}$-A (SEQ ID NO: 36; BCY7736);
Ac-A-$C_i$IEEGQYC$_{ii}$KADPY(Nle)C$_{iii}$-A (SEQ ID NO: 37; BCY7737);
Ac-A-$C_i$IEEGQYC$_{ii}$FADKY(Nle)C$_{iii}$-A (SEQ ID NO: 38; BCY7738); and
Ac-A-$C_i$IEEGQYC$_{ii}$FADPYKC$_{iii}$-A (SEQ ID NO: 39; BCY7739);

wherein $C_i$, $C_{ii}$ and $C_{iii}$ represent first, second and third cysteine residues, respectively, Ac represents an N-terminal acetyl group and Dap represents diaminopropionic acid or a pharmaceutically acceptable salt thereof.

In an alternative embodiment, said peptide ligand comprises an amino acid sequence which is:

(SEQ ID NO: 40; 74-22-00)
$C_i$LPPGQYC$_{ii}$FPDLLLC$_{iii}$ wherein $C_i$, $C_{ii}$ and $C_{iii}$ represent first, second and third cysteine residues, respectively.

In an alternative embodiment, said peptide ligand comprises three cysteine residues separated by two loop sequences both of which consist of 6 amino acids, and said peptide ligand comprises an amino acid seauence which is.

(SEQ ID NO: 41)
$C_i$-I/L/M/V-E/D/P/S-P/E/A-G-P/Q-Y/F-$C_{ii}$-Y-A-D-P-Y/M-M/L/Y-$C_{iii}$;

wherein $C_i$, $C_{ii}$ and $C_{iii}$ represent first, second and third cysteine residues, respectively.

In a further embodiment, said amino acid sequence is selected from the peptide sequences listed in Table 1. In a yet further embodiment, said amino acid sequence is selected from the peptide sequences listed in Table 1 excluding the peptides of BCY7238, BCY7241, BCY7243 and BCY7246. The peptides of this embodiment were tested in the CD137 direct binding assay and demonstrated good levels of binding.

In a further embodiment, said amino acid sequence is selected from the peptide sequences listed in Table 3. The peptides of this embodiment were tested in the CD137 direct binding assay and demonstrated good levels of binding.

In a further embodiment, said amino acid sequence is selected from the peptide sequences listed in Tables 4 and 5.

The peptides of this embodiment were tested in the CD137 SPR assay and demonstrated good levels of binding.

In a further embodiment, said amino acid sequence is selected from BCY592. Data is presented herein in FIG. 1 which shows that the bicyclic peptide BCY592 inhibited CD137L activity in a cell-based assay.

In an alternative embodiment, said peptide ligand comprises three cysteine residues separated by two loop sequences both of which consist of 6 amino acids, and said peptide ligand comprises an amino acid sequence which is:

(SEQ ID NO: 266)
$C_i$-$X_5$-$X_6$-$X_7$-$X_8$-$X_9$-$X_{10}$-$C_{ii}$-$X_{11}$-$X_{12}$-D-$X_{13}$-$X_{14}$-$X_{15}$-$C_{iii}$;

wherein $C_i$, $C_{ii}$ and $C_{iii}$ represent first, second and third cysteine residues, respectively;

$X_5$ represents Ile, tBuAla or Chg;
$X_6$ represents Glu, Pro, Asp, Lys, Aad, HyP or Oxa;
$X_7$ represents Glu, Lys or Aad;
$X_8$ represents Gly, D-Lys, D-Ala, L-Ala, D-Phe, D-Glu, D-Gln, D-Leu, D-Ser or D-Trp;
$X_9$ represents Gln, Lys, Ala, Pro, 5,5-dmP, Oic, Oxa, HyP, Aib or Ac5c;
$X_{10}$ represents Tyr, Phe, 3MePhe, 4MePhe, 4FPhe, 2Nal, 4MeOPhe or 4,4-BPA;
$X_{11}$ represents Phe, Lys, 4MePhe, 2FPhe, 4FPhe, 4Pal, 4,4-BPA, 4tBuPhe, NO2Phe or 4BrPhe;
$X_{12}$ represents Ala or Lys;
$X_{13}$ represents Pro or Lys;
$X_{14}$ represents Tyr or Lys; and
$X_{15}$ represents Met, Lys, Nle, HLeu or Ahp.

In one embodiment, the peptide ligand of SEQ ID NO: 266 is selected from the $C_i$ to $C_{iii}$ sequences of the following peptides (i.e. absent any N-terminal and C-terminal additions):

BCY7239, BCY7240, BCY7242, BCY7244, BCY7245, BCY7247, BCY7248, BCY7249, BCY7416, BCY7287, BCY7297, BCY7154, BCY7156, BCY7157, BCY7158, BCY7162, BCY7165, BCY7166, BCY7167, BCY7168, BCY7169, BCY7170, BCY7174, BCY7175, BCY7177, BCY7178, BCY7179, BCY7183, BCY7185, BCY7195, BCY7198, BCY7211, BCY7311, BCY7768, BCY7770, BCY7772, BCY7773, BCY7774, BCY7775, BCY7776, BCY7796, BCY7798, BCY7801, BCY7802, BCY7936, BCY7941, BCY7942, BCY7944, BCY7950, BCY7954, BCY7958, BCY7959, BCY7960, BCY7952, BCY7961, BCY8656, BCY8659, BCY8663, BCY8668, BCY8669, BCY8674, BCY8675, BCY9273, BCY3814, BCY7527 and BCY7965.

In a further embodiment, the peptide ligand of SEQ ID NO: 266 is selected from the full sequences of the following peptides (i.e. including all N-terminal and C-terminal additions):

BCY7239, BCY7240, BCY7242, BCY7244, BCY7245, BCY7247, BCY7248, BCY7249, BCY7416, BCY7287, BCY7297, BCY7154, BCY7156, BCY7157, BCY7158, BCY7162, BCY7165, BCY7166, BCY7167, BCY7168, BCY7169, BCY7170, BCY7174, BCY7175, BCY7177, BCY7178, BCY7179, BCY7183, BCY7185, BCY7195, BCY7198, BCY7211, BCY7311, BCY7768, BCY7770, BCY7772, BCY7773, BCY7774, BCY7775, BCY7776, BCY7796, BCY7798, BCY7801, BCY7802, BCY7936, BCY7941, BCY7942, BCY7944, BCY7950, BCY7954, BCY7958, BCY7959, BCY7960, BCY7952, BCY7961,

BCY8656, BCY8659, BCY8663, BCY8668, BCY8669, BCY8674, BCY8675, BCY9273, BCY3814, BCY7527 and BCY7965.

These peptides either all demonstrated good levels of binding in the direct binding or SPR assays described herein or represented peptides which are tolerant of substitution with a Lys residue.

In one embodiment, $X_5$ represents Ile or tBuAla.
In one embodiment, $X_6$ represents Lys, Glu or Pro.
In one embodiment, $X_7$ represents Glu or D-Lys.
In one embodiment, $X_8$ represents Gly, D-Lys, D-Phe or D-Ala.
In one embodiment, $X_9$ represents Gln, Lys or Pro.
In one embodiment, $X_{10}$ represents Tyr or 4MePhe.
In one embodiment, $X_{11}$ represents Phe or 4FPhe.
In one embodiment, $X_{12}$ represents Ala.
In one embodiment, $X_{13}$ represents Pro.
In one embodiment, $X_{14}$ represents Tyr.
In one embodiment, $X_{15}$ represents Met or Nle.

In a further embodiment, said peptide ligand comprises three cysteine residues separated by two loop sequences both of which consist of 6 amino acids, and said peptide ligand comprises an amino acid sequence which is:

(SEQ ID NO: 267)
$C_i$-$X_5$-$X_6$-$X_7$-$X_8$-$X_9$-$X_{10}$-$C_{ii}$-$X_{11}$-A-D-P-Y-$X_{15}$-$C_{iii}$;

wherein $C_i$, $C_{ii}$ and $C_{iii}$ represent first, second and third cysteine residues, respectively;
 $X_5$ represents Ile or tBuAla;
 $X_6$ represents Lys, Glu or Pro;
 $X_7$ represents Glu or D-Lys;
 $X_8$ represents Gly, D-Lys, D-Phe or D-Ala;
 $X_9$ represents Gln, Lys or Pro;
 $X_{10}$ represents Tyr or 4MePhe;
 $X_{11}$ represents Phe or 4FPhe; and
 $X_{15}$ represents Met or Nle.

In one embodiment, the peptide ligand of SEQ ID NO: 267 is selected from the $C_i$ to $C_{iii}$ sequences of the following peptides (i.e. absent any N-terminal and C-terminal additions): BCY7239, BCY7240, BCY7242, BCY7416, BCY7156, BCY7166, BCY7174, BCY7774, BCY9273, BCY3814, BCY7527 and BCY7965.

In a further embodiment, the peptide ligand of SEQ ID NO: 267 is selected from the full sequences of the following peptides (i.e. including all N-terminal and C-terminal additions): BCY7239, BCY7240, BCY7242, BCY7416, BCY7156, BCY7166, BCY7174, BCY7774, BCY9273, BCY3814, BCY7527 and BCY7965.

These peptides either all demonstrated excellent levels of binding in the direct binding or SPR assays described herein or represented peptides which are tolerant of substitution with a Lys residue.

In one embodiment, the peptide ligand of SEQ ID NO: 267 is selected from the $C_i$ to $C_{iii}$ sequences of the following peptides (i.e. absent any N-terminal and C-terminal additions): BCY7239, BCY7240, BCY7242 and BCY7416.

In a further embodiment, the peptide ligand of SEQ ID NO: 267 is selected from the full sequences of the following peptides (i.e. including all N-terminal and C-terminal additions): BCY7239, BCY7240, BCY7242 and BCY7416.

These peptides represented peptides which are tolerant of substitution with a Lys residue.

In one embodiment, the peptide ligand of SEQ ID NO: 267 is selected from the $C_i$ to $C_{iii}$ sequences of the following peptides (i.e. absent any N-terminal and C-terminal additions): BCY9273, BCY3814, BCY7527 and BCY7965.

In a further embodiment, the peptide ligand of SEQ ID NO: 267 is selected from the full sequences of the following peptides (i.e. including all N-terminal and C-terminal additions): BCY9273, BCY3814, BCY7527 and BCY7965.

These peptides either all demonstrated good levels of binding in the direct binding or SPR assays described herein.

In one embodiment, the peptide ligand of SEQ ID NO: 267 is selected from the $C_i$ to $C_{iii}$ sequences of the following peptides (i.e. absent any N-terminal and C-terminal additions): BCY7156, BCY7166, BCY7174 and BCY7774.

In a further embodiment, the peptide ligand of SEQ ID NO: 267 is selected from the full sequences of the following peptides (i.e. including all N-terminal and C-terminal additions): BCY7156, BCY7166, BCY7174 and BCY7774.

These peptides either all demonstrated excellent levels of binding in the direct binding or SPR assays described herein.

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) $4^{th}$ ed., John Wiley & Sons, Inc.), which are incorporated herein by reference.

Nomenclature

Numbering

When referring to amino acid residue positions within compounds of formula (I), cysteine residues ($C_i$, $C_{ii}$ and $C_{iii}$) are omitted from the numbering as they are invariant, therefore, the numbering of amino acid residues within the compound of formula (I) is referred to as below:

(SEQ ID NO: 1)
-$C_i$-$I_1$-$E_2$-$E_3$-$G_4$-$Q_5$-$Y_6$-$C_{ii}$-$Y_7$-$R_8$-$D_9$-$M_{10}$-$Y_{11}$-$M_{12}$-$C_{iii}$-

For the purpose of this description, all bicyclic peptides are assumed to be cyclised with TBMB (1,3,5-tris(bromomethyl)benzene) or 1,1',1"-(1,3,5-triazinane-1,3,5-tril)triprop-2-en-1-one (TATA) and yielding a tri-substituted structure. Cyclisation with TBMB and TATA occurs on $C_i$, $C_{ii}$, and $C_{iii}$.

Molecular Format

N- or C-terminal extensions to the bicycle core sequence are added to the left or right side of the sequence, separated by a hyphen. For example, an N-terminal βAla-Sar10-Ala tail would be denoted as:

(SEQ ID NO: X)
βAla-Sar10-A-

Peptide Ligands

A peptide ligand, as referred to herein, refers to a peptide covalently bound to a molecular scaffold. Typically, such peptides comprise two or more reactive groups (i.e. cysteine residues) which are capable of forming covalent bonds to the scaffold, and a sequence subtended between said reactive groups which is referred to as the loop sequence, since it forms a loop when the peptide is bound to the scaffold. In the present case, the peptides comprise at least three cysteine residues (referred to herein as $C_i$, $C_{ii}$ and $C_{iii}$), and form at least two loops on the scaffold.

Advantages of the Peptide Ligands

Certain bicyclic peptides of the present invention have a number of advantageous properties which enable them to be considered as suitable drug-like molecules for injection, inhalation, nasal, ocular, oral or topical administration. Such advantageous properties include:

Species cross-reactivity. This is a typical requirement for preclinical pharmacodynamics and pharmacokinetic evaluation;

Protease stability. Bicyclic peptide ligands should ideally demonstrate stability to plasma proteases, epithelial ("membrane-anchored") proteases, gastric and intestinal proteases, lung surface proteases, intracellular proteases and the like. Protease stability should be maintained between different species such that a bicycle lead candidate can be developed in animal models as well as administered with confidence to humans;

Desirable solubility profile. This is a function of the proportion of charged and hydrophilic versus hydrophobic residues and intra/inter-molecular H-bonding, which is important for formulation and absorption purposes; and An optimal plasma half-life in the circulation. Depending upon the clinical indication and treatment regimen, it may be required to develop a bicyclic peptide for short exposure in an acute illness management setting, or develop a bicyclic peptide with enhanced retention in the circulation, and is therefore optimal for the management of more chronic disease states. Other factors driving the desirable plasma half-life are requirements of sustained exposure for maximal therapeutic efficiency versus the accompanying toxicology due to sustained exposure of the agent.

Selectivity. Certain peptide ligands of the invention demonstrate good selectivity over other CDs.

Pharmaceutically Acceptable Salts

It will be appreciated that salt forms are within the scope of this invention, and references to peptide ligands include the salt forms of said ligands.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, sulfuric, methanesulfonic (mesylate), ethanesulfonic, naphthalenesulfonic, valeric, propanoic, butanoic, malonic, glucuronic and lactobionic acids. One particular salt is the hydrochloride salt. Another particular salt is the acetate salt.

If the compound is anionic, or has a functional group which may be anionic (e.g., —COOH may be —COO$^-$), then a salt may be formed with an organic or inorganic base, generating a suitable cation. Examples of suitable inorganic cations include, but are not limited to, alkali metal ions such as Li$^+$, Na$^+$ and K$^+$, alkaline earth metal cations such as Ca$^{2+}$ and Mg$^{2+}$, and other cations such as Al$^{3+}$ or Zn$^+$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

Where the compounds of formula (I) contain an amine function, these may form quaternary ammonium salts, for example by reaction with an alkylating agent according to methods well known to the skilled person. Such quaternary ammonium compounds are within the scope of formula (I).

Modified Derivatives

It will be appreciated that modified derivatives of the peptide ligands as defined herein are within the scope of the present invention. Examples of such suitable modified derivatives include one or more modifications selected from: N-terminal and/or C-terminal modifications; replacement of one or more amino acid residues with one or more non-natural amino acid residues (such as replacement of one or more polar amino acid residues with one or more isosteric or isoelectronic amino acids; replacement of one or more non-polar amino acid residues with other non-natural isosteric or isoelectronic amino acids); addition of a spacer group; replacement of one or more oxidation sensitive amino acid residues with one or more oxidation resistant amino acid residues; replacement of one or more amino acid residues with an alanine, replacement of one or more L-amino acid residues with one or more D-amino acid residues; N-alkylation of one or more amide bonds within the bicyclic peptide ligand; replacement of one or more peptide bonds with a surrogate bond; peptide backbone length modification; substitution of the hydrogen on the alpha-carbon of one or more amino acid residues with another chemical group, modification of amino acids such as cysteine, lysine, glutamate/aspartate and tyrosine with suitable amine, thiol, carboxylic acid and phenol-reactive reagents so as to functionalise said amino acids, and introduction or replacement of amino acids that introduce orthogonal reactivities that are suitable for functionalisation, for example azide or alkyne-group bearing amino acids that allow functionalisation with alkyne or azide-bearing moieties, respectively.

In one embodiment, the modified derivative comprises an N-terminal and/or C-terminal modification. In a further embodiment, wherein the modified derivative comprises an N-terminal modification using suitable amino-reactive chemistry, and/or C-terminal modification using suitable carboxy-reactive chemistry. In a further embodiment, said N-terminal or C-terminal modification comprises addition of an effector group, including but not limited to a cytotoxic agent, a radiochelator or a chromophore.

In a further embodiment, the modified derivative comprises an N-terminal modification. In a further embodiment, the N-terminal modification comprises an N-terminal acetyl group. In this embodiment, the N-terminal cysteine group (the group referred to herein as $C_i$) is capped with acetic anhydride or other appropriate reagents during peptide synthesis leading to a molecule which is N-terminally acetylated. This embodiment provides the advantage of removing a potential recognition point for aminopeptidases and avoids the potential for degradation of the bicyclic peptide.

In an alternative embodiment, the N-terminal modification comprises the addition of a molecular spacer group which facilitates the conjugation of effector groups and retention of potency of the bicyclic peptide to its target.

In a further embodiment, the modified derivative comprises a C-terminal modification. In a further embodiment, the C-terminal modification comprises an amide group. In this embodiment, the C-terminal cysteine group (the group referred to herein as $C_{ii}$) is synthesized as an amide during peptide synthesis leading to a molecule which is C-terminally amidated. This embodiment provides the advantage of removing a potential recognition point for carboxypeptidase and reduces the potential for proteolytic degradation of the bicyclic peptide.

In one embodiment, the modified derivative comprises replacement of one or more amino acid residues with one or more non-natural amino acid residues. In this embodiment, non-natural amino acids may be selected having isosteric/isoelectronic side chains which are neither recognised by degradative proteases nor have any adverse effect upon target potency.

Alternatively, non-natural amino acids may be used having constrained amino acid side chains, such that proteolytic hydrolysis of the nearby peptide bond is conformationally and sterically impeded. In particular, these concern proline analogues, bulky sidechains, Cα-disubstituted derivatives (for example, aminoisobutyric acid, Aib), and cyclo amino acids, a simple derivative being amino-cyclopropylcarboxylic acid.

In one embodiment, the modified derivative comprises the addition of a spacer group. In a further embodiment, the modified derivative comprises the addition of a spacer group to the N-terminal cysteine ($C_i$) and/or the C-terminal cysteine ($C_{ii}$).

In one embodiment, the modified derivative comprises replacement of one or more oxidation sensitive amino acid residues with one or more oxidation resistant amino acid residues. In a further embodiment, the modified derivative comprises replacement of a tryptophan residue with a naphthylalanine or alanine residue. This embodiment provides the advantage of improving the pharmaceutical stability profile of the resultant bicyclic peptide ligand.

In one embodiment, the modified derivative comprises replacement of one or more charged amino acid residues with one or more hydrophobic amino acid residues. In an alternative embodiment, the modified derivative comprises replacement of one or more hydrophobic amino acid residues with one or more charged amino acid residues. The correct balance of charged versus hydrophobic amino acid residues is an important characteristic of the bicyclic peptide ligands. For example, hydrophobic amino acid residues influence the degree of plasma protein binding and thus the concentration of the free available fraction in plasma, while charged amino acid residues (in particular arginine) may influence the interaction of the peptide with the phospholipid membranes on cell surfaces. The two in combination may influence half-life, volume of distribution and exposure of the peptide drug, and can be tailored according to the clinical endpoint. In addition, the correct combination and number of charged versus hydrophobic amino acid residues may reduce irritation at the injection site (if the peptide drug has been administered subcutaneously).

In one embodiment, the modified derivative comprises replacement of one or more L-amino acid residues with one or more D-amino acid residues. This embodiment is believed to increase proteolytic stability by steric hindrance and by a propensity of D-amino acids to stabilise β-turn conformations (Tugyi et al (2005) PNAS, 102(2), 413-418).

In one embodiment, the modified derivative comprises removal of any amino acid residues and substitution with alanines. This embodiment provides the advantage of removing potential proteolytic attack site(s).

It should be noted that each of the above mentioned modifications serve to deliberately improve the potency or stability of the peptide. Further potency improvements based on modifications may be achieved through the following mechanisms:

Incorporating hydrophobic moieties that exploit the hydrophobic effect and lead to lower off rates, such that higher affinities are achieved;

Incorporating charged groups that exploit long-range ionic interactions, leading to faster on rates and to higher affinities (see for example Schreiber et al, *Rapid, electrostatically assisted association of proteins* (1996), Nature Struct. Biol. 3, 427-31); and Incorporating additional constraint into the peptide, by for example constraining side chains of amino acids correctly such that loss in entropy is minimal upon target binding, constraining the torsional angles of the backbone such that loss in entropy is minimal upon target binding and introducing additional cyclisations in the molecule for identical reasons.

(for reviews see Gentilucci et al, Curr. Pharmaceutical Design, (2010), 16, 3185-203, and Nestor et al, Curr. Medicinal Chem (2009), 16, 4399-418).

Isotopic Variations

The present invention includes all pharmaceutically acceptable (radio)isotope-labelled peptide ligands of the invention, wherein one or more atoms are replaced by atoms having the same atomic number, but an atomic mass or mass number different from the atomic mass or mass number usually found in nature, and peptide ligands of the invention, wherein metal chelating groups are attached (termed "effector") that are capable of holding relevant (radio)isotopes, and peptide ligands of the invention, wherein certain functional groups are covalently replaced with relevant (radio) isotopes or isotopically labelled functional groups.

Examples of isotopes suitable for inclusion in the peptide ligands of the invention comprise isotopes of hydrogen, such as $^{2}H$ (D) and $^{3}H$ (T), carbon, such as $^{11}C$ $^{13}C$ and $^{14}C$, chlorine, such as $^{36}Cl$, fluorine, such as $^{18}F$, iodine, such as $^{123}I$, $^{125}I$ and $^{131}I$, nitrogen, such as $^{13}N$ and $^{15}N$, oxygen, such as $^{15}O$, $^{17}O$ and $^{18}O$, phosphorus, such as $^{32}P$, sulphur, such as $^{35}S$, copper, such as $^{64}Cu$, gallium, such as $^{67}Ga$ or $^{68}Ga$, yttrium, such as $^{90}Y$ and lutetium, such as $^{177}Lu$, and Bismuth, such as $^{213}Bi$.

Certain isotopically-labelled peptide ligands of the invention, for example, those incorporating a radioactive isotope, are useful in drug and/or substrate tissue distribution studies, and to clinically assess the presence and/or absence of the CD137 target on diseased tissues. The peptide ligands of the invention can further have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3H$ (T), and carbon-14, i.e. $^{14}C$, are particularly useful for this purpose in view of their ease of incorporation and ready means of detection.

Substitution with heavier isotopes such as deuterium, i.e. $^2H$ (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining target occupancy.

Isotopically-labelled compounds of peptide ligands of the invention can generally be prepared by conventional techniques known to those skilled in the art or by processes analogous to those described in the accompanying Examples using an appropriate isotopically-labeled reagent in place of the non-labeled reagent previously employed.

Molecular Scaffold

Molecular scaffolds are described in, for example, WO 2009/098450 and references cited therein, particularly WO 2004/077062 and WO 2006/078161.

As noted in the foregoing documents, the molecular scaffold may be a small molecule, such as a small organic molecule.

In one embodiment the molecular scaffold may be a macromolecule. In one embodiment the molecular scaffold is a macromolecule composed of amino acids, nucleotides or carbohydrates.

In one embodiment the molecular scaffold comprises reactive groups that are capable of reacting with functional group(s) of the polypeptide to form covalent bonds.

The molecular scaffold may comprise chemical groups which form the linkage with a peptide, such as amines, thiols, alcohols, ketones, aldehydes, nitriles, carboxylic acids, esters, alkenes, alkynes, azides, anhydrides, succinimides, maleimides, alkyl halides and acyl halides.

In one embodiment, the molecular scaffold may comprise or may consist of hexahydro-1,3,5-triazine, especially 1,3,5-triacryloylhexahydro-1,3,5-triazine ("TATA"), or a derivative thereof.

In one embodiment, the molecular scaffold is 2,4,6-tris(bromomethyl)mesitylene. This molecule is similar to 1,3,5-tris(bromomethyl)benzene (TBMB) but contains three additional methyl groups attached to the benzene ring. This has the advantage that the additional methyl groups may form further contacts with the polypeptide and hence add additional structural constraint.

The molecular scaffold of the invention contains chemical groups that allow functional groups of the polypeptide of the encoded library of the invention to form covalent links with the molecular scaffold. Said chemical groups are selected from a wide range of functionalities including amines, thiols, alcohols, ketones, aldehydes, nitriles, carboxylic acids, esters, alkenes, alkynes, anhydrides, succinimides, maleimides, azides, alkyl halides and acyl halides.

Scaffold reactive groups that could be used on the molecular scaffold to react with thiol groups of cysteines are alkyl halides (or also named halogenoalkanes or haloalkanes).

Examples include bromomethylbenzene or iodoacetamide. Other scaffold reactive groups that are used to selectively couple compounds to cysteines in proteins are maleimides, αβ unsaturated carbonyl containing compounds and a-halomethylcarbonyl containing compounds. Examples of maleimides which may be used as molecular scaffolds in the invention include: tris-(2-maleimidoethyl)amine, tris-(2-maleimidoethyl)benzene, tris-(maleimido)benzene. An example of an αβ unsaturated carbonyl containing compound is 1,1',1''-(1,3,5-triazinane-1,3,5-tril)triprop-2-en-1-one (TATA) (Angewandte Chemie, International Edition (2014), 53(6), 1602-1606). An example of an α-halomethylcarbonyl containing compound is N,N',N''-(benzene-1,3,5-tril)tris(2-bromoacetamide). Selenocysteine is also a natural amino acid which has a similar reactivity to cysteine and can be used for the same reactions. Thus, wherever cysteine is mentioned, it is typically acceptable to substitute selenocysteine unless the context suggests otherwise.

Reactive Groups

The molecular scaffold of the invention may be bonded (i.e. covalently) to the polypeptide via functional or reactive groups on the polypeptide. These are typically formed from the side chains of particular amino acids found in the polypeptide polymer. Such reactive groups may be a cysteine side chain, a lysine side chain, or an N-terminal amine group or any other suitable reactive group. Details may be found in WO 2009/098450.

Examples of reactive groups of natural amino acids are the thiol group of cysteine, the amino group of lysine, the carboxyl group of aspartate or glutamate, the guanidinium group of arginine, the phenolic group of tyrosine or the hydroxyl group of serine. Non-natural amino acids can provide a wide range of reactive groups including an azide, a keto-carbonyl, an alkyne, a vinyl, or an aryl halide group. The amino and carboxyl group of the termini of the polypeptide can also serve as reactive groups to form covalent bonds to a molecular scaffold/molecular core.

In one embodiment, the reactive group comprises a cysteine residue. In an alternative embodiment, the reactive group comprises penicillamine.

The polypeptides of the invention contain at least three reactive groups. Said polypeptides can also contain four or more reactive groups. The more reactive groups are used, the more loops can be formed in the molecular scaffold.

In a preferred embodiment, polypeptides with three reactive groups are generated. Reaction of said polypeptides with a molecular scaffold/molecular core having a three-fold rotational symmetry generates a single product isomer. The generation of a single product isomer is favourable for several reasons. The nucleic acids of the compound libraries encode only the primary sequences of the polypeptide but not the isomeric state of the molecules that are formed upon reaction of the polypeptide with the molecular core. If only one product isomer can be formed, the assignment of the nucleic acid to the product isomer is clearly defined. If multiple product isomers are formed, the nucleic acid cannot give information about the nature of the product isomer that was isolated in a screening or selection process. The formation of a single product isomer is also advantageous if a specific member of a library of the invention is synthesized. In this case, the chemical reaction of the polypeptide with the molecular scaffold yields a single product isomer rather than a mixture of isomers.

In another embodiment of the invention, polypeptides with four reactive groups are generated. Reaction of said polypeptides with a molecular scaffold/molecular core having a tetrahedral symmetry generates two product isomers. Even though the two different product isomers are encoded by one and the same nucleic acid, the isomeric nature of the isolated isomer can be determined by chemically synthesizing both isomers, separating the two isomers and testing both isomers for binding to a target ligand.

In one embodiment of the invention, at least one of the reactive groups of the polypeptides is orthogonal to the remaining reactive groups. The use of orthogonal reactive groups allows the directing of said orthogonal reactive groups to specific sites of the molecular core. Linking strategies involving orthogonal reactive groups may be used to limit the number of product isomers formed. In other words, by choosing distinct or different reactive groups for one or more of the at least three bonds to those chosen for the remainder of the at least three bonds, a particular order of bonding or directing of specific reactive groups of the polypeptide to specific positions on the molecular scaffold may be usefully achieved.

In another embodiment, the reactive groups of the polypeptide of the invention are reacted with molecular linkers wherein said linkers are capable to react with a molecular scaffold so that the linker will intervene between the molecular scaffold and the polypeptide in the final bonded state.

In some embodiments, amino acids of the members of the libraries or sets of polypeptides can be replaced by any natural or non-natural amino acid. Excluded from these exchangeable amino acids are the ones harbouring functional groups for cross-linking the polypeptides to a molecular core, such that the loop sequences alone are exchangeable. The exchangeable polypeptide sequences have either random sequences, constant sequences or sequences with random and constant amino acids. The amino acids with reactive groups are either located in defined positions within the polypeptide, since the position of these amino acids determines loop size.

Alternatives to thiol-mediated conjugations can be used to attach the molecular scaffold to the peptide via covalent interactions. Alternatively these techniques may be used in modification or attachment of further moieties (such as small molecules of interest which are distinct from the molecular scaffold) to the polypeptide after they have been selected or isolated according to the present invention—in this embodiment then clearly the attachment need not be covalent and may embrace non-covalent attachment. These methods may be used instead of (or in combination with) the thiol mediated methods by producing phage that display proteins and peptides bearing unnatural amino acids with the requisite chemical reactive groups, in combination small molecules that bear the complementary reactive group, or by incorporating the unnatural amino acids into a chemically or recombinantly synthesised polypeptide when the molecule is being made after the selection/isolation phase. Further details can be found in WO 2009/098450 or Heinis, et al., Nat Chem Biol 2009, 5 (7), 502-7.

Effector and Functional Groups

According to a further aspect of the invention, there is provided a drug conjugate comprising a peptide ligand as defined herein conjugated to one or more effector and/or functional groups.

Effector and/or functional groups can be attached, for example, to the N and/or C termini of the polypeptide, to an amino acid within the polypeptide, or to the molecular scaffold.

Appropriate effector groups include antibodies and parts or fragments thereof. For instance, an effector group can include an antibody light chain constant region (CL), an antibody CH1 heavy chain domain, an antibody CH2 heavy chain domain, an antibody CH3 heavy chain domain, or any combination thereof, in addition to the one or more constant region domains. An effector group may also comprise a hinge region of an antibody (such a region normally being found between the CH1 and CH2 domains of an IgG molecule).

In a further embodiment of this aspect of the invention, an effector group according to the present invention is an Fc region of an IgG molecule. Advantageously, a peptide ligand-effector group according to the present invention comprises or consists of a peptide ligand Fc fusion having a tβ half-life of a day or more, two days or more, 3 days or more, 4 days or more, 5 days or more, 6 days or more or 7 days or more. Most advantageously, the peptide ligand according to the present invention comprises or consists of a peptide ligand Fc fusion having a tβ half-life of a day or more.

Functional groups include, in general, binding groups, drugs, reactive groups for the attachment of other entities, functional groups which aid uptake of the macrocyclic peptides into cells, and the like.

The ability of peptides to penetrate into cells will allow peptides against intracellular targets to be effective. Targets that can be accessed by peptides with the ability to penetrate into cells include transcription factors, intracellular signalling molecules such as tyrosine kinases and molecules involved in the apoptotic pathway. Functional groups which enable the penetration of cells include peptides or chemical groups which have been added either to the peptide or the molecular scaffold. Peptides such as those derived from such as VP22, HIV-Tat, a homeobox protein of Drosophila (Antennapedia), e.g. as described in Chen and Harrison, Biochemical Society Transactions (2007) Volume 35, part 4, p 821; Gupta et al. in Advanced Drug Discovery Reviews (2004) Volume 57 9637. Examples of short peptides which have been shown to be efficient at translocation through plasma membranes include the 16 amino acid penetratin peptide from Drosophila Antennapedia protein (Derossi et al (1994) J Biol. Chem. Volume 269 p 10444), the 18 amino acid 'model amphipathic peptide' (Oehlke et al (1998) Biochim Biophys Acts Volume 1414 p 127) and arginine rich regions of the HIV TAT protein. Non peptidic approaches include the use of small molecule mimics or SMOCs that can be easily attached to biomolecules (Okuyama et al (2007) Nature Methods Volume 4 p 153). Other chemical strategies to add guanidinium groups to molecules also enhance cell penetration (Elson-Scwab et al (2007) J Biol Chem Volume 282 p 13585). Small molecular weight molecules such as steroids may be added to the molecular scaffold to enhance uptake into cells.

One class of functional groups which may be attached to peptide ligands includes antibodies and binding fragments thereof, such as Fab, Fv or single domain fragments. In particular, antibodies which bind to proteins capable of increasing the half-life of the peptide ligand in vivo may be used.

In one embodiment, a peptide ligand-effector group according to the invention has a tβ half-life selected from the group consisting of: 12 hours or more, 24 hours or more, 2 days or more, 3 days or more, 4 days or more, 5 days or more, 6 days or more, 7 days or more, 8 days or more, 9 days or more, 10 days or more, 11 days or more, 12 days or more, 13 days or more, 14 days or more, 15 days or more or 20 days or more. Advantageously a peptide ligand-effector group or composition according to the invention will have a tβ half-life in the range 12 to 60 hours. In a further embodiment, it will have a tβ half-life of a day or more. In a further embodiment still, it will be in the range 12 to 26 hours.

In one particular embodiment of the invention, the functional group is selected from a metal chelator, which is suitable for complexing metal radioisotopes of medicinal relevance.

Possible effector groups also include enzymes, for instance such as carboxypeptidase G2 for use in enzyme/prodrug therapy, where the peptide ligand replaces antibodies in ADEPT.

In one particular embodiment of the invention, the functional group is selected from a drug, such as a cytotoxic agent for cancer therapy. Suitable examples include: alkylating agents such as cisplatin and carboplatin, as well as oxaliplatin, mechlorethamine, cyclophosphamide, chlorambucil, ifosfamide; Anti-metabolites including purine analogs azathioprine and mercaptopurine or pyrimidine analogs; plant alkaloids and terpenoids including vinca alkaloids such as Vincristine, Vinblastine, Vinorelbine and Vindesine; Podophyllotoxin and its derivatives etoposide and teniposide; Taxanes, including paclitaxel, originally known as Taxol; topoisomerase inhibitors including camptothecins: irinotecan and topotecan, and type II inhibitors including amsacrine, etoposide, etoposide phosphate, and teniposide. Further agents can include antitumour antibiotics which include the immunosuppressant dactinomycin (which is used in kidney transplantations), doxorubicin, epirubicin, bleomycin, calicheamycins, and others.

In one further particular embodiment of the invention, the cytotoxic agent is selected from maytansinoids (such as DM1) or monomethyl auristatins (such as MMAE).

DM1 is a cytotoxic agent which is a thiol-containing derivative of maytansine and has the following structure:

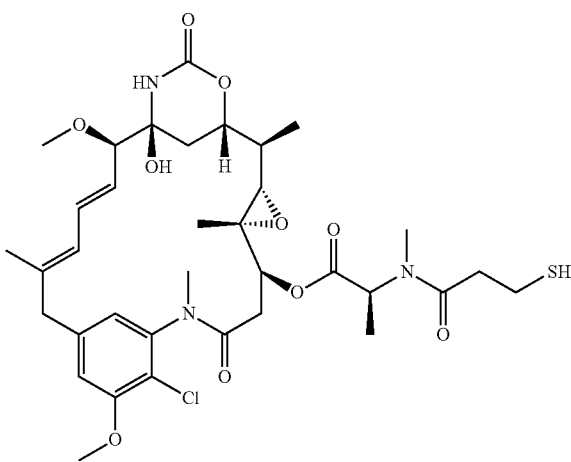

Monomethyl auristatin E (MMAE) is a synthetic antineoplastic agent and has the following structure:

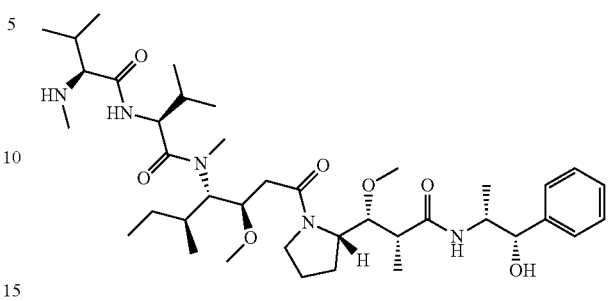

In one yet further particular embodiment of the invention, the cytotoxic agent is selected from maytansinoids (such as DM1).

In one embodiment, the cytotoxic agent is linked to the bicyclic peptide by a cleavable bond, such as a disulphide bond or a protease sensitive bond. In a further embodiment, the groups adjacent to the disulphide bond are modified to control the hindrance of the disulphide bond, and by this the rate of cleavage and concomitant release of cytotoxic agent.

Published work established the potential for modifying the susceptibility of the disulphide bond to reduction by introducing steric hindrance on either side of the disulphide bond (Kellogg et al (2011) Bioconjugate Chemistry, 22, 717). A greater degree of steric hindrance reduces the rate of reduction by intracellular glutathione and also extracellular (systemic) reducing agents, consequentially reducing the ease by which toxin is released, both inside and outside the cell. Thus, selection of the optimum in disulphide stability in the circulation (which minimises undesirable side effects of the toxin) versus efficient release in the intracellular milieu (which maximises the therapeutic effect) can be achieved by careful selection of the degree of hindrance on either side of the disulphide bond.

The hindrance on either side of the disulphide bond is modulated through introducing one or more methyl groups on either the targeting entity (here, the bicyclic peptide) or toxin side of the molecular construct.

In one embodiment, the cytotoxic agent and linker is selected from any combinations of those described in WO 2016/067035 (the cytotoxic agents and linkers thereof are herein incorporated by reference).

Synthesis

The peptides of the present invention may be manufactured synthetically by standard techniques followed by reaction with a molecular scaffold in vitro. When this is performed, standard chemistry may be used. This enables the rapid large scale preparation of soluble material for further downstream experiments or validation. Such methods could be accomplished using conventional chemistry such as that disclosed in Timmerman et al (supra).

Thus, the invention also relates to manufacture of polypeptides or conjugates selected as set out herein, wherein the manufacture comprises optional further steps as explained below. In one embodiment, these steps are carried out on the end product polypeptide/conjugate made by chemical synthesis.

Optionally amino acid residues in the polypeptide of interest may be substituted when manufacturing a conjugate or complex.

Peptides can also be extended, to incorporate for example another loop and therefore introduce multiple specificities.

To extend the peptide, it may simply be extended chemically at its N-terminus or C-terminus or within the loops using orthogonally protected lysines (and analogues) using standard solid phase or solution phase chemistry. Standard (bio)conjugation techniques may be used to introduce an activated or activatable N- or C-terminus. Alternatively additions may be made by fragment condensation or native chemical ligation e.g. as described in (Dawson et al. 1994. Synthesis of Proteins by Native Chemical Ligation. Science 266:776-779), or by enzymes, for example using subtiligase as described in (Chang et al Proc Natl Acad Sci USA. 1994 Dec. 20; 91(26):12544-8 or in Hikari et al Bioorganic & Medicinal Chemistry Letters Volume 18, Issue 22, 15 Nov. 2008, Pages 6000-6003).

Alternatively, the peptides may be extended or modified by further conjugation through disulphide bonds. This has the additional advantage of allowing the first and second peptide to dissociate from each other once within the reducing environment of the cell. In this case, the molecular scaffold (e.g. TATA) could be added during the chemical synthesis of the first peptide so as to react with the three cysteine groups; a further cysteine or thiol could then be appended to the N or C-terminus of the first peptide, so that this cysteine or thiol only reacted with a free cysteine or thiol of the second peptide, forming a disulphide—linked bicyclic peptide-peptide conjugate.

Similar techniques apply equally to the synthesis/coupling of two bicyclic and bispecific macrocycles, potentially creating a tetraspecific molecule.

Furthermore, addition of other functional groups or effector groups may be accomplished in the same manner, using appropriate chemistry, coupling at the N- or C-termini or via side chains. In one embodiment, the coupling is conducted in such a manner that it does not block the activity of either entity.

Pharmaceutical Compositions

According to a further aspect of the invention, there is provided a pharmaceutical composition comprising a peptide ligand or a drug conjugate as defined herein in combination with one or more pharmaceutically acceptable excipients.

Generally, the present peptide ligands will be utilised in purified form together with pharmacologically appropriate excipients or carriers. Typically, these excipients or carriers include aqueous or alcoholic/aqueous solutions, emulsions or suspensions, including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) Remington's Pharmaceutical Sciences, 16th Edition).

The peptide ligands of the present invention may be used as separately administered compositions or in conjunction with other agents. These can include antibodies, antibody fragments and various immunotherapeutic drugs, such as cylcosporine, methotrexate, adriamycin or cisplatinum and immunotoxins. Pharmaceutical compositions can include "cocktails" of various cytotoxic or other agents in conjunction with the protein ligands of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, the peptide ligands of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. Preferably, the pharmaceutical compositions according to the invention will be administered by inhalation. The dosage and frequency of administration will depend on the age, sex and condition of the patient, concurrent administration of other drugs, counterindications and other parameters to be taken into account by the clinician.

The peptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that levels may have to be adjusted upward to compensate.

The compositions containing the present peptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected peptide ligand per kilogram of body weight, with doses of 0.05 to 2.0 mg/kg/dose being more commonly used. For prophylactic applications, compositions containing the present peptide ligands or cocktails thereof may also be administered in similar or slightly lower dosages.

A composition containing a peptide ligand according to the present invention may be utilised in prophylactic and therapeutic settings to aid in the alteration, inactivation, killing or removal of a select target cell population in a mammal. In addition, the peptide ligands described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

Therapeutic Uses

The bicyclic peptides of the invention have specific utility as CD137 binding agents.

CD137 is a member of the tumour necrosis factor (TNF) receptor family. Its alternative names are tumour necrosis factor receptor superfamily member 9 (TNFRSF9), 4-IBB and induced by lymphocyte activation (ILA). CD137 can be expressed by activated T cells, but to a larger extent on CD8+ than on CD4+ T cells. In addition, CD137 expression is found on dendritic cells, follicular dendritic cells, natural killer cells, granulocytes and cells of blood vessel walls at sites of inflammation. One characterized activity of CD137 is its costimulatory activity for activated T cells. Crosslinking of CD137 enhances T cell proliferation, IL-2 secretion, survival and cytolytic activity. Further, it can enhance immune activity to eliminate tumours in mice. CD137 is a T-cell costimulatory receptor induced on TCR activation (Nam et al., Curr. Cancer Drug Targets, 5:357-363 (2005); Waits et al., Annu. Rev, Immunol., 23:23-68 (2005)). In addition to its expression on activated CD4+ and CD8+ T cells, CD137 is also expressed on CD4+CD25+ regulatory T cells, natural killer (NK) and NK-T cells, monocytes, neutrophils, and dendritic cells. Its natural ligand, CD137L, has been described on antigen-presenting cells including B cells, monocyte/macrophages, and dendritic cells (Watts et al. Annu. Rev. Immunol, 23:23-68 (2005)). On interaction with its ligand, CD137 leads to increased TCR-induced T-cell proliferation, cytokine production, functional maturation, and prolonged CD8+ T-cell survival (Nam et al, Curr. Cancer Drug Targets, 5:357-363 (2005), Watts et al., Annu. Rev. Immunol, 23:23-68 (2005)).

Signalling through CD137 by either CD137L or agonistic monoclonal antibodies (mAbs) against CD137 leads to increased TCR-induced T cell proliferation, cytokine production and functional maturation, and prolonged CD8+ T cell survival. These effects result from: (1) the activation of the NF-κB, c-Jun NH2-terminal kinase/stress-activated protein kinase (JNK/SAPK), and p38 mitogen-activated protein kinase (MAPK) signalling pathways, and (2) the control of anti-apoptotic and cell cycle-related gene expression.

Experiments performed in both CD137 and CD137L-deficient mice have additionally demonstrated the importance of CD137 costimulation in the generation of a fully competent T cell response.

IL-2 and IL-15 activated NK cells express CD137, and ligation of CD137 by agonistic mAbs stimulates NK cell proliferation and IFN-γ secretion, but not their cytolytic activity.

Furthermore, CD137-stimulated NK cells promote the expansion of activated T cells in vitro.

In accordance with their costimulatory function, agonist mAbs against CD137 have been shown to promote rejection of cardiac and skin allografts, eradicate established tumours, broaden primary antiviral CD8+ T cell responses, and increase T cell cytolytic potential. These studies support the view that CD137 signalling promotes T cell function which may enhance immunity against tumours and infection.

Polypeptide ligands selected according to the method of the present invention may be employed in in vivo therapeutic and prophylactic applications, in vitro and in vivo diagnostic applications, in vitro assay and reagent applications, and the like. Ligands having selected levels of specificity are useful in applications which involve testing in non-human animals, where cross-reactivity is desirable, or in diagnostic applications, where cross-reactivity with homologues or paralogues needs to be carefully controlled. In some applications, such as vaccine applications, the ability to elicit an immune response to predetermined ranges of antigens can be exploited to tailor a vaccine to specific diseases and pathogens.

Substantially pure peptide ligands of at least 90 to 95% homogeneity are preferred for administration to a mammal, and 98 to 99% or more homogeneity is most preferred for pharmaceutical uses, especially when the mammal is a human. Once purified, partially or to homogeneity as desired, the selected polypeptides may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, NY).

According to a further aspect of the invention, there is provided a peptide ligand or a drug conjugate as defined herein, for use in preventing, suppressing or treating a disease or disorder mediated by CD137.

According to a further aspect of the invention, there is provided a method of preventing, suppressing or treating a disease or disorder mediated by CD137, which comprises administering to a patient in need thereof an effector group and drug conjugate of the peptide ligand as defined herein.

In one embodiment, the CD137 is mammalian CD137. In a further embodiment, the mammalian CD137 is human CD137 (hCD137).

In one embodiment, the disease or disorder mediated by CD137 is selected from cancer, infection and inflammation. In a further embodiment, the disorder or disease mediated by CD137 is selected from cancer.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the oesophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukaemias, lymphomas) and pre-malignant haematological disorders and disorders of borderline malignancy including haematological malignancies and related conditions of lymphoid lineage (for example acute lymphocytic leukaemia [ALL], chronic lymphocytic leukaemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenousleukemia [AML], chronic myelogenousleukemia [CML], chronic myelomonocyticleukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocyticleukaemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcomaprotuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wlms tumour, and primitive neuroectodermal tumours); or syndromes, congenital or otherwise, which leave the patient susceptible to malignancy (for example *Xeroderma Pigmentosum*).

In a further embodiment, the cancer is selected from a hematopoietic malignancy such as selected from: non-Hodgkin's lymphoma (NHL), Burkitt's lymphoma (BL), multiple myeloma (MM), B chronic lymphocytic leukaemia (B-CLL), B and T acute lymphocytic leukaemia (ALL), T cell lymphoma (TCL), acute myeloid leukaemia (AML), hairy cell leukaemia (HCL), Hodgkin's Lymphoma (HL), and chronic myeloid leukaemia (CML).

References herein to the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available. The use of animal model systems is facilitated by the present invention, which allows the development of polypeptide ligands which can cross react with human and animal targets, to allow the use of animal models.

The invention is further described below with reference to the following examples.

EXAMPLES

Materials and Methods
Peptide Synthesis

Peptide synthesis was based on Fmoc chemistry, using a Symphony peptide synthesiser manufactured by Peptide Instruments and a Syro II synthesiser by MultiSynTech. Standard Fmoc-amino acids were employed (Sigma, Merck), with appropriate side chain protecting groups: where applicable standard coupling conditions were used in each case, followed by deprotection using standard methodology. Peptides were purified using HPLC and following isolation they were modified with 1,3,5-triacryloylhexahydro-1,3,5-triazine (TATA, Sigma). For this, linear peptide was diluted with 50:50 MeCN:$H_2O$ up to ~35 mL, ~500 μL of 100 mM TATA in acetonitrile was added, and the reaction was initiated with 5 mL of 1 M $NH_4HCO_3$ in $H_2O$. The reaction was allowed to proceed for ~30 –60 min at RT, and lyophilised once the reaction had completed (judged by MALDI). Once completed, 1 ml of 1M L-cysteine hydrochloride monohydrate (Sigma) in $H_2O$ was added to the reaction for ~60 min at RT to quench any excess TATA.

Following lyophilisation, the modified peptide was purified as above, while replacing the Luna C8 with a Gemini C18 column (Phenomenex), and changing the acid to 0.1% trifluoroacetic acid. Pure fractions containing the correct TATA-modified material were pooled, lyophilised and kept at −20° C. for storage.

All amino acids, unless noted otherwise, were used in the L-configurations.

In some cases, peptides are converted to activated disulphides prior to coupling with the free thiol group of a toxin using the following method; a solution of 4-methyl(succinimidyl 4-(2-pyridylthio)pentanoate) (100 mM) in dry DMSO (1.25 mol equiv) was added to a solution of peptide (20 mM) in dry DMSO (1 mol equiv). The reaction was well mixed and DIPEA (20 mol equiv) was added. The reaction was monitored by LC/MS until complete.

Abbreviations

Aad 2-Aminoadipic acid
Abu 2-Aminobutyric acid
Ac5c Aminocyclopentanecarboxylic acid
Ahp Aminoheptanoic acid
Aib aminoisobutyric acid
Me-Ala methyl alanine
NMe-Ala N-methyl alanine
tBuAla t-butyl-Alanine
Api Amino pimelic acid
Aze Azetidine
4,4-BPA 4,4-Biphenylalanine
CF3G Trifluoromethyl-Alanine
Cha 3-cyclohexyl alanine
Chg L-Cyclohexyl glycine
Cit citrulline
H-Cys homocysteine
Dap diaminopimelic acid
Fl fluorescein
NMeGlu N-methyl glutamic acid
HGln homoglutamine
HyP hydroxyproline
Hleu homoleucine
Nle norleucine
Nal naphthylalanine
NMeIle N-Methyl-lsoleucine
Oic octahydroindolecarboxylic acid
Oxa oxazolidine-4-carboxylic acid
Pal pyridylalanine
Pen penicillamine
pCaPhe para-Carbamoyl-Phenylalanine
pCoPhe para-Carboxy-Phenylalanine
Phg phenylglycine
HPhe homophenylalanine
FPhe fluorophenylalanine
MePhe methyl phenylalanine
MeOPhe methoxy phenylalanine
tBuPhe t-butyl phenylalanine
NO2Phe nitro phenylalanine
BrPhe bromo phenylalanine
Pip Pipecolic acid
5,5-dmP 5,5-Dimethyl-L-Proline
Sar sarcosine
HSe(me) Homoserine(Me)
TetraZ tetrazole alanine
NMeTyr N-methyl tyrosine
Biological Data 1. CD137 Direct Binding Assay Affinity of the peptides of the invention for human CD137 (Ki) was determined using a fluorescence polarisation assay, in accordance with the methods disclosed in WO 2016/067035. Peptides of the invention were labelled with a fluorescent tag (fluorescein, Fl) and diluted to 2.5 nM in 50 mM HEPES with 100 mM NaCl and 0.05% tween pH 7.5. CD137 protein was titrated starting at 3 μM in the same assay buffer as the peptide to assay 1 nM peptide in a total volume of 25 μL in black walled and bottomed low bind low volume 384 well plates. The assay was typically set up by adding 5 μL assay buffer, 10 μL CD137 protein then 10 μL fluorescent peptide. The concentrations of CD137 protein were 1 in 2 serial dilutions to give 12 different concentrations starting at 3 μM. Measurements were conducted on a BMG PHERAstar FS equipped with an FP 485 520 520 optic module at 25° C. with 200 flashes per well and a positioning delay of 0.1 second. Alternatively, the measurements were performed using Envision (PerkinElmer) equipped with FITC FP Dual Enh mirror, set to 30 flashes. Each well was measured every 5 minutes for 60 minutes. The gain used for analysis was determined for each tracer at the end of the 60 minutes where there was no protein in the well. The mP were fit to a standard 1:1 binding model with a quadratic equation to generate a Kd value. Selected peptides of the invention were tested in the above mentioned assay and the results are shown in Tables 1 to 3:

TABLE 1

Direct Binding Results with Selected Peptides

| Peptide Number | SEQ ID NO: | Peptide Reference | Sequence | Kd nM |
|---|---|---|---|---|
| BCY633 | 42 | (B-Ala)-Sar5-(74-01-00) | [B-Ala]-Sar5-ACIEEGQYCYRDMYMCA | 1841 |
| BCY634 | 43 | Ac-(74-01-00)-Sar6-K(FI) | [Ac]ACIEEGQYCYRDMYMCA-Sar6-K(FI) | 1376 |
| BCY636 | 44 | (74-01-01)-Sar6-K(FI) | ACIEEGQYCYADPYMCA-Sar6-K(FI) | 123.9 |
| BCY635 | 45 | (B-Ala)-Sar5-(74-01-01) | [B-Ala]-Sar5-ACIEEGQYCYADPYMCA | 126 |
| BCY638 | 46 | (74-01-02)-Sar6-K | ACIEEGQYCYADPYYCASar6-K | 192.5 |
| BCY637 | 47 | (B-Ala)-Sar5-(74-01-02) | [B-Ala]-Sar5-ACIEEGQYCYADPYYCA | 122 |
| BCY639 | 48 | (74-01-03)-Sar6-K | ACIEEGQYCYSDPYYCA-Sar6-K | 229 |
| BCY640 | 49 | (74-01-04)-Sar6-K | ACIEEGQYCFADPYMCA-Sar6-K | 84 |
| BCY641 | 50 | G-Sar5-(74-01-04) | G-Sar5-ACIEEGQYCFADPYMCA | 152.5 |
| BCY7238 | 51 | Ac-(74-01-04) Lys1(PEG12) | Ac-CK(Peg12)EEGQYCFADPYMC | >>3000 |
| BCY7239 | 52 | Ac-(74-01-04) Lys2(PEG12) | Ac-CIK(Peg12)EGQYCFADPYMC | 579 |
| BCY7240 | 53 | Ac-(74-01-04) Lys3(PEG12) | Ac-CIEK(Peg12)GQYCFADPYMC | 384 |
| BCY7241 | 54 | Ac-(74-01-04) Lys4(PEG12) | Ac-CIEEK(Peg12)QYCFADPYMC | >>3000 |
| BCY7242 | 55 | Ac-(74-01-04) Lys5(PEG12) | Ac-CIEEGK(Peg12)YCFADPYMC | 48.3 |
| BCY7243 | 56 | Ac-(74-01-04) Lys6(PEG12) | Ac-CIEEGQK(Peg12)CFADPYMC | >>3000 |
| BCY7244 | 57 | Ac-(74-01-04) Lys7(PEG12) | Ac-CIEEGQYCK(Peg12)ADPYMC | 296 |
| BCY7245 | 58 | Ac-(74-01-04) Lys8(PEG12) | Ac-CIEEGQYCFK(Peg12)DPYMC | 777 |
| BCY7246 | 59 | Ac-(74-01-04) Lys9(PEG12) | Ac-CIEEGQYCFAK(Peg12)PYMC | >>3000 |
| BCY7247 | 60 | Ac-(74-01-04) Lys10(PEG12) | Ac-CIEEGQYCFADK(Peg12)YMC | 239 |
| BCY7248 | 61 | Ac-(74-01-04) Lys11(PEG12) | Ac-CIEEGQYCFADPK(Peg12)MC | 744 |
| BCY7249 | 62 | Ac-(74-01-04) Lys12(PEG12) | Ac-CIEEGQYCFADPYK(Peg12)C | 288 |
| BCY7416 | 63 | Ac-(74-01-04) D-Lys4 (PEG12) Nle12 | [Ac]CIEE[dK(PEG12FI)]QYCFADPY[Nle]C | 50.5 |
| BCY7519 | 64 | (74-01-04) Nle12 | ACIEEGQYCFADPY[Nle]CA | 61 |
| BCY7520 | 65 | (Peg12)-(74-01-04) Nle12 | [Peg12]-ACIEEGQYCFADPY[Nle]CA | 121 |
| BCY642 | 66 | (74-01-05)-Sar6-K | ACIEEGQYCYADHQLCA-Sar6-K | 245.5 |
| BCY643 | 67 | (74-01-06)-Sar6-K | ACIEEGQYCHADPYYCA-Sar6-K | 148 |
| BCY644 | 68 | (74-01-07)-Sar6-K | ACIEEGQYCHADPYFCA-Sar6-K | 145 |
| BCY645 | 69 | (74-01-08)-Sar6-K | ACIEEGQYCYADHYMCA-Sar6-K | 146.5 |
| BCY646 | 70 | (74-01-09)-Sar6-K | ACIEEGQYCYADPYLCA-Sar6-K | 105 |
| BCY647 | 71 | (74-01-09-T03)-Sar6-K(FI) | ACIEEGQYCYADPYLCSVG-Sar6-K | 391.5 |
| BCY648 | 72 | (B-Ala)-Sar5-(74-01-09-T03) | (FI)G-Sar5-ACIEEGQYCYADPYLCSVG | 228 |

TABLE 1-continued

Direct Binding Results with Selected Peptides

| Peptide Number | SEQ ID NO: | Peptide Reference | Sequence | Kd nM |
|---|---|---|---|---|
| BCY649 | 73 | (74-01-10)-Sar6-K | ACIEEGQYCYSDPYLCA-Sar6-K | 207 |
| BCY650 | 74 | (74-01-11)-Sar6-K | ACIEEGQYCFADPYLCA-Sar6-K | 86.5 |
| BCY652 | 75 | (74-01-13)-Sar6-K | ACIEEGQYCHADPYMCA-Sar6-K | 142 |
| BCY653 | 76 | (74-01-14)-Sar6-K | ACIEEGQYCHADPQMCA-Sar6-K | 383 |
| BCY655 | 77 | (74-01-16)-Sar6-K | ACDIGPPYCYRDMYMCA-Sar6-K | 1337 |
| BCY656 | 78 | (74-01-17)-Sar6-K | ADIGPPYCYADPYMCA-Sar6-K | 240 |
| BCY7251 | 79 | (74-01-19-N002)-Sar6-K | ACLDGPFCFADPYMCA-Sar6-K | 193 |
| BCY7253 | 80 | (74-01-20-N002)-Sar6-K | ACLDEGPYCFADPYFCA-Sar6-K | 183 |
| BCY7255 | 81 | (74-01-21-N002)-Sar6-K | ACINEGPYCFADPYMCA-Sar6-K | 136 |
| BCY7257 | 82 | (74-01-22-N002)-Sar6-K | ACIEQGPFCFADPYMCA-Sar6-K | 109 |
| BCY7259 | 83 | (74-01-23-N002)-Sar6-K | ACVEEGPFCFADPYYCA-Sar6-K | 105 |
| BCY7261 | 84 | (74-01-24-N002)-Sar6-K | ACLDEGPFCFSDPYMCA-Sar6-K | 453 |
| BCY657 | 85 | (B-Ala)-Sar5-(74-02-00) | [B-Ala]-Sar5-ACDEWGLFCIPHSDCA | 3621 |
| BCY659 | 86 | (74-02-01)-Sar6-K | ACDEWGLYCFAHPDCA-Sar6-K | 1041 |
| BCY7119 | 87 | (74-13-00-T02)-Sar6-K | ACLDPGPYCYADPYMCTFH-Sar6-K | 144 |
| BCY660 | 88 | (74-19-00-T01)-Sar6-K | ACIEPGPFCYADPYMCNRV-Sar6-K | 183.5 |
| BCY661 | 89 | (B-Ala)-Sar5-(74-19-00-T01) | G-Sar5-ACIEPGPFCYADPYMCNRV | 412 |
| BCY7120 | 90 | (74-20-00-T01)-Sar6-K | ACLEPGPYCYADPYMCTHL-Sar6-K | 160 |
| BCY7122 | 91 | (74-22-03-N004)-Sar6-K | ACLPPGPYCFPDPYFCA-Sar6-K | 147 |

TABLE 2

Alanine Scan Results

| Peptide Number | SEQ ID NO: | Peptide Reference | Sequence | Kd nM |
|---|---|---|---|---|
| BCY7151 | 92 | [PEG3]-(74-01-04) Nle12 | [PEG3]-ACIEEGQYCFADPY[Nle]CA | 24.0 |
| BCY7283 | 93 | [PEG3]-(74-01-04) Ala1 Nle12 | [PEG3]-ACAEEGQYCFADPY(Nle)CA | 231 |
| BCY7284 | 94 | [PEG3]-(74-01-04) Ala2 Nle12 | [PEG3]-ACIAEGQYCFADPY(Nle)CA | 160 |
| BCY7285 | 95 | [PEG3]-(74-01-04) Ala3 Nle12 | [PEG3]-ACIEAGQYCFADPY(Nle)CA | 185 |
| BCY7286 | 96 | [PEG3]-(74-01-04) Ala4 Nle12 | [PEG3]-ACIEEAQYCFADPY(Nle)CA | 2568 |
| BCY7287 | 97 | [PEG3]-(74-01-04) Ala5 Nle12 | [PEG3]-ACIEEGAYCFADPY(Nle)CA | 25.5 |
| BCY7288 | 98 | [PEG3]-(74-01-04) Ala6 Nle12 | [PEG3]-ACIEEGQACFADPY(Nle)CA | 2322 |
| BCY7289 | 99 | [PEG3]-(74-01-04) Ala7 Nle12 | [PEG3]-ACIEEGQYCAADPY(Nle)CA | 904 |
| BCY7290 | 100 | [PEG3]-(74-01-04) Ala9 Nle12 | [PEG3]-ACIEEGQYCFAAPY(Nle)CA | >>3000 |
| BCY7292 | 101 | [PEG3]-(74-01-04) Ala11 Nle12 | [PEG3]-ACIEEGQYCFADPA(Nle)CA | 593 |
| BCY7293 | 102 | [PEG3]-(74-01-04) Ala12 | [PEG3]-ACIEEGQYCFADPYACA | 417 |
| BCY7294 | 103 | [PEG3]-(74-01-04) D-Ala1 Nle12 | [PEG3]-ACaEEGQYCFADPY(Nle)CA | >>3000 |
| BCY7295 | 104 | [PEG3]-(74-01-04) D-Ala2 Nle12 | [PEG3]-ACIaEGQYCFADPY(Nle)CA | >>3000 |

TABLE 2-continued

Alanine Scan Results

| Peptide Number | SEQ ID NO: | Peptide Reference | Sequence | Kd nM |
|---|---|---|---|---|
| BCY7296 | 105 | [PEG3]-(74-01-04) D-Ala3 Nle12 | [PEG3]-ACIEaGQYCFADPY(Nle)CA | >>3000 |
| BCY7297 | 106 | [PEG3]-(74-01-04) D-Ala4 Nle12 | [PEG3]-ACIEEaQYCFADPY(Nle)CA | 25.2 |
| BCY7298 | 107 | [PEG3]-(74-01-04) D-Ala5 Nle12 | [PEG3]-ACIEEGaYCFADPY(Nle)CA | 756 |
| BCY7299 | 108 | [PEG3]-(74-01-04) D-Ala6 Nle12 | [PEG3]-ACIEEGQaCFADPY(Nle)CA | >>3000 |
| BCY7300 | 109 | [PEG3]-(74-01-04) D-Ala7 Nle12 | [PEG3]-ACIEEGQYCaADPY(Nle)CA | >>3000 |
| BCY7301 | 110 | [PEG3]-(74-01-04) D-Ala8 Nle12 | [PEG3]-ACIEEGQYCFaDPY(Nle)CA | >>3000 |
| BCY7302 | 111 | [PEG3]-(74-01-04) D-Ala9 Nle12 | [PEG3]-ACIEEGQYCFAaPY(Nle)CA | >>3000 |
| BCY7303 | 112 | [PEG3]-(74-01-04) D-Ala10 Nle12 | [PEG3]-ACIEEGQYCFADaY(Nle)CA | 968 |
| BCY7304 | 113 | [PEG3]-(74-01-04) D-Ala11 Nle12 | [PEG3]-ACIEEGQYCFADPa(Nle)CA | >>3000 |
| BCY7305 | 114 | [PEG3]-(74-01-04) D-Ala12 | [PEG3]-ACIEEGQYCFADPYACA | >>3000 |

TABLE 3

Direct Binding Results with Selected Peptides

| Peptide Number | SEQ ID NO: | Peptide Reference | Sequence | Kd nM |
|---|---|---|---|---|
| BCY7151 | 92 | [PEG3]-(74-01-04) Nle12 | [PEG3]-ACIEEGQYCFADPY[Nle]CA | 24.0 |
| BCY7152 | 115 | [PEG3]-(74-01-04) Leu1 Nle12 | [PEG3]-ACLEEGQYCFADPY[Nle]CA | 55.1 |
| BCY7153 | 116 | [PEG3]-(74-01-04) Nle1 Nle12 | [PEG3]-AC[Nle]EEGQYCFADPY[Nle]CA | 122.6 |
| BCY7154 | 117 | [PEG3]-(74-01-04) Chg1 Nle12 | [PEG3]-AC-Chg-EEGQYCFADPY[Nle]CA | 20.3 |
| BCY7155 | 118 | [PEG3]-(74-01-04) Cha1 Nle12 | [PEG3]-AC-Cha-EEGQYCFADPY[Nle]CA | 175.5 |
| BCY7156 | 119 | [PEG3]-(74-01-04) Pro2 Nle12 | [PEG3]-ACIPEGQYCFADPY[Nle]CA | 10.4 |
| BCY7157 | 120 | [PEG3]-(74-01-04) Asp2 Nle12 | [PEG3]-ACIDEGQYCFADPY[Nle]CA | 26.2 |
| BCY7158 | 121 | [PEG3]-(74-01-04) Aad2 Nle12 | [PEG3]-ACI-Aad-EGQYCFADPY[Nle]CA | 22.3 |
| BCY7159 | 122 | [PEG3]-(74-01-04) Api2 Nle12 | [PEG3]-ACI-Api-EGQYCFADPY[Nle]CA | 58.0 |
| BCY7160 | 123 | [PEG3]-(74-01-04) Pro3 Nle12 | [PEG3]-ACIEPGQYCFADPY[Nle]CA | 68.1 |
| BCY7161 | 124 | [PEG3]-(74-01-04) Asp3 Nle12 | [PEG3]-ACIEDGQYCFADPY[Nle]CA | 282.1 |
| BCY7162 | 125 | [PEG3]-(74-01-04) Aad3 Nle12 | [PEG3]-ACIE-Aad-GQYCFADPY[Nle]CA | 39.8 |
| BCY7163 | 126 | [PEG3]-(74-01-04) Api3 Nle12 | [PEG3]-ACIE-Api-GQYCFADPY[Nle]CA | 126.3 |
| BCY7164 | 127 | [PEG3]-(74-01-04) Sar4 Nle12 | [PEG3]-ACIEE-Sar-QYCFADPY[Nle]CA | 326.0 |
| BCY7165 | 128 | [PEG3]-(74-01-04) D-Lys4 Nle12 | [PEG3]-ACIEE-DLys-QYCFADPY[Nle]CA | 24.0 |
| BCY7166 | 129 | [PEG3]-(74-01-04) D-Phe4 Nle12 | [PEG3]-ACIEE-DPhe-QYCFADPY[Nle]CA | 10.0 |
| BCY7167 | 130 | [PEG3]-(74-01-04) D-Glu4 Nle12 | [PEG3]-ACIEE-DGlu-QYCFADPY[Nle]CA | 31.9 |
| BCY7168 | 131 | [PEG3]-(74-01-04) D-Gln4 Nle12 | [PEG3]-ACIEE-DGln-QYCFADPY[Nle]CA | 15.7 |
| BCY7169 | 132 | [PEG3]-(74-01-04) D-Leu4 Nle12 | [PEG3]-ACIEE-DLeu-QYCFADPY[Nle]CA | 46.1 |
| BCY7170 | 133 | [PEG3]-(74-01-04) D-Ser4 Nle12 | [PEG3]-ACIEE-DSer-QYCFADPY[Nle]CA | 13.9 |
| BCY7172 | 134 | [PEG3]-(74-01-04) N-Me-D-Ala4 Nle12 | [PEG3]-ACIEE-MeDala-QYCFADPY[Nle]CA | 546.4 |
| BCY7173 | 135 | [PEG3]-(74-01-04) Aib4 Nle12 | [PEG3]-ACIEE-Aib-QYCFADPY[Nle]CA | 414.0 |
| BCY7174 | 136 | [PEG3]-(74-01-04) Pro5 Nle12 | [PEG3]-ACIEEGPYCFADPY[Nle]CA | 6.13 |

TABLE 3-continued

Direct Binding Results with Selected Peptides

| Peptide Number | SEQ ID NO: | Peptide Reference | Sequence | Kd nM |
|---|---|---|---|---|
| BCY7175 | 137 | [PEG3]-(74-01-04) Phe6 Nle12 | [PEG3]-ACIEEGQFCFADPY[Nle]CA | 25.3 |
| BCY7176 | 138 | [PEG3]-(74-01-04) 2MePhe6 Nle12 | [PEG3]-ACIEEGQ-2MeF-CFADPY[Nle]CA | 88.4 |
| BCY7177 | 139 | [PEG3]-(74-01-04) 3MePhe6 Nle12 | [PEG3]-ACIEEGQ-3MeF-CFADPY[Nle]CA | 43.7 |
| BCY7178 | 140 | [PEG3]-(74-01-04) 4MePhe6 Nle12 | [PEG3]-ACIEEGQ-4MeF-CFADPY[Nle]CA | 21.8 |
| BCY7179 | 141 | [PEG3]-(74-01-04) 4FPhe6 Nle12 | [PEG3]-ACIEEGQ-4FF-CFADPY[Nle]CA | 30.5 |
| BCY7180 | 142 | [PEG3]-(74-01-04) 3FPhe6 Nle12 | [PEG3]-ACIEEGQ-3FF-CFADPY[Nle]CA | 54.4 |
| BCY7181 | 143 | [PEG3]-(74-01-04) 2MePhe7 Nle12 | [PEG3]-ACIEEGQYC-2MeF-ADPY[Nle]CA | 86.4 |
| BCY7182 | 144 | [PEG3]-(74-01-04) 3MePhe7 Nle12 | [PEG3]-ACIEEGQYC-3MeF-ADPY[Nle]CA | 63.3 |
| BCY7183 | 145 | [PEG3]-(74-01-04) 4MePhe7 Nle12 | [PEG3]-ACIEEGQYC-4MeF-ADPY[Nle]CA | 34.2 |
| BCY7184 | 146 | [PEG3]-(74-01-04) Phg7 Nle12 | [PEG3]-ACIEEGQYC-PheG-ADPY[Nle]CA | 2813.3 |
| BCY7185 | 147 | [PEG3]-(74-01-04) 4FPhe7 Nle12 | [PEG3]-ACIEEGQYC-4FF-ADPY[Nle]CA | 19.6 |
| BCY7186 | 148 | [PEG3]-(74-01-04) Gly8 Nle12 | [PEG3]-ACIEEGQYCFGDPY[Nle]CA | 244.2 |
| BCY7187 | 149 | [PEG3]-(74-01-04) Ser8 Nle12 | [PEG3]-ACIEEGQYCFSDPY[Nle]CA | 83.9 |
| BCY7188 | 150 | [PEG3]-(74-01-04) Pro8 Nle12 | [PEG3]-ACIEEGQYCFPDPY[Nle]CA | 363.1 |
| BCY7189 | 151 | [PEG3]-(74-01-04) Asn8 Nle12 | [PEG3]-ACIEEGQYCFANPY[Nle]CA | 655.8 |
| BCY7190 | 152 | [PEG3]-(74-01-04) Pip10 Nle12 | [PEG3]-ACIEEGQYCFAD-Pip-Y[Nle]CA | 326.8 |
| BCY7191 | 153 | [PEG3]-(74-01-04) N-Me-Ala10 Nle12 | [PEG3]-ACIEEGQYCFAD-MeAla-Y[Nle]CA | 460.2 |
| BCY7192 | 154 | [PEG3]-(74-01-04) Sar10 Nle12 | [PEG3]-ACIEEGQYCFAD-Sar-Y[Nle]CA | 220.6 |
| BCY7193 | 155 | [PEG3]-(74-01-04) Aib10 Nle12 | [PEG3]-ACIEEGQYCFAD-Aib-Y[Nle]CA | 146.9 |
| BCY7195 | 156 | [PEG3]-(74-01-04) tBuAla1 Nle12 | [PEG3]AC[tBuAla]EEGQYCFADPY[Nle]CA | 15.7 |
| BCY7196 | 157 | [PEG3]-(74-01-04) HLeu1 Nle12 | [PEG3]AC[HLeu]EEGQYCFADPY[Nle]CA | 138.5 |
| BCY7197 | 158 | [PEG3]-(74-01-04) 2FPhe6 Nle12 | [PEG3]ACIEEGQ[2FPhe]CFADPY[Nle]CA | 95.1 |
| BCY7198 | 159 | [PEG3]-(74-01-04) 2FPhe7 Nle12 | [PEG3]ACIEEGQYC[2FPhe]ADPY[Nle]CA | 28.1 |
| BCY7199 | 160 | [PEG3]-(74-01-04) CF3G8 Nle12 | [PEG3]ACIEEGQYCF[CF3G]DPY[Nle]CA | 172.0 |
| BCY7200 | 161 | [PEG3]-(74-01-04) pCoPhe11 Nle12 | [PEG3]ACIEEGQYCFADP[pCoPhe][Nle]CA | 364.6 |
| BCY7201 | 162 | [PEG3]-(74-01-04) pCaPhe11 Nle12 | [PEG3]ACIEEGQYCFADP[pCaPhe][Nle]CA | 533.4 |
| BCY7202 | 163 | [PEG3]-(74-01-04) Gln11 Nle12 | [PEG3]ACIEEGQYCFADPQ[Nle]CA | 216.0 |
| BCY7205 | 164 | [PEG3]-(74-01-04) 2MePhe11 Nle12 | [PEG3]ACIEEGQYCFADP[2MePhe][Nle]CA | 147.3 |
| BCY7206 | 165 | [PEG3]-(74-01-04) 3MePhe11 Nle12 | [PEG3]ACIEEGQYCFADP[3MePhe][Nle]CA | 157.8 |
| BCY7207 | 166 | [PEG3]-(74-01-04) 4MePhe11 Nle12 | [PEG3]ACIEEGQYCFADP[4MePhe][Nle]CA | 185.8 |
| BCY7208 | 167 | [PEG3]-(74-01-04) Cit11 Nle12 | [PEG3]ACIEEGQYCFADP[Cit][Nle]CA | 657.4 |
| BCY7209 | 168 | [PEG3]-(74-01-04) 4FPhe11 Nle12 | [PEG3]ACIEEGQYCFADP[4FPhe][Nle]CA | 154.1 |
| BCY7210 | 169 | [PEG3]-(74-01-04) tBuAla12 | [PEG3]ACIEEGQYCFADPY[tBuAla]CA | 70.0 |
| BCY7211 | 170 | [PEG3]-(74-01-04) HLeu12 | [PEG3]ACIEEGQYCFADPY[HLeu]CA | 39.1 |
| BCY7212 | 171 | [PEG3]-(74-01-04) Ile12 | [PEG3]ACIEEGQYCFADPYICA | 140.3 |
| BCY7213 | 172 | [PEG3]-(74-01-04) Cha12 | [PEG3]ACIEEGQYCFADPY[Cha]CA | 62.1 |
| BCY7214 | 173 | [PEG3]-(74-01-04) Phe12 | [PEG3]ACIEEGQYCFADPYFCA | 50.1 |

TABLE 3-continued

Direct Binding Results with Selected Peptides

| Peptide Number | SEQ ID NO: | Peptide Reference | Sequence | Kd nM |
|---|---|---|---|---|
| BCY7215 | 174 | [PEG3]-(74-01-04) 2MePhe12 | [PEG3]ACIEEGQYCFADPY[2MePhe]CA | 58.2 |
| BCY7216 | 175 | [PEG3]-(74-01-04) 3MePhe12 | [PEG3]ACIEEGQYCFADPY[3MePhe]CA | 88.0 |
| BCY7217 | 176 | [PEG3]-(74-01-04) 4MePhe12 | [PEG3]ACIEEGQYCFADPY[4MePhe]CA | 134.2 |
| BCY7218 | 177 | [PEG3]-(74-01-04) Cys1Pen Nle12 | [PEG3]A[Pen]IEEGQYCFADPY[Nle]CA | 40.7 |
| BCY7219 | 178 | [PEG3]-(74-01-04) Cys2Pen Nle12 | [PEG3]ACIEEGQY[Pen]FADPY[Nle]CA | 482.1 |
| BCY7220 | 179 | [PEG3]-(74-01-04) Cys3Pen Nle12 | [PEG3]ACIEEGQYCFADPY[Nle][Pen]A | 2465.1 |
| BCY7221 | 180 | [PEG3]-(74-01-04) Cys1HCys Nle12 | [PEG3]A[HCys]IEEGQYCFADPY[Nle]CA | 50.8 |
| BCY7222 | 181 | [PEG3]-(74-01-04) Cys2HCys Nle12 | [PEG3]ACIEEGQY[HCys]FADPY[Nle]CA | 1493.1 |
| BCY7223 | 182 | [PEG3]-(74-01-04) Cys3HCys Nle12 | [PEG3]ACIEEGQYCFADPY[Nle][HCys]A | 279.6 |
| BCY7224 | 183 | [PEG3]-(74-01-04) 3FPhe7 Nle12 | [PEG3]ACIEEGQYC[3FPhe]ADPY[Nle]CA | 39.8 |
| BCY7306 | 184 | [PEG3]-(74-01-04) TetraZ2 Nle12 | [PEG3]-ACI[TetraZ]EGQYCFADPY[Nle]CA | 289.3 |
| BCY7308 | 185 | [PEG3]-(74-01-04) TetraZ9 Nle12 | [PEG3]-ACIEEGQYCFA[TetraZ]PY[Nle]CA | 842.1 |
| BCY7309 | 186 | [PEG3]-(74-01-04) HGln11 Nle12 | [PEG3]-ACIEEGQYCFADP[HGln][Nle]CA | 536.9 |
| BCY7310 | 187 | [PEG3]-(74-01-04) Ahp1 Nle12 | [PEG3]-AC[Ahp]EEGQYCFADPY[Nle]CA | 278.5 |
| BCY7311 | 188 | [PEG3]-(74-01-04) Ahp12 | [PEG3]-ACIEEGQYCFADPY[Ahp]CA | 19.2 |

2. CD137 Biacore Experiments (a) Amine Coupled CD137 Target Assay Description

Biacore experiments were performed to determine $k_a$ ($M^{-1} s^{-1}$), $k_d$ ($s^{-1}$), $K_D$ (nM) values of peptides binding to human CD137 (AcroBiosystems) protein. CD137 protein was diluted and immobilised using the standard amine coupling procedure to chip CM5 (#BR-1005-30). CD137 protein was diluted to 10 ug/ml in NaAc pH 5.5 and used for coupling. Ethanolamine is then injected to deactivate remaining active esters.

The CD137 protein was immobilise at 180 RUs of CD137 protein to generate the maximum theoretical binding response with a peptide of 2500 MW will be ~25 RUs. A blank immobilisation of the reference flow cell (Fc1 or Fc3) is performed when amine coupling, following exactly the same procedure but with no injection of protein target. The peptides were tested at starting concentrations of 300-450 nM and diluted in ½ dilutions series. The DMSO concentration was adjusted to remain constant.

The peptide binding kinetic analysis was performed as follows at flow rate 50 µl/min, 200 sec association, 600 sec dissociation and 60 sec stabilization. The Bicyclic peptides were fitted using the 1:1 model Biacore T200 Evaluation software.

Selected peptides of the invention were tested in the above mentioned assay and the results are shown in Table 4:

TABLE 4

SPR Data for Selected Peptides of the Invention

| Peptide Number | SEQ ID NO: | Peptide Reference | Sequence | $K_D$ nM |
|---|---|---|---|---|
| BCY592 | 189 | 74-01-04 | ACIEEGQYCFADPYMCA | 70.9 |
| BCY589 | 190 | 74-01-01-T01 | HEHCIEEGQYCYADPYMCA | 124.1 |
| BCY599 | 191 | 74-01-11 | ACIEEGQYCFADPYLCA | 191.4 |
| BCY631 | 192 | 74-22-03 | ACLPPGPYCFPDPYFCA | 92.3 |

(b) Biotinylated CD137 Target Assay Description

Biacore experiments were performed to determine $k_a$ ($M^{-1} s^{-1}$), $k_d$ ($s^{-1}$), $K_D$ (nM) values of peptides binding to human CD137 protein. Recombinant human CD137 homotrimer (R&D systems) was resuspended in PBS and biotinylated using EZ-Link™ Sulfo-NHS-LC-LC-Biotin reagent (Thermo Fisher) as per the manufacturer's suggested protocol. The protein was desalted to remove uncoupled biotin using spin columns into PBS.

For analysis of binding, a Biacore T200 instrument was used utilising a XanTec CMD500D chip. Streptavidin was immobilized on the chip using standard amine-coupling chemistry at 25° C. with HBS-N (10 mM HEPES, 0.15 M NnCl, pH 7.4) as the running buffer. Briefly, the carboxymethyl dextran surface was activated with a 7 min injection of a 1:1 ratio of 0.4 M 1-ethyl-3-(3-dimethylaminopropyl) carbodiimide hydrochloride (EDC)/0.1 M N-hydroxy succinimide (NHS) at a flow rate of 10 µl/min. For capture of streptavidin, the protein was diluted to 0.2 mg/ml in 10 mM sodium acetate (pH 4.5) and captured by injecting 120 µl of onto the activated chip surface. Residual activated groups were blocked with a 7 min injection of 1 M ethanolamine (pH 8.5) and biotinylated CD137 captured to a level of 800-1800 RU. Buffer was changed to PBS/0.05% Tween 20 and a dilution series of the peptides was prepared in this buffer with a final DMSO concentration of 0.5%. The top peptide concentration was 500 nM or 10 µM with 6 further 3-fold (500 nm), or 2-fold (10 µM) dilutions in PBS/0.05% Tween 20. The SPR analysis was run at 25° C. at a flow rate of 90 µl/min with 60 seconds association and 100-600 seconds dissociation. After each cycle, a regeneration step (10 µl of 10 mM glycine pH 2) was employed. Data were corrected for DMSO excluded volume effects. All data were double-referenced for blank injections and reference surface using standard processing procedures and data processing and kinetic fitting were performed using Scrubber software, version 2.0c (BioLogic Software). Data were fitted using mass transport model allowing for mass transport effects where appropriate.

Selected peptides of the invention were tested in the above mentioned assay and the results are shown in Table 5:

TABLE 5

SPR Data for Selected Peptides of the Invention

| Peptide Number | SEQ ID NO: | Peptide Reference | Sequence | KD nM |
|---|---|---|---|---|
| BCY592 | 189 | 74-01-04 | ACIEEGQYCFADPYMCA | 41.8 |
| BCY593 | 193 | Ac-(74-01-04) | [Ac]CIEEGQYCFADPYMC | 37 |
| BCY3814 | 31 | 74-01-04 Nle12 | ACIEEGQYCFADPY(Nle)CA | 33.3 |
| BCY7527 | 194 | Ac-(74-01-04)-Dap Nle12 | [Ac]CIEEGQYCFADPY[Nle]C[Dap] | 16.4 |
| BCY7768 | 195 | PEG3-(74-01-04) Pro2 D-Phe4 Nle12 | [PEG3]ACIPE[dF]QYCFADPY[Nle]CA | 33.9 |
| BCY7770 | 196 | PEG3-(74-01-04) Pro2 D-Phe4 Pro5 Nle12 | [PEG3]ACIPE[dF]PYCFADPY[Nle]CA | 18.6 |
| BCY7772 | 197 | PEG3-(74-01-04) D-Phe4 Pro5 Nle12 | [PEG3]ACIEE[dF]PYCFADPY[Nle]CA | 39.7 |
| BCY7773 | 198 | PEG3-(74-01-04) Pro2 Pro5 Nle12 | [PEG3]ACIPEGPYCFADPY[Nle]CA | 31.5 |
| BCY7774 | 199 | PEG3-(74-01-04) tBuAla1 Pro2 D-Phe4 Pro5 4MePhe6 4FPhe7 Nle12 | [PEG3]AC[tBuAla]PE[dF]P[4MePhe]C[4FPhe]ADPY[Nle]CA | 8.69 |
| BCY7775 | 200 | PEG3-(74-01-04) tBuAla1 Pro2 D-Phe4 4MePhe6 4FPhe7 Nle12 | [PEG3]AC[tBuAla]PE[dF]Q[4MePhe]C[4FPhe]ADPY[Nle]CA | 18.2 |
| BCY7776 | 201 | PEG3-(74-01-04) tBuAla1 D-Phe4 Pro5 4MePhe6 4FPhe7 Nle12 | [PEG3]AC[tBuAla]EE[dF]P[4MePhe]C[4FPhe]ADPY[Nle]CA | 17.3 |
| BCY7777 | 202 | PEG3-(74-01-04) tBuAla1 D-Phe4 4MePhe6 4FPhe7 Nle12 | [PEG3]AC[tBuAla]EE[dF]Q[4MePhe]C[4FPhe]ADPY[Nle]CA | 66 |
| BCY7796 | 203 | PEG3-(74-01-04) HyP2 Nle12 | [PEG3]ACI[HyP]EGQYCFADPY[Nle]CA | 24.7 |
| BCY7798 | 204 | PEG3-(74-01-04) D-Trp4 Nle12 | [PEG3]ACIEE[dW]QYCFADPY[Nle]CA | 12.1 |
| BCY7799 | 205 | PEG3-(74-01-04) Aze5 Nle12 | [PEG3]ACIEEG[Aze]YCFADPY[Nle]CA | 69.9 |
| BCY7800 | 206 | PEG3-(74-01-04) Pip5 Nle12 | [PEG3]ACIEEG[Pip]YCFADPY[Nle]CA | 1490 |
| BCY7801 | 207 | PEG3-(74-01-04) 2Nal6 Nle12 | [PEG3]ACIEEGQ[2Nal]CFADPY[Nle]CA | 18.7 |
| BCY7802 | 208 | PEG3-(74-01-04) 4MeOPhe6 Nle12 | [PEG3]ACIEEGQ[4MeoPhe]CFADPY[Nle]CA | 17.8 |
| BCY7803 | 209 | PEG3-(74-01-04) Tyr6 Nle12 | [PEG3]ACIEEGQYCYADPY[Nle]CA | 54.9 |
| BCY7804 | 210 | PEG3-(74-01-04) Aze10 Nle12 | [PEG3]ACIEEGQYCFAD[Aze]Y[Nle]CA | 85.7 |
| BCY7806 | 211 | PEG3-(74-01-04) Hse(Me)12 | [PEG3]ACIEEGQYCFADPY[Hse(Me)]CA | 204 |
| BCY7923 | 212 | Ac-(74-01-04) NMeIle1 Nle12 | [Ac]AC[NMeIle]EEGQYCFADPY[Nle]CA | 1149 |
| BCY7924 | 213 | Ac-(74-01-04) Aze2 Nle12 | [Ac]ACI[Aze]EGQYCFADPY[Nle]CA | 59 |
| BCY7925 | 214 | Ac-(74-01-04) Pip2 Nle12 | [Ac]ACI[Pip]EGQYCFADPY[Nle]CA | 105 |
| BCY7926 | 215 | Ac-(74-01-04) NMeGlu2 Nle12 | [Ac]ACI[NMeGlu]EGQYCFADPY[Nle]CA | 220 |
| BCY7927 | 216 | Ac-(74-01-04) NMeGlu3 Nle12 | [Ac]ACIE[NMeGlu]GQYCFADPY[Nle]CA | 1650 |
| BCY7928 | 217 | Ac-(74-01-04) D-Asp4 Nle12 | [Ac]ACIEE[dD]QYCFADPY[Nle]CA | 97 |
| BCY7929 | 218 | Ac-(74-01-04) NMeAla5 Nle12 | [Ac]ACIEEG[NMeAla]YCFADPY[Nle]CA | 269 |
| BCY7930 | 219 | Ac-(74-01-04) NMeTyr6 Nle12 | [Ac]ACIEEGQ[NMeTyr]CFADPY[Nle]CA | 993 |

TABLE 5-continued

SPR Data for Selected Peptides of the Invention

| Peptide Number | SEQ ID NO: | Peptide Reference | Sequence | KD nM |
|---|---|---|---|---|
| BCY7931 | 220 | Ac-(74-01-04) HPhe6 Nle12 | [Ac]ACIEEGQ[HPhe]CFADPY[Nle]CA | 1746 |
| BCY7933 | 221 | Ac-(74-01-04) 2Pal6 Nle12 | [Ac]ACIEEGQ[2Pal]CFADPY[Nle]CA | 790 |
| BCY7934 | 222 | Ac-(74-01-04) 3Pal6 Nle12 | [Ac]ACIEEGQ[3Pal]CFADPY[Nle]CA | 196 |
| BCY7936 | 223 | Ac-(74-01-04) 4,4-BPA6 Nle12 | [Ac]ACIEEGQ[44BPA]CFADPY[Nle]CA | 43 |
| BCY7937 | 224 | Ac-(74-01-04) HPhe7 Nle12 | [Ac]ACIEEGQYC[HPhe]ADPY[Nle]CA | 556 |
| BCY7939 | 225 | Ac-(74-01-04) 2Pal7 Nle12 | [Ac]ACIEEGQYC[2Pal]ADPY[Nle]CA | 98.6 |
| BCY7940 | 226 | Ac-(74-01-04) 3Pal7 Nle12 | [Ac]ACIEEGQYC[3Pal]ADPY[Nle]CA | 58.6 |
| BCY7941 | 227 | Ac-(74-01-04) 4Pal7 Nle12 | [Ac]ACIEEGQYC[4Pal]ADPY[Nle]CA | 44.4 |
| BCY7942 | 228 | Ac-(74-01-04) 4,4-BPA7 Nle12 | [Ac]ACIEEGQYC[44BPA]ADPY[Nle]CA | 35.9 |
| BCY7943 | 229 | Ac-(74-01-04) 1Nal7 Nle12 | [Ac]ACIEEGQYC[1Nal]ADPY[Nle]CA | 151 |
| BCY7944 | 230 | Ac-(74-01-04) 4tBuPhe7 Nle12 | [Ac]ACIEEGQYC[4tBuPhe]ADPY[Nle]CA | 42.2 |
| BCY7945 | 231 | Ac-(74-01-04) NMeAla8 Nle12 | [Ac]ACIEEGQYCF[NMeAla]DPY[Nle]CA | 665 |
| BCY7950 | 232 | Ac-(74-01-04) 5,5-dmP5 Nle12 | [Ac]ACIEEG[55DMP]YCFADPY[Nle]CA | 31.1 |
| BCY7953 | 233 | Ac-(74-01-04) HyP10 Nle12 | [Ac]ACIEEGQYCFAD[HyP]Y[Nle]CA | 86.6 |
| BCY7954 | 234 | Ac-(74-01-04) Oic5 Nle12 | [Ac]ACIEEG[Oic]YCFADPY[Nle]CA | 11.1 |
| BCY7955 | 235 | Ac-(74-01-04) Oic10 Nle12 | [Ac]ACIEEGQYCFAD[Oic]Y[Nle]CA | 169 |
| BCY7956 | 236 | Ac-(74-01-04) Oic2 Nle12 | [Ac]ACI[Oic]EGQYCFADPY[Nle]CA | 228 |
| BCY7957 | 237 | Ac-(74-01-04) Oxa10 Nle12 | [Ac]ACIEEGQYCFAD[Oxa]Y[Nle]CA | 118 |
| BCY7958 | 238 | Ac-(74-01-04) Oxa2 Nle12 | [Ac]ACI[Oxa]EGQYCFADPY[Nle]CA | 20 |
| BCY7959 | 239 | Ac-(74-01-04) Oxa5 Nle12 | [Ac]ACIEEG[Oxa]YCFADPY[Nle]CA | 37.7 |
| BCY7960 | 240 | Ac-(74-01-04) Pro2 Pro5 Nle12 | [Ac]ACIPEGPYCFADPY[Nle]CA | 10.7 |
| BCY7952 | 241 | Ac-(74-01-04) HyP5 Nle12 | [Ac]ACIEEG[HyP]YCFADPY[Nle]CA | 11.8 |
| BCY7961 | 242 | Ac-(74-01-04) Pro2 DAla4 Pro5 Nle12 | [Ac]ACIPE[dA]PYCFADPY[Nle]CA | 10 |
| BCY7965 | 243 | Ac-(74-01-04) tBuAla1 Pro2 DAla4 Pro5 Nle12 | [Ac]AC[tBuAla]PE[dA]PYCFADPY[Nle]CA | 4.75 |
| BCY8217 | 244 | A-(74-01-04)-A D-Ala8 Nle12 | ACIEEGQYCF[dA]DPY[Nle]CA | 500 |
| BCY8656 | 245 | Ac-(74-01-04) tBuAla1 Nle12 | [Ac]AC[tBuAla]EEGQYCFADPY[Nle]CA | 31 (n = 2) |
| BCY8657 | 246 | Ac-(74-01-04) Chg1 Nle12 | [Ac]AC[Chg]EEGQYCFADPY[Nle]CA | 62.4 |
| BCY8658 | 247 | Ac-(74-01-04) Ac5c1 Nle12 | [Ac]AC[AC5C]EEGQYCFADPY[Nle]CA | 200 |
| BCY8659 | 248 | Ac-(74-01-04) Pro2 Nle12 | [Ac]ACIPEGQYCFADPY[Nle]CA | 33.4 |
| BCY8660 | 249 | Ac-(74-01-04) Gln2 Nle12 | [Ac]ACIQEGQYCFADPY[Nle]CA | 380 |
| BCY8661 | 250 | Ac-(74-01-04) Pro3 Nle12 | [Ac]ACIEPGQYCFADPY[Nle]CA | 154.5 (n = 2) |
| BCY8662 | 251 | Ac-(74-01-04) Gln3 Nle12 | [Ac]ACIEQGQYCFADPY[Nle]CA | 179 |
| BCY8663 | 252 | Ac-(74-01-04) D-Phe4 Nle12 | [Ac]ACIEE[dF]QYCFADPY[Nle]CA | 25.1 (n = 2) |
| BCY8664 | 253 | Ac-(74-01-04) D-Ala4 Nle12 | [Ac]ACIEE[dA]QYCFADPY[Nle]CA | 59.5 (n = 2) |
| BCY8665 | 254 | Ac-(74-01-04) Ac5c4 Nle12 | [Ac]ACIEE[AC5C]QYCFADPY[Nle]CA | 200 |

TABLE 5-continued

SPR Data for Selected Peptides of the Invention

| Peptide Number | SEQ ID NO: | Peptide Reference | Sequence | KD nM |
|---|---|---|---|---|
| | | | | (n = 2) |
| BCY8667 | 255 | Ac-(74-01-04) Ala5 Nle12 | [Ac]ACIEEGAYCFADPY[Nle]CA | 68.5 (n = 3) |
| BCY8668 | 256 | Ac-(74-01-04) Aib5 Nle12 | [Ac]ACIEEG[Aib]YCFADPY[Nle]CA | 28.7 |
| BCY8669 | 257 | Ac-(74-01-04) Ac5c5 Nle12 | [Ac]ACIEEG[AC5C]YCFADPY[Nle]CA | 33.2 (n = 2) |
| BCY8670 | 258 | Ac-(74-01-04) 4MePhe6 Nle12 | [Ac]ACIEEGQ[4MePhe]CFADPY[Nle]CA | 1000 |
| BCY8671 | 259 | Ac-(74-01-04) 1Nal6 Nle12 | [Ac]ACIEEGQ[1Nal]CFADPY[Nle]CA | 297 |
| BCY8673 | 260 | Ac-(74-01-04) 2Nal7 Nle12 | [Ac]ACIEEGQYC[2Nal]ADPY[Nle]CA | 117 |
| BCY8674 | 261 | Ac-(74-01-04) 4NO2Phe7 Nle12 | [Ac]ACIEEGQYC[NO2Phe]ADPY[Nle]CA | 44.5 (n = 2) |
| BCY8675 | 262 | Ac-(74-01-04) 4BrPhe7 Nle12 | [Ac]ACIEEGQYC[4BrPhe]ADPY[Nle]CA | 57.5 (n = 2) |
| BCY8676 | 263 | Ac-(74-01-04) Abu8 Nle12 | [Ac]ACIEEGQYCF[Abu]DPY[Nle]CA | 1000 |
| BCY8677 | 264 | Ac-(74-01-04) Ahp12 | [Ac]ACIEEGQYCFADPY[Ahp]CA | 64.6 (n = 2) |
| BCY9273 | 265 | Ac-A-(74-01-04)-A | [Ac]ACIEEGQYCFADPYMCA | 108 |

3. CD137 Cell Activity

The biological activity of the CD137-specific peptides was tested using the cellular CD137 luciferase reporter assay kit (Promega). The cells in this commercially available kit express luciferase that is activated down-stream of CD137. This assay can be used to assess agonism (exemplified by CD137 ligand, CD137L) and antagonism (exemplified by bicyclic peptide 74-01-04-N002).

The Promega CD137 cell-activity assay uses NF-κB luciferase luminescence as a read-out of CD137 activation in Jurkat cells. Briefly, the experiments were performed by preparing medium by thawing FBS and adding 1% FBS to RPM1-1640 (Promega kit CS196005). Dilute agonists at concentration giving agonism CD137L (R&D systems 2295-4L/CF) diluted to 100 nM in the RPM1-1640 medium as final concentration in the assay. Dilute and then titrate down the bicyclic peptide in a sterile 96 well-plate. Suggested starting concentration for the bicyclic peptide is 10 μM, 100-fold excess over the agonist CD137L. Prepare enough reagent for duplicate samples and then perform ⅓ dilution series dilution series. Include positive control CD137L and bicyclic peptide alone. Thaw CD137 Jurkat cells in the water-bath and then add 500 μl cells to 9.5 ml pre-warmed 1% FBS RPM1-1640 medium. Add 50 μl cells/well to white cell culture plate. Add 12.5 μl bicyclic peptide (at 6× final concentration) to the cells. Then add 12.5 μl of agonist (at 6× final concentration) as duplicate samples or 1% FBS RPMl-1640 alone as background control.

Co-incubate cells together with CD137L agonist and bicyclic peptide for 6 h at 37° C., 5% $CO_2$. After 6 h thaw Bio-Glo™ and develop the assay at room-temperature. Add 75 μl Bio-Glo™ per well and incubate 5-10 min. Read luminescence signal on Pherastar plate-reader LUM plus models, gain 3600 using MARS software. Analyse data by calculating the percentage inhibition compared to CD137L alone. Transform the data to x=log (X), then plot log (inhibitor) vs. response variable slope (4 parameters) to calculate the $IC_{50}$ value.

The Promega CD137 cell-reporter assay (product number CS196008) was used to determine the antagonistic effect of the peptide BCY592 (74-01-04-N002; SEQ ID NO: 189) in inhibiting the natural ligand CD137L induction. The CD137 assay cells were co-incubated with trimeric CD137L (R&D systems)+BCY592 peptide. The CD137 reporter activity was determined as NF-κB promotor driven luciferase activity. The effect of the peptide BCY592 was plotted as % inhibition relative to baseline CD137L activity in the assay and used to determine the IC50-value.

The results are shown in FIG. 1 where it can be seen that the bicyclic peptide BCY592 specific for CD137 can act as an antagonist that inhibits CD137L activity. This result indicates that this peptide can be used in settings where it is desirable to block CD137 biological activity. It is known that CD137 activity can cause liver injury due to inflammation driven by the local immune cells. It is therefore believed that the bicyclic peptide BCY592 (and by inference other bicyclic CD137 peptides of the invention) may reduce CD137—CD137L driven inflammation which would reduce hepatotoxicity of CD137 agonists.

4. Fluorescence Polarization Competition Binding Assay

The binding site of the hCD137-specific Bicycle peptide was determined by competition experiment between a fluorescent labelled CD137 binding peptide and natural ligand CD137L, agonistic antibodies Urelumab and Utomilumab. Urelumab antibody binds to a distinct binding site while CD137L and Utomilumab both bind to the site termed the ligand-binding site.

The competitor agonists CD137L (R&D systems), Urelumab and Utomilumab were diluted in assay buffer 20 mM HEPES, 150 mM NnCl, 0.05% P20, pH7.5 to a top concentration of 500-1000 nM. The human CD137 protein (AcroBiosystems) was diluted to 500 nM final concentration in the assay. Finally, the fluorescent tracer peptide BCY640 (74-01-04-N001) was added at 1 nM. The assay was typically set up by adding 5 μL agonist competitor, 10 μL CD137 protein then 10 μL fluorescent peptide. The total volume of 25 μL was prepared in black walled and bottomed low binding low volume 384 well plates. Measurements were conducted on a BMG PHERAstar FS equipped with an FP 485 520 520 optic module at 25° C. with 200 flashes per well and a positioning delay of 0.1 second. Each well was measured every 5 minutes for 60 minutes. The gain was set in a well containing tracer without target protein. The mP-values at the end of the 60 minutes read were plotted against concentration of the agonists. Reduction in the mP-values indicates competition between the known agonist and the tracer peptide.

Figure 2:
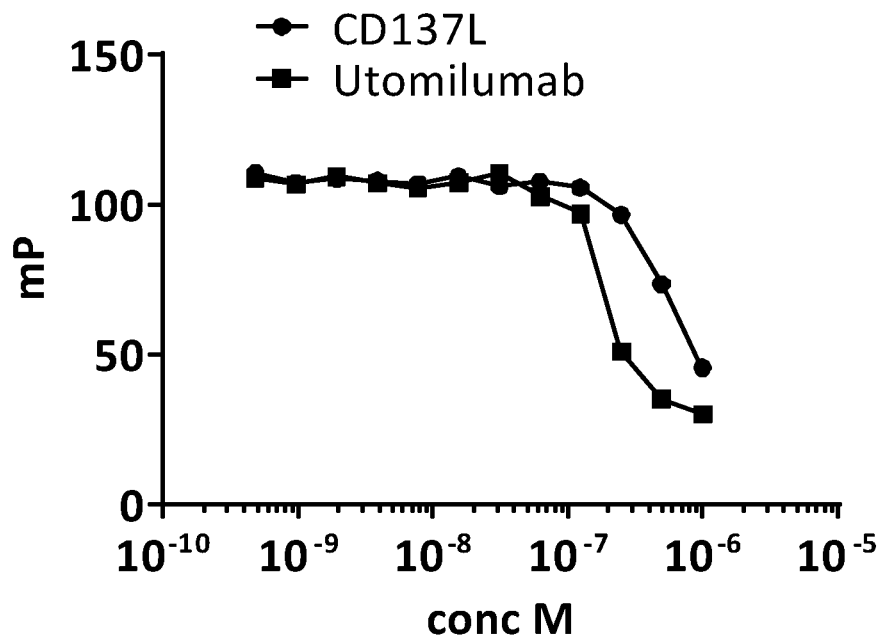
FIG. 2: Competition of CD137L or monoclonal antibody Utomilumab with a fluorescently labelled peptide BCY640 for binding to CD137 as measured by fluorescence polarization.
Figure 3:
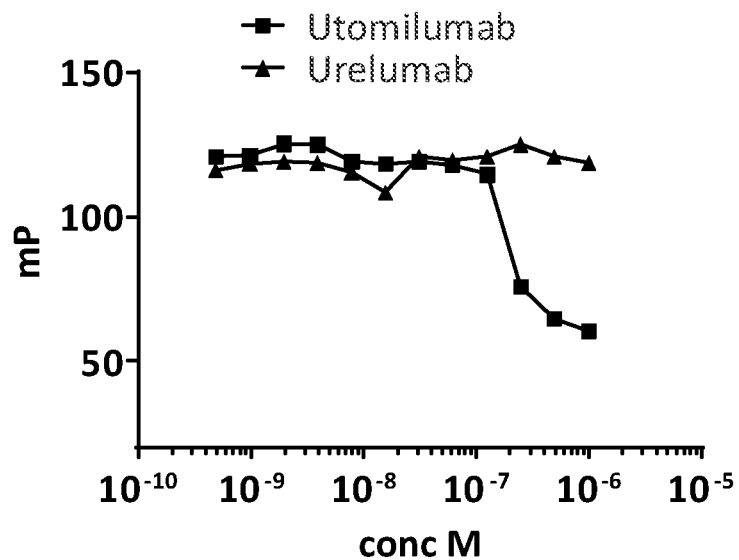
FIG. 3: Competition of monoclonal antibodies Utomilumab or Urelumab with a fluorescently labelled peptide BCY640 for binding to CD137 as measured by fluorescence polarization.

The results are shown in FIGS. 2 and 3 where it can be seen that the CD137 binding Bicycle (BCY640) binds to the physiologically relevant epitope that is shared with both the natural CD137 ligand (CD137L) and CD137 antibody (Utomilumab).

The invention claimed is:

1. A peptide ligand specific for CD137 comprising a polypeptide comprising at least three cysteine residues, separated by two loop sequences, and a molecular scaffold which forms covalent bonds with the cysteine residues of the polypeptide such that two polypeptide loops are formed on the molecular scaffold, which comprises an amino acid sequence selected from:

$$C_i\text{-I/L/M/V-E/D/P/S-P/E/A-G-P/Q-Y/F-}C_{ii}\text{-Y-A-D-P-Y/M-M/L/Y-}C_{iii}; \quad \text{(SEQ ID NO: 41)}$$

$$C_i\text{-I-E-E-G-Q-Y-}C_{ii}\text{-}X_1\text{-}X_2\text{-D-}X_3\text{-Y/Q/M-}X_4\text{-}C_{iii}; \quad \text{(SEQ ID NO: 20)}$$

$$C_i\text{-D-I-G-P-P-Y-}C_{ii}\text{-Y-R/A-D-M/P-Y-M-}C_{iii}; \quad \text{(SEQ ID NO: 21)}$$

$$C_i\text{-D-E-W-G-L-F/Y-}C_{ii}\text{-I/F-P/A-H-S/P-D-}C_{iii}; \text{ and} \quad \text{(SEQ ID NO: 22)}$$

$$C_i\text{IEPGPFC}_{ii}\text{YADPYMC}_{iii}; \quad \text{(SEQ ID NO: 19)}$$

wherein $X_1$-$X_4$ represent any amino acid residue and $C_i$, $C_{ii}$ and $C_{iii}$ represent first, second and third cysteine residues, respectively or a pharmaceutically acceptable salt thereof.

2. The peptide ligand as defined in claim 1, wherein the peptide ligand of $C_i$-I-E-E-G-Q-Y-$C_{ii}$-$X_1$-$X_2$-D-$X_3$-Y/Q-X$C_{iii}$ (SEQ ID NO: 20) comprises an amino acid sequence selected from any one of SEQ ID NOS: 1-14:

$$C_i\text{IEEGQYC}_{ii}\text{YRDMYMC}_{iii}; \quad \text{(SEQ ID NO: 1)}$$

$$C_i\text{IEEGQYC}_{ii}\text{YADPYMC}_{iii}; \quad \text{(SEQ ID NO: 2)}$$

$$C_i\text{IEEGQYC}_{ii}\text{YADPYYC}_{iii}; \quad \text{(SEQ ID NO: 3)}$$

$$C_i\text{IEEGQYC}_{ii}\text{YSDPYYC}_{iii}; \quad \text{(SEQ ID NO: 4)}$$

$$C_i\text{IEEGQYC}_{ii}\text{FADPYMC}_{iii}; \quad \text{(SEQ ID NO: 5)}$$

$$C_i\text{IEEGQYC}_{ii}\text{YADHQLC}_{iii}; \quad \text{(SEQ ID NO: 6)}$$

$$C_i\text{IEEGQYC}_{ii}\text{HADPYYC}_{iii}; \quad \text{(SEQ ID NO: 7)}$$

$$C_i\text{IEEGQYC}_{ii}\text{HADPYFC}_{iii}; \quad \text{(SEQ ID NO: 8)}$$

$$C_i\text{IEEGQYC}_{ii}\text{YADHYMC}_{iii}; \quad \text{(SEQ ID NO: 9)}$$

$$C_i\text{IEEGQYC}_{ii}\text{YADPYLC}_{iii}; \quad \text{(SEQ ID NO: 10)}$$

$$C_i\text{IEEGQYC}_{ii}\text{YSDPYLC}_{iii}; \quad \text{(SEQ ID NO: 11)}$$

$$C_i\text{IEEGQYC}_{ii}\text{FADPYLC}_{iii}; \quad \text{(SEQ ID NO: 12)}$$

$$C_i\text{IEEGQYC}_{ii}\text{HADPYMC}_{iii}; \text{ and} \quad \text{(SEQ ID NO: 13)}$$

$$C_i\text{IEEGQYC}_{ii}\text{HADPQMC}_{iii}; \quad \text{(SEQ ID NO: 14)}$$

or an amino acid sequence selected from:
A-(SEQ ID NO: 1)-A (herein referred to as 74-01-00-N004);
A-(SEQ ID NO: 2)-A (herein referred to as 74-01-01-N001);
A-(SEQ ID NO: 3)-A (herein referred to as 74-01-02-N001);
A-(SEQ ID NO: 4)-A (herein referred to as 74-01-03-N001);
A-(SEQ ID NO: 5)-A (herein referred to as 74-01-04-N001);
A-(SEQ ID NO: 6)-A (herein referred to as 74-01-05-N001);
A-(SEQ ID NO: 7)-A (herein referred to as 74-01-06-N001);
A-(SEQ ID NO: 8)-A (herein referred to as 74-01-07-N001);
A-(SEQ ID NO: 9)-A (herein referred to as 74-01-08-N001);
A-(SEQ ID NO: 10)-A (herein referred to as 74-01-09-N001);
A-(SEQ ID NO: 10)-SVG (herein referred to as 74-01-09-T03-N002);
A-(SEQ ID NO: 11)-A (herein referred to as 74-01-10-N001);
A-(SEQ ID NO: 12)-A (herein referred to as 74-01-11-N001);
A-(SEQ ID NO: 13)-A (herein referred to as 74-01-13-N001); and
A-(SEQ ID NO: 14)-A (herein referred to as 74-01-14-N001).

3. The peptide ligand as defined in claim 1, wherein the peptide ligand $C_i$-D-I-G-P-P-Y-$C_{ii}$-Y-R/A-D-M/P-Y-M-$C_{iii}$ (SEQ ID NO: 21) comprises an amino acid sequence selected from:

$$C_i\text{DIGPPYC}_{ii}\text{YRDMYMC}_{iii}; \text{ and} \quad \text{(SEQ ID NO: 15)}$$

$$C_i\text{DIGPPYC}_{ii}\text{YADPYMC}_{iii}; \quad \text{(SEQ ID NO: 16)}$$

or an amino acid sequence selected from:
A-(SEQ ID NO: 15)-A (herein referred to as 74-01-16-N001); and A-(SEQ ID NO: 16)-A (herein referred to as 74-01-17-N001).

4. The peptide ligand as defined in claim 1, wherein the peptide ligand of $C_i$-D-E-W-G-L-F/Y-$C_{ii}$-I/F-P/A-H-S/P-D-$C_{iii}$ (SEQ ID NO: 22) comprises an amino acid sequence selected from:

$C_i$DEWGLFC$_{ii}$IPHSDC$_{iii}$; (SEQ ID NO: 17)
and $C_i$DEWGLYC$_{ii}$FAHPDC$_{iii}$; (SEQ ID NO: 18)

or an amino acid sequence selected from:
Ac-A-(SEQ ID NO: 17)-A (herein referred to as 74-02-00-N004); and
A-(SEQ ID NO: 18)-A (herein referred to as 74-02-01-N001).

5. The peptide ligand as defined in claim 1, wherein the peptide ligand of $C_i$IEPGPFC$_{ii}$YADPYMC$_{iii}$ (SEQ ID NO: 19) comprises an amino acid sequence of: A-(SEQ ID NO: 19)-NRV (herein referred to as 74-19-00-T01-N002).

6. A peptide ligand specific for CD137 comprising a polypeptide comprising at least three cysteine residues, separated by two loop sequences, and a molecular scaffold which forms covalent bonds with the cysteine residues of the polypeptide such that two polypeptide loops are formed on the molecular scaffold, which comprises an amino acid sequence selected from:

$C_i$IEEGQYC$_{ii}$FADPY(Nle)C$_{iii}$; (SEQ ID NO: 23)

$C_i$IKEGQYC$_{ii}$FADPY(Nle)C$_{iii}$; (SEQ ID NO: 24)

$C_i$IEKGQYC$_{ii}$FADPY(Nle)C$_{iii}$; (SEQ ID NO: 25)

$C_i$IEE(D-K)QYC$_{ii}$FADPY(Nle)C$_{iii}$; (SEQ ID NO: 26)

$C_i$IEEGKYC$_{ii}$FADPY(Nle)C$_{iii}$; (SEQ ID NO: 27)

$C_i$IEEGQYC$_{ii}$KADPY(Nle)C$_{iii}$; (SEQ ID NO: 28)

$C_i$IEEGQYC$_{ii}$FADKY(Nle)C$_{iii}$; (SEQ ID NO: 29)

$C_i$IEEGQYC$_{ii}$FADPYKC$_{iii}$; (SEQ ID NO: 30)

(SEQ ID NO: 40; 74-22-00)
$C_i$LPPGQYC$_{ii}$FPDLLLC$_{iii}$ (SEQ ID NO: 31; BCY3814)
A-$C_i$IEEGQYC$_{ii}$FADPY(Nle)C$_{iii}$-A;

(SEQ ID NO: 32; BCY7732)
Ac-A-$C_i$IEEGQYC$_{ii}$FADPY(Nle)C$_{iii}$-Dap;

(SEQ ID NO: 33; BCY7733)
Ac-A-$C_i$IKEGQYC$_{ii}$FADPY(Nle)C$_{iii}$-A;

(SEQ ID NO: 34; BCY7734)
Ac-A-$C_i$IEKGQYC$_{ii}$FADPY(Nle)C$_{iii}$-A;

(SEQ ID NO: 35; BCY7735)
Ac-A-$C_i$IEE(D-K)QYC$_{ii}$FADPY(Nle)C$_{iii}$-A;

(SEQ ID NO: 36; BCY7736)
Ac-A-$C_i$IEEGKYC$_{ii}$FADPY(Nle)C$_{iii}$-A;

(SEQ ID NO: 37; BCY7737)
Ac-A-$C_i$IEEGQYC$_{ii}$KADPY(Nle)C$_{iii}$-A;

(SEQ ID NO: 38; BCY7738)
Ac-A-$C_i$IEEGQYC$_{ii}$FADKY(Nle)C$_{iii}$-A;
and (SEQ ID NO: 39; BCY7739)
Ac-A-$C_i$IEEGQYC$_{ii}$FADPYKC$_{iii}$-A;

or an amino acid sequence selected from:

| Peptide Number | SEQ ID NO: | Sequence |
|---|---|---|
| BCY633 | 42 | [B-Ala]-Sar5-ACIEEGQYCYRDMYMCA |
| BCY634 | 43 | [Ac]ACIEEGQYCYRDMYIVICA-Sar6-K(Fl) |
| BCY636 | 44 | ACIEEGQYCYADPYIVICA-Sar6-K(Fl) |
| BCY635 | 45 | [B-Ala]-Sar5-ACIEEGQYCYADPYWICA |
| BCY638 | 46 | ACIEEGQYCYADPYYCASar6-K |
| BCY637 | 47 | [B-Ala]-Sar5-ACIEEGQYCYADPYYCA |
| BCY639 | 48 | ACIEEGQYCYSDPYYCA-Sar6-K |
| BCY640 | 49 | ACIEEGQYCFADPYMCA-Sar6-K |
| BCY641 | 50 | G-Sar5-ACIEEGQYCFADPYMCA |
| BCY7239 | 52 | Ac-CIK(Peg12)EGQYCFADPYMC |
| BCY7240 | 53 | Ac-CIEK(Peg12)GQYCFADPYMC |
| BCY7242 | 55 | Ac-CIEEGK(Peg12)YCFADPYMC |
| BCY7244 | 57 | Ac-CIEEGQYCK(Peg12)ADPYMC |

-continued

| Peptide Number | SEQ ID NO: | Sequence |
|---|---|---|
| BCY7245 | 58 | Ac-CIEEGQYCFK(Peg12)DPYMC |
| BCY7247 | 60 | Ac-CIEEGQYCFADK(Peg12)YMC |
| BCY7248 | 61 | Ac-CIEEGQYCFADPK(Peg12)MC |
| BCY7249 | 62 | Ac-CIEEGQYCFADPYK(Peg12)C |
| BCY7416 | 63 | [Ac]IEE[dK(PEG12Fl)]QYCFADPY[Nle]C |
| BCY7519 | 64 | ACIEEGQYCFADPY[Nle]CA |
| BCY7520 | 65 | [Peg12]-ACIEEGQYCFADPY[Nle]CA |
| BCY642 | 66 | ACIEEGQYCYADHQLCA-Sar6-K |
| BCY643 | 67 | ACIEEGQYCHADPYYCA-Sar6-K |
| BCY644 | 68 | ACIEEGQYCHADPYFCA-Sar6-K |
| BCY645 | 69 | ACIEEGQYCYADHYMCA-Sar6-K |
| BCY646 | 70 | ACIEEGQYCYADPYLCA-Sar6-K |
| BCY647 | 71 | ACIEEGQYCYADPYLCSVG-Sar6-K |
| BCY648 | 72 | (Fl)G-Sar5-ACIEEGQYCYADPYLCSVG |
| BCY649 | 73 | ACIEEGQYCYSDPYLCA-Sar6-K |
| BCY650 | 74 | ACIEEGQYCFADPYLCA-Sar6-K |
| BCY652 | 75 | ACIEEGQYCHADPYIVICA-Sar6-K |
| BCY653 | 76 | ACIEEGQYCHADPQMCA-Sar6-K |
| BCY655 | 77 | ACDIGPPYCYRDMYIVICA-Sar6-K |
| BCY656 | 78 | ADIGPPYCYADPYIVICA-Sar6-K |
| BCY7251 | 79 | ACLDPGPFCFADPYIVICA-Sar6-K |
| BCY7253 | 80 | ACLDEGPYCFADPYFCA-Sar6-K |
| BCY7255 | 81 | ACINEGPYCFADPYIVICA-Sar6-K |
| BCY7257 | 82 | ACIEQGPFCFADPYIVICA-Sar6-K |
| BCY7259 | 83 | ACVEEGPFCFADPYYCA-Sar6-K |
| BCY7261 | 84 | ACLDEGPFCFSDPYIVICA-Sar6-K |
| BCY657 | 85 | [B-Ala]-Sar5-ACDEWGLFCIPHSDCA |
| BCY659 | 86 | ACDEWGLYCFAHPDCA-Sar6-K |
| BCY7119 | 87 | ACLDPGPYCYADPYIVICTFH-Sar6-K |
| BCY660 | 88 | ACIEPGPFCYADPYMCNRV-Sar6-K |
| BCY661 | 89 | G-Sar5-ACIEPGPFCYADPYMCNRV |
| BCY7120 | 90 | ACLEPGPYCYADPYIVICTHL-Sar6-K |
| BCY7122 | 91 | ACLPPGPYCFPDPYFCA-Sar6-K |
| BCY7151 | 92 | [PEG3]-ACIEEGQYCFADPY[Nle]CA |
| BCY7152 | 115 | [PEG3]-ACLEEGQYCFADPY[Nle]CA |
| BCY7153 | 116 | [PEG3]-AC[Nle]EEGQYCFADPY[Nle]CA |
| BCY7154 | 117 | [PEG3]-AC-Chg-EEGQYCFADPY[Nle]CA |
| BCY7155 | 118 | [PEG3]-AC-Cha-EEGQYCFADPY[Nle]CA |

-continued

| Peptide Number | SEQ ID NO: | Sequence |
|---|---|---|
| BCY7156 | 119 | [PEG3]-ACIPEGQYCFADPY[Nle]CA |
| BCY7157 | 120 | [PEG3]-ACIDEGQYCFADPY[Nle]CA |
| BCY7158 | 121 | [PEG3]-ACI-Aad-EGQYCFADPY[Nle]CA |
| BCY7159 | 122 | [PEG3]-ACI-Api-EGQYCFADPY[Nle]CA |
| BCY7160 | 123 | [PEG3]-ACIEPGQYCFADPY[Nle]CA |
| BCY7161 | 124 | [PEG3]-ACIEDGQYCFADPY[Nle]CA |
| BCY7162 | 125 | [PEG3]-ACIE-Aad-GQYCFADPY[Nle]CA |
| BCY7163 | 126 | [PEG3]-ACIE-Api-GQYCFADPY[Nle]CA |
| BCY7164 | 127 | [PEG3]-ACIEE-Sar-QYCFADPY[Nle]CA |
| BCY7165 | 128 | [PEG3]-ACIEE-DLys-QYCFADPY[Nle]CA |
| BCY7166 | 129 | [PEG3]-ACIEE-DPhe-QYCFADPY[Nle]CA |
| BCY7167 | 130 | [PEG3]-ACIEE-DGlu-QYCFADPY[Nle]CA |
| BCY7168 | 131 | [PEG3]-ACIEE-DGln-QYCFADPY[Nle]CA |
| BCY7169 | 132 | [PEG3]-ACIEE-DLeu-QYCFADPY[Nle]CA |
| BCY7170 | 133 | [PEG3]-ACIEE-DSer-QYCFADPY[Nle]CA |
| BCY7172 | 134 | [PEG3]-ACIEE-MeDala-QYCFADPY[Nle]CA |
| BCY7173 | 135 | [PEG3]-ACIEE-Aib-QYCFADPY[Nle]CA |
| BCY7174 | 136 | [PEG3]-ACIEEGPYCFADPY[Nle]CA |
| BCY7175 | 137 | [PEG3]-ACIEEGQFCFADPY[Nle]CA |
| BCY7176 | 138 | [PEG3]-ACIEEGQ-2MeF-CFADPY[Nle]CA |
| BCY7177 | 139 | [PEG3]-ACIEEGQ-3MeF-CFADPY[Nle]CA |
| BCY7178 | 140 | [PEG3]-ACIEEGQ-4MeF-CFADPY[Nle]CA |
| BCY7179 | 141 | [PEG3]-ACIEEGQ-4FF-CFADPY[Nle]CA |
| BCY7180 | 142 | [PEG3]-ACIEEGQ-3FF-CFADPY[Nle]CA |
| BCY7181 | 143 | [PEG3]-ACIEEGQYC-2MeF-ADPY[Nle]CA |
| BCY7182 | 144 | [PEG3]-ACIEEGQYC-3MeF-ADPY[Nle]CA |
| BCY7183 | 145 | [PEG3]-ACIEEGQYC-4MeF-ADPY[Nle]CA |
| BCY7184 | 146 | [PEG3]-ACIEEGQYC-PheG-ADPY[Nle]CA |
| BCY7185 | 147 | [PEG3]-ACIEEGQYC-4FF-ADPY[Nle]CA |
| BCY7186 | 148 | [PEG3]-ACIEEGQYCFGDPY[Nle]CA |
| BCY7187 | 149 | [PEG3]-ACIEEGQYCFSDPY[Nle]CA |
| BCY7188 | 150 | [PEG3]-ACIEEGQYCFPDPY[Nle]CA |
| BCY7189 | 151 | [PEG3]-ACIEEGQYCFANPY[Nle]CA |
| BCY7190 | 152 | [PEG3]-ACIEEGQYCFAD-Pip-Y[Nle]CA |
| BCY7191 | 153 | [PEG3]-ACIEEGQYCFAD-MeAla-Y[Nle]CA |
| BCY7192 | 154 | [PEG3]-ACIEEGQYCFAD-Sar-Y[Nle]CA |
| BCY7193 | 155 | [PEG3]-ACIEEGQYCFAD-Aib-Y[Nle]CA |
| BCY7195 | 156 | [PEG3]AC[tBuAla]EEGQYCFADPY[Nle]CA |

-continued

| Peptide Number | SEQ ID NO: | Sequence |
|---|---|---|
| BCY7196 | 157 | [PEG3]AC[HLeu]EEGQYCFADPY[Nle]CA |
| BCY7197 | 158 | [PEG3]ACIEEGQ[2FPhe]CFADPY[Nle]CA |
| BCY7198 | 159 | [PEG3]ACIEEGQYC[2FPhe]ADPY[Nle]CA |
| BCY7199 | 160 | [PEG3]ACIEEGQYCF[CF3G]DPY[Nle]CA |
| BCY7200 | 161 | [PEG3]ACIEEGQYCFADP[pCoPhe][Nle]CA |
| BCY7201 | 162 | [PEG3]ACIEEGQYCFADP[pCaPhe][Nle]CA |
| BCY7202 | 163 | [PEG3]ACIEEGQYCFADPQ[Nle]CA |
| BCY7205 | 164 | [PEG3]ACIEEGQYCFADP[2MePhe][Nle]CA |
| BCY7206 | 165 | [PEG3]ACIEEGQYCFADP[3MePhe][Nle]CA |
| BCY7207 | 166 | [PEG3]ACIEEGQYCFADP[4MePhe][Nle]CA |
| BCY7208 | 167 | [PEG3]ACIEEGQYCFADP[Cit][Nle]CA |
| BCY7209 | 168 | [PEG3]ACIEEGQYCFADP[4FPhe][Nle]CA |
| BCY7210 | 169 | [PEG3]ACIEEGQYCFADPY[tBuAla]CA |
| BCY7211 | 170 | [PEG3]ACIEEGQYCFADPY[HLeu]CA |
| BCY7212 | 171 | [PEG3]ACIEEGQYCFADPYICA |
| BCY7213 | 172 | [PEG3]ACIEEGQYCFADPY[Cha]CA |
| BCY7214 | 173 | [PEG3]ACIEEGQYCFADPYFCA |
| BCY7215 | 174 | [PEG3]ACIEEGQYCFADPY[2MePhe]CA |
| BCY7216 | 175 | [PEG3]ACIEEGQYCFADPY[3MePhe]CA |
| BCY7217 | 176 | [PEG3]ACIEEGQYCFADPY[4MePhe]CA |
| BCY7218 | 177 | [PEG3]A[Pen]IEEGQYCFADPY[Nle]CA |
| BCY7219 | 178 | [PEG3]ACIEEGQY[Pen]FADPY[Nle]CA |
| BCY7220 | 179 | [PEG3]ACIEEGQYCFADPY[Nle][Pen]A |
| BCY7221 | 180 | [PEG3]A[HCys]IEEGQYCFADPY[Nle]CA |
| BCY7222 | 181 | [PEG3]ACIEEGQY[HCys]FADPY[Nle]CA |
| BCY7223 | 182 | [PEG3]ACIEEGQYCFADPY[Nle][HCys]A |
| BCY7224 | 183 | [PEG3]ACIEEGQYC[3FPhe]ADPY[Nle]CA |
| BCY7306 | 184 | [PEG3]-ACI[TetraZ]EGQYCFADPY[Nle]CA |
| BCY7308 | 185 | [PEG3]-ACIEEGQYCFA[TetraZ]PY[Nle]CA |
| BCY7309 | 186 | [PEG3]-ACIEEGQYCFADP[HGln][Nle]CA |
| BCY7310 | 187 | [PEG3]-AC[Ahp]EEGQYCFADPY[Nle]CA |
| BCY7311 | 188 | [PEG3]-ACIEEGQYCFADPY[Ahp]CA |
| BCY592 | 189 | ACIEEGQYCFADPYIVICA |
| BCY589 | 190 | HEHCIEEGQYCYADPYIVICA |
| BCY599 | 191 | ACIEEGQYCFADPYLCA |
| BCY631 | 192 | ACLPPGPYCFPDPYFCA |
| BCY592 | 189 | ACIEEGQYCFADPYIVICA |
| BCY593 | 193 | [Ac]CIEEGQYCFADPYMC |

-continued

| Peptide Number | SEQ ID NO: | Sequence |
|---|---|---|
| BCY3814 | 31 | ACIEEGQYCFADPY(Nle)CA |
| BCY7527 | 194 | [Ac]CIEEGQYCFADPY[Nle]C[Dap] |
| BCY7768 | 195 | [PEG3]ACIPE[dF]QYCFADPY[Nle]CA |
| BCY7770 | 196 | [PEG3]ACIPE[dF]PYCFADPY[Nle]CA |
| BCY7772 | 197 | [PEG3]ACIEE[dF]PYCFADPY[Nle]CA |
| BCY7773 | 198 | PEG3]ACIPEGPYCFADPY[Nle]CA |
| BCY7774 | 199 | [PEG3]AC[tBuAla]PE[dF]P[4MePhe]C[4FPhe]ADPY[Nle]CA |
| BCY7775 | 200 | [PEG3]AC[tBuAla]PE[dF]Q[4MePhe]C[4FPhe]ADPY[Nle]CA |
| BCY7776 | 201 | [PEG3]AC[tBuAla]EE[dF]P[4MePhe]C[4FPhe]ADPY[Nle]CA |
| BCY7777 | 202 | [PEG3]AC[tBuAla]EE[dF]Q[4MePhe]C[4FPhe]ADPY[Nle]CA |
| BCY7796 | 203 | [PEG3]ACI[HyP]EGQYCFADPY[Nle]CA |
| BCY7798 | 204 | [PEG3]ACIEE[dW]QYCFADPY[Nle]CA |
| BCY7799 | 205 | [PEG3]ACIEEG[Aze]YCFADPY[Nle]CA |
| BCY7800 | 206 | [PEG3]ACIEEG[Pip]YCFADPY[Nle]CA |
| BCY7801 | 207 | [PEG3]ACIEEGQ[2Nal]CFADPY[Nle]CA |
| BCY7802 | 208 | [PEG3]ACIEEGQ[4MeoPhe]CFADPY[Nle]CA |
| BCY7803 | 209 | [PEG3]ACIEEGQYCYADPY[Nle]CA |
| BCY7804 | 210 | [PEG3]ACIEEGQYCFAD[Aze]Y[Nle]CA |
| BCY7806 | 211 | [PEG3]ACIEEGQYCFADPY[Hse(Me)]CA |
| BCY7923 | 212 | [Ac]AC[NMeIle]EEGQYCFADPY[Nle]CA |
| BCY7924 | 213 | [Ac]ACI[Aze]EGQYCFADPY[Nle]CA |
| BCY7925 | 214 | [Ac]ACI[Pip]EGQYCFADPY[Nle]CA |
| BCY7926 | 215 | [Ac]ACI[NMeGlu]EGQYCFADPY[Nle]CA |
| BCY7927 | 216 | [Ac]ACIE[NMeGlu]GQYCFADPY[Nle]CA |
| BCY7928 | 217 | [Ac]ACIEE[dD]QYCFADPY[Nle]CA |
| BCY7929 | 218 | [Ac]ACIEEG[NMeAla]YCFADPY[Nle]CA |
| BCY7930 | 219 | [Ac]ACIEEGQ[NMeTyr]CFADPY[Nle]CA |
| BCY7931 | 220 | [Ac]ACIEEGQ[HPhe]CFADPY[Nle]CA |
| BCY7933 | 221 | [Ac]ACIEEGQ[2Pal]CFADPY[Nle]CA |
| BCY7934 | 222 | [Ac]ACIEEGQ[3Pal]CFADPY[Nle]CA |
| BCY7936 | 223 | [Ac]ACIEEGQ[44BPA]CFADPY[Nle]CA |
| BCY7937 | 224 | [Ac]ACIEEGQYC[HPhe]ADPY[Nle]CA |
| BCY7939 | 225 | [Ac]ACIEEGQYC[2Pal]ADPY[Nle]CA |
| BCY7940 | 226 | [Ac]ACIEEGQYC[3Pal]ADPY[Nle]CA |
| BCY7941 | 227 | [Ac]ACIEEGQYC[4Pal]ADPY[Nle]CA |
| BCY7942 | 228 | [Ac]ACIEEGQYC[44BPA]ADPY[Nle]CA |
| BCY7943 | 229 | [Ac]ACIEEGQYC[1Nal]ADPY[Nle]CA |
| BCY7944 | 230 | [Ac]ACIEEGQYC[4tBuPhe]ADPY[Nle]CA |

| Peptide Number | SEQ ID NO: | Sequence |
|---|---|---|
| BCY7945 | 231 | [Ac]ACIEEGQYCF[NMeAla]DPY[Nle]CA |
| BCY7950 | 232 | [Ac]ACIEEG[55DMp]YCFADPY[Nle]CA |
| BCY7953 | 233 | [Ac]ACIEEGQYCFAD[HyP]Y[Nle]CA |
| BCY7954 | 234 | [Ac]ACIEEG[Oic]YCFADPY[Nle]CA |
| BCY7955 | 235 | [Ac]ACIEEGQYCFAD[Oic]Y[Nle]CA |
| BCY7956 | 236 | [Ac]ACI[Oic]EGQYCFADPY[Nle]CA |
| BCY7957 | 237 | [Ac]ACIEEGQYCFAD[Oxa]Y[Nle]CA |
| BCY7958 | 238 | [Ac]ACI[Oxa]EGQYCFADPY[Nle]CA |
| BCY7959 | 239 | [Ac]ACIEEG[Oxa]YCFADPY[Nle]CA |
| BCY7960 | 240 | [Ac]ACIPEGPYCFADPY[Nle]CA |
| BCY7952 | 241 | [Ac]ACIEEG[HyP]YCFADPY[Nle]CA |
| BCY7961 | 242 | [Ac]ACIPE[dA]PYCFADPY[Nle]CA |
| BCY7965 | 243 | [Ac]AC[tBuAla]PE[dA]PYCFADPY[Nle]CA |
| BCY8217 | 244 | ACIEEGQYCF[dA]DPY[Nle]CA |
| BCY8656 | 245 | [Ac]AC[tBuAla]EEGQYCFADPY[Nle]CA |
| BCY8657 | 246 | [Ac]AC[Chg]EEGQYCFADPY[Nle]CA |
| BCY8658 | 247 | [Ac]AC[AC5C]EEGQYCFADPY[Nle]CA |
| BCY8659 | 248 | [Ac]ACIPEGQYCFADPY[Nle]CA |
| BCY8660 | 249 | [Ac]ACIQEGQYCFADPY[Nle]CA |
| BCY8661 | 250 | [Ac]ACIEPGQYCFADPY[Nle]CA |
| BCY8662 | 251 | [Ac]ACIEQGQYCFADPY[Nle]CA |
| BCY8663 | 252 | [Ac]ACIEE[df]QYCFADPY[Nle]CA |
| BCY8664 | 253 | [Ac]ACIEE[dA]QYCFADPY[Nle]CA |
| BCY8665 | 254 | [Ac]ACIEE[AC5C]QYCFADPY[Nle]CA |
| BCY8667 | 255 | [Ac]ACIEEGAYCFADPY[Nle]CA |
| BCY8668 | 256 | [Ac]ACIEEG[Aib]YCFADPY[Nle]CA |
| BCY8669 | 257 | [Ac]ACIEEG[AC5C]YCFADPY[Nle]CA |
| BCY8670 | 258 | [Ac]ACIEEGQ[4MePhe]CFADPY[Nle]CA |
| BCY8671 | 259 | [Ac]ACIEEGQ[1Nal]CFADPY[Nle]CA |
| BCY8673 | 260 | [Ac]ACIEEGQYC[2Nal]ADPY[Nle]CA |
| BCY8674 | 261 | [Ac]ACIEEGQYC[NO2Phe]ADPY[Nle]CA |
| BCY8675 | 262 | [Ac]ACIEEGQYC[4BrPhe]ADPY[Nle]CA |
| BCY8676 | 263 | [Ac]ACIEEGQYCF[Abu]DPY[Nle]CA |
| BCY8677 | 264 | [Ac]ACIEEGQYCFADPY[Ahp]CA |
| BCY9273 | 265 | [Ac]ACIEEGQYCFADPYMCA | wherein $C_i$, $C_{ii}$ and $C_{iii}$ represent first, second and third cysteine residues, respectively, Ac represents an N-terminal acetyl group and Dap represents diaminopropionic acid or a pharmaceutically acceptable salt thereof.

7. A peptide ligand specific for CD137 comprising a polypeptide comprising at least three cysteine residues, separated by two loop sequences, and a molecular scaffold which forms covalent bonds with the cysteine residues of the polypeptide such that two polypeptide loops are formed on the molecular scaffold, wherein the peptide ligand comprises an amino acid sequence which is:

(SEQ ID NO: 266)
$C_i$-$X_5$-$X_6$-$X_7$-$X_8$-$X_9$-$X_{10}$-$C_{ii}$-$X_{11}$-$X_{12}$-D-$X_{13}$-$X_{14}$-$X_{15}$-$C_{iii}$;

wherein $C_i$, $C_{ii}$ and $C_{iii}$ represent first, second and third cysteine residues, respectively;

$X_5$ represents Ile, tBuAla or Chg;
$X_6$ represents Glu, Pro, Asp, Lys, Aad, HyP or Oxa;
$X_7$ represents Glu, Lys or Aad;
$X_8$ represents Gly, D-Lys, D-Ala, L-Ala, D-Phe, D-Glu, D-Gln, D-Leu, D-Ser or D-Trp;
$X_9$ represents Gln, Lys, Ala, Pro, 5,5-dmP, Oic, Oxa, HyP, Aib or Ac5c;
$X_{10}$ represents Tyr, Phe, 3MePhe, 4MePhe, 4FPhe, 2Nal, 4MeOPhe or 4,4-BPA;
$X_{11}$ represents Phe, Lys, 4MePhe, 2FPhe, 4FPhe, 4Pal, 4,4-BPA, 4tBuPhe, NO2Phe or 4BrPhe;
$X_{12}$ represents Ala or Lys;
$X_{13}$ represents Pro or Lys;
$X_{14}$ represents Tyr or Lys; and
$X_{15}$ represents Met, Lys, Nle, HLeu or Ahp.

8. The peptide ligand as defined in claim 7, wherein the peptide ligand of SEQ ID NO: 266 is selected from the $C_i$ to $C_{iii}$ sequences of the following peptides or the full sequences of the following peptides:

| Peptide Number | SEQ ID NO: | Sequence |
| --- | --- | --- |
| BCY7239 | 52 | Ac-CIK(Peg12)EGQYCFADPYMC |
| BCY7240 | 53 | Ac-CIEK(Peg12)GQYCFADPYMC |
| BCY7242 | 55 | Ac-CIEEGK(Peg12)YCFADPYMC |
| BCY7244 | 57 | Ac-CIEEGQYCK(Peg12)ADPYMC |
| BCY7245 | 58 | Ac-CIEEGQYCFK(Peg12)DPYMC |
| BCY7247 | 60 | Ac-CIEEGQYCFADK(Peg12)YMC |
| BCY7248 | 61 | Ac-CIEEGQYCFADPK(Peg12)MC |
| BCY7249 | 62 | Ac-CIEEGQYCFADPYK(Peg12)C |
| BCY7416 | 63 | [Ac]CIEE[dK(PEG12Fl)]QYCFADPY[Nle]C |
| BCY7287 | 97 | [PEG3]-ACIEEGAYCFADPY(Nle)CA |
| BCY7297 | 106 | [PEG3]-ACIEEaQYCFADPY(Nle)CA |
| BCY7154 | 117 | [PEG3]-AC-Chg-EEGQYCFADPY[Nle]CA |
| BCY7156 | 119 | [PEG3]-ACIPEGQYCFADPY[Nle]CA |
| BCY7157 | 120 | [PEG3]-ACIDEGQYCFADPY[Nle]CA |
| BCY7158 | 121 | [PEG3]-ACI-Aad-EGQYCFADPY[Nle]CA |
| BCY7162 | 125 | [PEG3]-ACIE-Aad-GQYCFADPY[Nle]CA |
| BCY7165 | 128 | [PEG3]-ACIEE-DLys-QYCFADPY[Nle]CA |
| BCY7166 | 129 | [PEG3]-ACIEE-DPhe-QYCFADPY[Nle]CA |
| BCY7167 | 130 | [PEG3]-ACIEE-DGlu-QYCFADPY[Nle]CA |
| BCY7168 | 131 | [PEG3]-ACIEE-DGln-QYCFADPY[Nle]CA |
| BCY7169 | 132 | [PEG3]-ACIEE-DLeu-QYCFADPY[Nle]CA |
| BCY7170 | 133 | [PEG3]-ACIEE-DSer-QYCFADPY[Nle]CA |
| BCY7174 | 136 | [PEG3]-ACIEEGPYCFADPY[Nle]CA |
| BCY7175 | 137 | [PEG3]-ACIEEGQFCFADPY[Nle]CA |
| BCY7177 | 139 | [PEG3]-ACIEEGQ-3MeF-CFADPY[Nle]CA |
| BCY7178 | 140 | [PEG3]-ACIEEGQ-4MeF-CFADPY[Nle]CA |
| BCY7179 | 141 | [PEG3]-ACIEEGQ-4FF-CFADPY[Nle]CA |

-continued

| Peptide Number | SEQ ID NO: | Sequence |
|---|---|---|
| BCY7183 | 145 | [PEG3]-ACIEEGQYC-4MeF-ADPY[Nle]CA |
| BCY7185 | 147 | [PEG3]-ACIEEGQYC-4FF-ADPY[Nle]CA |
| BCY7195 | 156 | [PEG3]AC[tBuAla]EEGQYCFADPY[Nle]CA |
| BCY7198 | 159 | [PEG3]ACIEEGQYC[2FPhe]ADPY[Nle]CA |
| BCY7211 | 170 | [PEG3]ACIEEGQYCFADPY[HLeu]CA |
| BCY7311 | 188 | [PEG3]-ACIEEGQYCFADPY[Ahp]CA |
| BCY7768 | 195 | [PEG3]ACIPE[dF]QYCFADPY[Nle]CA |
| BCY7770 | 196 | [PEG3]ACIPE[dF]PYCFADPY[Nle]CA |
| BCY7772 | 197 | [PEG3]ACIEE[dF]PYCFADPY[Nle]CA |
| BCY7773 | 198 | PEG3]ACIPEGPYCFADPY[Nle]CA |
| BCY7774 | 199 | PEG3]AC[tBuAla]PE[dF]P[4MePhe]C[4FPhe]ADPY[Nle]CA |
| BCY7775 | 200 | [PEG3]AC[tBuAla]PE[dF]Q[4MePhe]C[4FPhe]ADPY[Nle]CA |
| BCY7776 | 201 | [PEG3]AC[tBuAla]EE[dF]P[4MePhe]C[4FPhe]ADPY[Nle]CA |
| BCY7796 | 203 | [PEG3]ACI[HyP]EGQYCFADPY[Nle]CA |
| BCY7798 | 204 | [PEG3]ACIEE[dW]QYCFADPY[Nle]CA |
| BCY7801 | 207 | PEG3]ACIEEGQ[2Nal]CFADPY[Nle]CA |
| BCY7802 | 208 | PEG3]ACIEEGQ[4MeoPhe]CFADPY[Nle]CA |
| BCY7936 | 223 | [Ac]ACIEEGQ[44BPA]CFADPY[Nle]CA |
| BCY7941 | 227 | [Ac]ACIEEGQYC[4Pal]ADPY[Nle]CA |
| BCY7942 | 228 | [Ac]ACIEEGQYC[44BPA]ADPY[Nle]CA |
| BCY7944 | 230 | Ac]ACIEEGQYC[4tBuPhe]ADPY[Nle]CA |
| BCY7950 | 232 | [Ac]ACIEEG[55DMP]YCFADPY[Nle]CA |
| BCY7954 | 234 | [Ac]ACIEEG[Oic]YCFADPY[Nle]CA |
| BCY7958 | 238 | [Ac]ACI[Oxa]EGQYCFADPY[Nle]CA |
| BCY7959 | 239 | [Ac]ACIEEG[Oxa]YCFADPY[Nle]CA |
| BCY7960 | 240 | [Ac]ACIPEGPYCFADPY[Nle]CA |
| BCY7952 | 241 | [Ac]ACIEEG[HyP]YCFADPY[Nle]CA |
| BCY7961 | 242 | [Ac]ACIPE[dA]PYCFADPY[Nle]CA |
| BCY8656 | 245 | [Ac]AC[tBuAla]EEGQYCFADPY[Nle]CA |
| BCY8659 | 248 | [Ac]ACIPEGQYCFADPY[Nle]CA |
| BCY8663 | 252 | [Ac]ACIEE[df]QYCFADPY[Nle]CA |
| BCY8668 | 256 | [Ac]ACIEEG[Aib]YCFADPY[Nle]CA |
| BCY8669 | 257 | [Ac]ACIEEG[AC5C]YCFADPY[Nle]CA |
| BCY8674 | 261 | [Ac]ACIEEGQYC[NO2Phe]ADPY[Nle]CA |
| BCY8675 | 262 | [Ac]ACIEEGQYC[4BrPhe]ADPY[Nle]CA |
| BCY9273 | 265 | [Ac]ACIEEGQYCFADPYWICA |
| BCY3814 | 31 | ACIEEGQYCFADPY(Nle)CA |

-continued

| Peptide Number | SEQ ID NO: | Sequence |
|---|---|---|
| BCY7527 | 194 | [Ac]C1EEGQYCFADPY[Nle]C[Dap] |
| BCY7965 | 243 | [Ac]AC[tBuAla]PE[dA]PYCFADPY[Nle]CA. |

9. The peptide ligand as defined in claim 7, which comprises three cysteine residues separated by two loop sequences both of which consist of 6 amino acids, and said peptide ligand comprises an amino acid sequence selected from:

$$C_i-X_5-X_6-X_7-X_8-X_9-X_{10}-C_{ii}-X_{11}-A-D-P-Y-X_{15}-C_{iii};$$
(SEQ ID NO: 267)

wherein $C_i$, $C_{ii}$ and $C_{iii}$ represent first, second and third cysteine residues, respectively;
$X_5$ represents Ile or tBuAla;
$X_6$ represents Lys, Glu or Pro;
$X_7$ represents Glu or D-Lys;
$X_8$ represents Gly, D-Lys, D-Phe or D-Ala;
$X_9$ represents Gln, Lys or Pro;
$X_{10}$ represents Tyr or 4MePhe;
$X_{11}$ represents Phe or 4FPhe; and
$X_{15}$ represents Met or Nle.

10. The peptide ligand as defined in claim 9, wherein the peptide ligand of SEQ ID NO: 267 is selected from the $C_i$ to $C_{iii}$ sequences of the following peptides or the full sequences of the following peptides:

| Peptide Number | SEQ ID NO: | Sequence |
|---|---|---|
| BCY7239 | 52 | Ac-CIK(Peg12)EGQYCFADPYMC |
| BCY7240 | 53 | Ac-CIEK(Peg12)GQYCFADPYMC |
| BCY7242 | 55 | Ac-CIEEGK(Peg12)YCFADPYMC |
| BCY7416 | 63 | [Ac]CIEE[dK(PEG12F1)]QYCFADPY[Nle]C |
| BCY7156 | 119 | [PEG3]-ACIPEGQYCFADPY[Nle]CA |
| BCY7166 | 129 | [PEG3]-ACIEE-DPhe-QYCFADPY[Nle]CA |
| BCY7174 | 136 | [PEG3]-ACIEEGPYCFADPY[Nle]CA |
| BCY7774 | 199 | PEG3]AC[tBuAla]PE[dF]P[4MePhe]C[4FPhe]ADPY[Nle]CA |
| BCY9273 | 265 | [Ac]ACIEEGQYCFADPYMCA |
| BCY3814 | 31 | ACIEEGQYCFADPY(Nle)CA |
| BCY7527 | 194 | [Ac]CIEEGQYCFADPY[Nle]C[Dap] |
| BCY7965 | 243 | [Ac]AC[tBuAla]PE[dA]PYCFADPY[Nle]CA. |

11. The peptide ligand as defined in claim 1, wherein the molecular scaffold is 1,1',1''-(1,3,5-triazinane-1,3,5-triyl) triprop-2-en-1-one (TATA).

12. The peptide ligand as defined in claim 1, wherein the pharmaceutically acceptable salt is selected from the free acid or the sodium, potassium, calcium, or ammonium salt.

13. The peptide ligand as defined in claim 1, wherein the CD137 is human CD137.

14. A drug conjugate comprising the peptide ligand as defined in claim 1, conjugated to one or more effector and/or functional groups.

15. A drug conjugate comprising the peptide ligand as defined in claim 1, conjugated to one or more cytotoxic agents.

16. A pharmaceutical composition which comprises the peptide ligand of claim 1, in combination with one or more pharmaceutically acceptable excipients.

17. The peptide ligand as defined in claim 6, wherein the molecular scaffold is 1,1',1''-(1,3,5-triazinane-1,3,5-triyl) triprop-2-en-1-one (TATA).

18. The peptide ligand as defined in claim 7, wherein the molecular scaffold is 1,1',1''-(1,3,5-triazinane-1,3,5-triyl) triprop-2-en-1-one (TATA).

19. A drug conjugate comprising the peptide ligand as defined in claim 6, conjugated to one or more effector and/or functional groups.

20. A drug conjugate comprising the peptide ligand as defined in claim 7, conjugated to one or more effector and/or functional groups.

21. A pharmaceutical composition which comprises the peptide ligand of claim 6, in combination with one or more pharmaceutically acceptable excipients.

22. A pharmaceutical composition which comprises the peptide ligand of claim 7, in combination with one or more pharmaceutically acceptable excipients.

23. The drug conjugate of claim 14, wherein the peptide ligand is as defined in claim 2.

24. The drug conjugate of claim 20, wherein the peptide ligand is as defined in claim 8.

25. The drug conjugate of claim 20, wherein the peptide ligand is as defined in claim 10.

* * * * *